(12) United States Patent
Hauer et al.

(10) Patent No.: US 9,587,257 B2
(45) Date of Patent: *Mar. 7, 2017

(54) METHOD FOR THE ENZYME-CATALYSED HYDROLYSIS OF POLYACRYLIC ACID ESTERS, AND ESTERASES USED THEREFOR

(71) Applicant: BASF SE, Ludwigshafen (DE)

(72) Inventors: Bernhard Hauer, Fußgönheim (DE); Hans Wolfgang Höffken, Ludwigshafen (DE); Cecilia Kvarnström Branneby, Stockholm (SE); Helmut Schwab, Graz (AT); Sabine Feichtenhofer, Graz (AT); Marlene Buchebner, Graz (AT); Brigitte Pohn, Graz (AT)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/013,299

(22) Filed: Feb. 2, 2016

(65) Prior Publication Data
US 2016/0168602 A1    Jun. 16, 2016

Related U.S. Application Data

(63) Continuation of application No. 14/100,680, filed on Dec. 9, 2013, now abandoned, which is a continuation of application No. 13/003,597, filed as application No. PCT/EP2009/059212 on Jul. 17, 2009, now Pat. No. 8,617,858.

(30) Foreign Application Priority Data

Jul. 18, 2008   (EP) .................................... 08160774

(51) Int. Cl.
| C12P 7/52 | (2006.01) |
| C12P 7/62 | (2006.01) |
| C12N 9/16 | (2006.01) |
| C12N 9/18 | (2006.01) |

(52) U.S. Cl.
CPC .............. *C12P 7/62* (2013.01); *C12N 9/16* (2013.01); *C12N 9/18* (2013.01); *C12Y 301/01001* (2013.01)

(58) Field of Classification Search
CPC ................ C12N 9/16; C12N 9/18; C12P 7/62
USPC ........................................................ 435/141
See application file for complete search history.

(56) References Cited

U.S. PATENT DOCUMENTS

| 3,926,891 | A | 12/1975 | Gross et al. |
| 8,617,858 | B2 * | 12/2013 | Hauer .................. C12N 9/16 435/141 |
| 2004/0082023 | A1 | 4/2004 | Gross et al. |
| 2009/0325225 | A1 | 12/2009 | Breuer |
| 2010/0009421 | A1 | 1/2010 | Stuermer et al. |
| 2010/0035315 | A1 | 2/2010 | Stuermer et al. |
| 2010/0189777 | A1 | 7/2010 | Schwaneberg et al. |
| 2010/0273223 | A1 | 10/2010 | Hauer et al. |
| 2010/0291640 | A1 | 11/2010 | Stuermer et al. |
| 2010/0304448 | A1 | 12/2010 | Sturmer et al. |
| 2010/0311037 | A1 | 12/2010 | Hauer et al. |
| 2011/0178335 | A1 | 7/2011 | Leung et al. |

FOREIGN PATENT DOCUMENTS

| DE | 10305076 A1 | 8/2004 |
| WO | WO-2005/040487 A1 | 5/2005 |

OTHER PUBLICATIONS

Arpigny, J. L., et al., "Bacterial Lipolytic Enzymes: Classification and Properties", Biochem. J., vol. 343, (1999), pp. 177-183.
Bellucci, R., et al., "A Preliminary Note on the Use of Enzymes in Conservation: The Removal of Aged Acrylic Resin Coatings with Lipase", Studies in Conservation, vol. 44, (1999), pp. 278-281.
Hasslacher, M., et al., "Molecular Cloning of the Full-length cDNA of (S)-Hydroxynitrile Lyase from *Hevea brasiliensis*", The Journal of biological Chemistry, vol. 271, No. 10, (1996). pp. 5884-5891.
Hughes, J., et al., "Purification, Characterization, and Cloning of alpha-Hydroxynitrile Lyase from Cassava (*Manihot esculenta* Crantz)", Archives of Biochemistry and Biophysics, vol. 311, No. 2, (1994), pp. 496-502.
Inprakhon, P., et al., "Regioselectivity of Enzymatic Modification of Poly(methyl acrylate)", Journal of Biotechnology, vol. 131, (2007), pp. 418-424.
Ivancic, M., et al., "Inverting Enantioselectivity of *Burkholderia gladioli* Esterase EstB by Directed and Designed Evolution", Journal of Biotechnology, vol. 129, (2007), pp. 109-122.
Lalot, T., et al., "Lipozyme-catalyzed Transesterification of Oligo(methylacrylate)s", Polymer Bulletine, vol. 26, (1991), pp. 55-62.
Mahalik, J.P., et al., "Effect of the Alkyl Group Substituents on the Thermal and Enzymatic Degradation of Poly(*n*-alkyl acrylates)", Ind. Eng. Chem. Res., vol. 44, (2005), pp. 4171-4177.
O'Sullivan, C., et al., "Hydrolysis of Poly (n-butylcyanoacrylate) Nanoparticles Using Esterase", Polymer Degradation and Stability, vol. 78, (2002), pp. 7-15.

(Continued)

*Primary Examiner* — Tekchand Saidha
(74) *Attorney, Agent, or Firm* — Drinker Biddle & Reath LLP

(57) ABSTRACT

The invention relates to a method for the enzyme-catalysed hydrolysis of polyacrylic acid esters. According to the method, at least one polyacrylic acid ester is provided and incubated with at least one enzyme selected from enzymes (EC 3.1) acting on ester bindings, until the ester groups contained in the polyacrylic acid ester are partially or fully hydrolytically split, and optionally the modified polymer obtained thereby is isolated. The invention also relates to the enzymes used and mutants thereof, nucleic acids coding for the enzymes, vectors comprising the nucleic acids, microorganisms comprising the vectors, and the use of the enzymes, the vectors or the micro-organisms for carrying out a method for the enzyme-catalysed hydrolysis of polyacrylic acid esters. The present application also relates to polymer reaction products that can be obtained by the method, and methods for producing esterases.

12 Claims, 7 Drawing Sheets

(56) References Cited

OTHER PUBLICATIONS

Petersen, E. I., et al., "A Novel Esterase from *Burkholderia gladioli* Which Shows High Deacetylation Activity on Cephalosporins is Related to β-Lactamases and DD-peptidases", Journal of Biotechnology, vol. 89, (2001), pp. 11-25.

Reiter, B., et al., "Cloning and Characterization of EstC from *Burkholderia gladioli*, A Novel-Type Esterase Related to Plant Enzymes", Appl. Microbiol. Biotechnol., vol. 54, (2000), pp. 778-785.

Tor, R., et al., "Enzymatically Catalysed Transesterifications of Acryl and Methacryl Monomeric Esters", Enzyme Microb. Technol., vol. 12, 91990), pp. 299-304.

Valinger, G., et al., "Stability and Activity Improvement of Cephalosporin Esterase EstB from *Burkholderia gladioli* by Directed Evolution and Structural Interpretation of Muteins", Journal of Biotechnology, vol. 129, (2007), pp. 98-108.

\* cited by examiner

| Variante | Mutation | PMA | PBA | DG | DB | α-N |
|---|---|---|---|---|---|---|
| EstC | ----- | ++ | o | ++ | o | ++ |
| 2K20 | Leu193Ala | +++ | o | +++ | o | +++ |
| 2K29 | Leu193Ala, Phe138Ala | + | + | ++ | + | +++ |
| B48 | Leu193Ala, Phe138Ala, Thr188Ser | ++ | + | ++ | + | +++ |
| A14 | Leu193Ala, Phe138Ala, Thr188Ser, Leu160Ala, Val150Ala | + | + | ++ | + | +++ |
| B31 | Leu193Ala, Phe138Ala, Thr188Ser, Val150Ala | + | + | ++ | + | + |
| C12 | Leu193Ala, Phe138Val | ++ | + | +++ | + | +++ |
| A4 | Leu193Ala, Phe138Val, Thr188Ser | ++ | + | +++ | + | +++ |
| A13 | Leu193Ala, Phe138Val, Thr188Ser, Leu160Ala | ++ | + | ++ | + | +++ |
| A18 | Leu193Ala, Phe138Val, Thr188Ser, Val150Ala | ++ | + | ++ | + | +++ |
| A7 | Leu193Ala, Thr188Ser | ++ | + | ++ | + | +++ |
| 1K22 | Phe138Ala | +++ | o | +++ | o | +++ |
| B4 | Phe138Ala, Leu160Ala, Thr188Ser | ++ | o | +++ | o | ++ |
| B7 | Phe138Ala, Thr188Ser | +++ | o | +++ | + | ++ |
| A11 | Phe138Val | ++ | o | +++ | o | ++ |
| C10 | Phe138Val, Glu154Ala | ++ | o | +++ | o | ++ |
| A2 | Phe138Val, Thr188Ser | ++ | o | +++ | o | ++ |
| A15 | Phe138Val, Val150Ala, Thr188Ser | ++ | o | +++ | o | ++ |
| A101 | Val150Ala | +++ | o | +++ | o | ++ |
| A102 | Val150Ala, Thr188Ser | +++ | o | +++ | o | ++ |

Fig. 5a Review of mutations and activities. +++ = very active, ++ = active, + = weakly active, o = inactive

| Variante | Mutation | PMA | PBA | DG | DB |
|---|---|---|---|---|---|
| EstB | ----- | ++ | +++ | o | o |
| NJ70 | Pro8Leu, Gly132Ser, Trp134Arg, Arg155Cys, Glu251Gly, Ala311Val, Glu316Lys | ++ | +++ | + | o |
| N27 | Ser17Leu, Gly132Ser, Glu251Gly, Ala311Val, Glu316Lys | ++ | +++ | + | o |

Fig. 5b Review of mutations and activities of the EstB variants, +++ = very active, ++ = active, + = weakly active, o = inactive

SEQUENCE LISTING

<160> NUMBER OF SEQ ID NOS: 59

<210> SEQ ID NO 1
<211> LENGTH: 392
<212> TYPE: PRT
<213> ORGANISM: Burkholderia gladioli

<400> SEQUENCE: 1

Met Thr Ala Ala Ser Leu Asp Pro Thr Ala Phe Ser Leu Asp Ala Ala
1               5                   10                  15

Ser Leu Ala Ala Arg Leu Asp Ala Val Phe Asp Gln Ala Leu Arg Glu
            20                  25                  30

Arg Arg Leu Val Gly Ala Val Ala Ile Val Ala Arg His Gly Glu Ile
        35                  40                  45

Leu Tyr Arg Arg Ala Gln Gly Leu Ala Asp Arg Glu Ala Gly Arg Pro
    50                  55                  60

Met Arg Glu Asp Thr Leu Phe Arg Leu Ala Ser Val Thr Lys Pro Ile
65                  70                  75                  80

Val Ala Leu Ala Val Leu Arg Leu Val Ala Arg Gly Glu Leu Ala Leu
                85                  90                  95

Asp Ala Pro Val Thr Arg Trp Leu Pro Glu Phe Arg Pro Arg Leu Ala
            100                 105                 110

Asp Gly Ser Glu Pro Leu Val Thr Ile His His Leu Leu Thr His Thr
        115                 120                 125

Ser Gly Leu Gly Tyr Trp Leu Leu Glu Gly Ala Gly Ser Val Tyr Asp
    130                 135                 140

Arg Leu Gly Ile Ser Asp Gly Ile Asp Leu Arg Asp Phe Asp Leu Asp
145                 150                 155                 160

Glu Asn Leu Arg Arg Leu Ala Ser Ala Pro Leu Ser Phe Ala Pro Gly
                165                 170                 175

Ser Gly Trp Gln Tyr Ser Leu Ala Leu Asp Val Leu Gly Ala Val Val
            180                 185                 190

Glu Arg Ala Thr Gly Gln Pro Leu Ala Ala Ala Val Asp Ala Leu Val
        195                 200                 205

Ala Gln Pro Leu Gly Met Arg Asp Cys Gly Phe Val Ser Ala Glu Pro
    210                 215                 220

Glu Arg Phe Ala Val Pro Tyr His Asp Gly Gln Pro Glu Pro Val Arg
225                 230                 235                 240

Met Arg Asp Gly Ile Glu Val Pro Leu Pro Glu Gly His Gly Ala Ala
                245                 250                 255

Val Arg Phe Ala Pro Ser Arg Val Phe Glu Pro Gly Ala Tyr Pro Ser
            260                 265                 270

Gly Gly Ala Gly Met Tyr Gly Ser Ala Asp Asp Val Leu Arg Ala Leu
        275                 280                 285

Glu Ala Ile Arg Ala Asn Pro Gly Phe Leu Pro Glu Thr Leu Ala Asp
    290                 295                 300

Ala Ala Arg Arg Asp Gln Ala Gly Val Gly Ala Glu Thr Arg Gly Pro
305                 310                 315                 320

Gly Trp Gly Phe Gly Tyr Leu Ser Ala Val Leu Asp Asp Pro Ala Ala
                325                 330                 335

Ala Gly Thr Pro Gln His Ala Gly Thr Leu Gln Trp Gly Gly Val Tyr
            340                 345                 350

Gly His Ser Trp Phe Val Asp Arg Ala Leu Gly Leu Ser Val Leu Leu
        355                 360                 365

-continued

```
Leu Thr Asn Thr Ala Tyr Glu Gly Met Ser Gly Pro Leu Thr Ile Ala
    370                 375                 380

Leu Arg Asp Ala Val Tyr Ala Arg
385                 390

<210> SEQ ID NO 2
<211> LENGTH: 298
<212> TYPE: PRT
<213> ORGANISM: Burkholderia gladioli

<400> SEQUENCE: 2

Met Asn His Pro Asp Ile Asp Thr His Ser Arg Asn Ala Ala Ala Pro
1               5                   10                  15

Leu Pro Phe Val Leu Val His Gly Ala Trp His Gly Ala Trp Ala Tyr
            20                  25                  30

Glu Arg Leu Gly Ala Ala Leu Ala Ala Arg Gly His Ala Ser Val Ala
        35                  40                  45

His Asp Leu Pro Ala His Gly Ile Asn Ala Arg Tyr Pro Ala Ala Phe
    50                  55                  60

Trp Gln Gly Asp Ala Gln Ala Leu Ala Gln Glu Pro Ser Pro Val Ala
65                  70                  75                  80

Ala Thr Thr Leu Asp Asp Tyr Thr Gly Gln Val Leu Arg Ala Ile Asp
                85                  90                  95

Ala Ala Cys Ala Leu Gly His Pro Arg Val Val Leu Val Gly His Ser
            100                 105                 110

Met Gly Gly Val Ala Ile Thr Ala Ala Ala Glu Arg Ala Pro Glu Arg
        115                 120                 125

Ile Ala Ala Leu Val Tyr Leu Ala Ala Phe Met Pro Ala Ser Gly Val
    130                 135                 140

Pro Gly Leu Asp Tyr Val Arg Ala Pro Glu Asn His Gly Glu Met Leu
145                 150                 155                 160

Ala Ser Leu Ile Cys Ala Ser Pro Arg Ala Ile Gly Ala Leu Arg Ile
                165                 170                 175

Asn Pro Ala Ser Arg Asp Ala Ala Tyr Leu Ala Thr Leu Lys Gln Ala
            180                 185                 190

Leu Phe Glu Asp Val Asp Glu Ala Thr Phe Arg Ala Val Thr Arg Leu
        195                 200                 205

Met Ser Ser Asp Val Pro Thr Ala Pro Phe Ala Thr Pro Ile Ala Thr
    210                 215                 220

Thr Ala Glu Arg Trp Gly Ser Ile Ala Arg His Tyr Val Thr Cys Ala
225                 230                 235                 240

Glu Asp Arg Val Ile Leu Pro Ala Leu Gln Arg Arg Phe Ile Ala Glu
                245                 250                 255

Ala Asp Ala Phe Leu Pro Glu Arg Pro Thr Arg Val His Ala Leu Asp
            260                 265                 270

Ser Ser His Ser Pro Phe Leu Ser Gln Pro Asp Thr Leu Ala Glu Leu
        275                 280                 285

Leu Thr Gly Ile Ala Arg Asn Thr Ala Ile
    290                 295

<210> SEQ ID NO 3
<211> LENGTH: 392
<212> TYPE: PRT
<213> ORGANISM: Artificial sequence
<220> FEATURE:
<223> OTHER INFORMATION: Modified from SEQ ID NO:1; internal
      designation: N27
```

```
<220> FEATURE:
<221> NAME/KEY: MISC_FEATURE
<222> LOCATION: (17)..(17)
<223> OTHER INFORMATION: serine 17 of wildtype (SEQ ID NO:1) replaced
      by leucine
<220> FEATURE:
<221> NAME/KEY: MISC_FEATURE
<222> LOCATION: (132)..(132)
<223> OTHER INFORMATION: glycine 132 of wildtype (SEQ ID NO:1) replaced
      by serine
<220> FEATURE:
<221> NAME/KEY: MISC_FEATURE
<222> LOCATION: (251)..(251)
<223> OTHER INFORMATION: glutamic acid  251 of wildtype (SEQ ID NO:1)
      replaced by glycine
<220> FEATURE:
<221> NAME/KEY: MISC_FEATURE
<222> LOCATION: (311)..(311)
<223> OTHER INFORMATION: alanine 311 of wildtype (SEQ ID NO:1) replaced
      by valine
<220> FEATURE:
<221> NAME/KEY: MISC_FEATURE
<222> LOCATION: (316)..(316)
<223> OTHER INFORMATION: glutamic acid 316 of wildtype (SEQ ID NO:1)
      replaced by lysine

<400> SEQUENCE: 3

Met Thr Ala Ala Ser Leu Asp Pro Thr Ala Phe Ser Leu Asp Ala Ala
1               5                   10                  15

Leu Leu Ala Ala Arg Leu Asp Ala Val Phe Asp Gln Ala Leu Arg Glu
            20                  25                  30

Arg Arg Leu Val Gly Ala Val Ala Ile Val Ala Arg His Gly Glu Ile
        35                  40                  45

Leu Tyr Arg Arg Ala Gln Gly Leu Ala Asp Arg Glu Ala Gly Arg Pro
    50                  55                  60

Met Arg Glu Asp Thr Leu Phe Arg Leu Ala Ser Val Thr Lys Pro Ile
65                  70                  75                  80

Val Ala Leu Ala Val Leu Arg Leu Val Ala Arg Gly Glu Leu Ala Leu
                85                  90                  95

Asp Ala Pro Val Thr Arg Trp Leu Pro Glu Phe Arg Pro Arg Leu Ala
            100                 105                 110

Asp Gly Ser Glu Pro Leu Val Thr Ile His His Leu Leu Thr His Thr
        115                 120                 125

Ser Gly Leu Ser Tyr Trp Leu Leu Glu Gly Ala Gly Ser Val Tyr Asp
    130                 135                 140

Arg Leu Gly Ile Ser Asp Gly Ile Asp Leu Arg Asp Phe Asp Leu Asp
145                 150                 155                 160

Glu Asn Leu Arg Arg Leu Ala Ser Ala Pro Leu Ser Phe Ala Pro Gly
                165                 170                 175

Ser Gly Trp Gln Tyr Ser Leu Ala Leu Asp Val Leu Gly Ala Val Val
            180                 185                 190

Glu Arg Ala Thr Gly Gln Pro Leu Ala Ala Val Asp Ala Leu Val
        195                 200                 205

Ala Gln Pro Leu Gly Met Arg Asp Cys Gly Phe Val Ser Ala Glu Pro
    210                 215                 220

Glu Arg Phe Ala Val Pro Tyr His Asp Gly Gln Pro Glu Pro Val Arg
225                 230                 235                 240

Met Arg Asp Gly Ile Glu Val Pro Leu Pro Gly Gly His Gly Ala Ala
                245                 250                 255

Val Arg Phe Ala Pro Ser Arg Val Phe Glu Pro Gly Ala Tyr Pro Ser
            260                 265                 270
```

```
Gly Gly Ala Gly Met Tyr Gly Ser Ala Asp Asp Val Leu Arg Ala Leu
            275                 280                 285

Glu Ala Ile Arg Ala Asn Pro Gly Phe Leu Pro Glu Thr Leu Ala Asp
        290                 295                 300

Ala Ala Arg Arg Asp Gln Val Gly Val Gly Ala Lys Thr Arg Gly Pro
305                 310                 315                 320

Gly Trp Gly Phe Gly Tyr Leu Ser Ala Val Leu Asp Asp Pro Ala Ala
                325                 330                 335

Ala Gly Thr Pro Gln His Ala Gly Thr Leu Gln Trp Gly Gly Val Tyr
            340                 345                 350

Gly His Ser Trp Phe Val Asp Arg Ala Leu Gly Leu Ser Val Leu Leu
        355                 360                 365

Leu Thr Asn Thr Ala Tyr Glu Gly Met Ser Gly Pro Leu Thr Ile Ala
    370                 375                 380

Leu Arg Asp Ala Val Tyr Ala Arg
385                 390
```

<210> SEQ ID NO 4
<211> LENGTH: 392
<212> TYPE: PRT
<213> ORGANISM: Artificial sequence
<220> FEATURE:
<223> OTHER INFORMATION: modified from SEQ ID NO:1; internal
      designation NJ70
<220> FEATURE:
<221> NAME/KEY: MISC_FEATURE
<222> LOCATION: (8)..(8)
<223> OTHER INFORMATION: proline of wildtype (SEQ ID NO:1) replaced by
      leucine
<220> FEATURE:
<221> NAME/KEY: MISC_FEATURE
<222> LOCATION: (132)..(132)
<223> OTHER INFORMATION: glycine 132 of wildtype (SEQ ID NO:1) replaced
      by serine
<220> FEATURE:
<221> NAME/KEY: MISC_FEATURE
<222> LOCATION: (134)..(134)
<223> OTHER INFORMATION: tryptophane 134 of wildtype (SEQ ID NO:1)
      replaced by arginine
<220> FEATURE:
<221> NAME/KEY: MISC_FEATURE
<222> LOCATION: (155)..(155)
<223> OTHER INFORMATION: arginine 155 of wildtype (SEQ ID NO:1) replaced
      by cysteine
<220> FEATURE:
<221> NAME/KEY: MISC_FEATURE
<222> LOCATION: (251)..(251)
<223> OTHER INFORMATION: glutamic acid 251 of wildtype (SEQ ID NO:1)
      replaced by glycine
<220> FEATURE:
<221> NAME/KEY: MISC_FEATURE
<222> LOCATION: (311)..(311)
<223> OTHER INFORMATION: alanine 311 of wildtype (SEQ ID NO:1) replaced
      by valine
<220> FEATURE:
<221> NAME/KEY: MISC_FEATURE
<222> LOCATION: (316)..(316)
<223> OTHER INFORMATION: glutamic acid 316 of wildtype (SEQ ID NO:1)
      replaced by lysine

<400> SEQUENCE: 4

```
Met Thr Ala Ala Ser Leu Asp Leu Thr Ala Phe Ser Leu Asp Ala Ala
1               5                   10                  15

Ser Leu Ala Ala Arg Leu Asp Ala Val Phe Asp Gln Ala Leu Arg Glu
            20                  25                  30

Arg Arg Leu Val Gly Ala Val Ala Ile Val Ala Arg His Gly Glu Ile
        35                  40                  45
```

```
Leu Tyr Arg Arg Ala Gln Gly Leu Ala Asp Arg Glu Ala Gly Arg Pro
        50                  55                  60

Met Arg Glu Asp Thr Leu Phe Arg Leu Ala Ser Val Thr Lys Pro Ile
 65                  70                  75                  80

Val Ala Leu Ala Val Leu Arg Leu Val Ala Arg Gly Glu Leu Ala Leu
                85                  90                  95

Asp Ala Pro Val Thr Arg Trp Leu Pro Glu Phe Arg Pro Arg Leu Ala
               100                 105                 110

Asp Gly Ser Glu Pro Leu Val Thr Ile His His Leu Thr His Thr
               115                 120                 125

Ser Gly Leu Ser Tyr Arg Leu Leu Glu Gly Ala Gly Ser Val Tyr Asp
       130                 135                 140

Arg Leu Gly Ile Ser Asp Gly Ile Asp Leu Cys Asp Phe Asp Leu Asp
145                 150                 155                 160

Glu Asn Leu Arg Arg Leu Ala Ser Ala Pro Leu Ser Phe Ala Pro Gly
                165                 170                 175

Ser Gly Trp Gln Tyr Ser Leu Ala Leu Asp Val Leu Gly Ala Val Val
               180                 185                 190

Glu Arg Ala Thr Gly Gln Pro Leu Ala Ala Val Asp Ala Leu Val
       195                 200                 205

Ala Gln Pro Leu Gly Met Arg Asp Cys Gly Phe Val Ser Ala Glu Pro
       210                 215                 220

Glu Arg Phe Ala Val Pro Tyr His Asp Gly Gln Pro Glu Pro Val Arg
225                 230                 235                 240

Met Arg Asp Gly Ile Glu Val Pro Leu Pro Gly Gly His Gly Ala Ala
                245                 250                 255

Val Arg Phe Ala Pro Ser Arg Val Phe Glu Pro Gly Ala Tyr Pro Ser
               260                 265                 270

Gly Gly Ala Gly Met Tyr Gly Ser Ala Asp Asp Val Leu Arg Ala Leu
       275                 280                 285

Glu Ala Ile Arg Ala Asn Pro Gly Phe Leu Pro Glu Thr Leu Ala Asp
       290                 295                 300

Ala Ala Arg Arg Asp Gln Val Gly Val Gly Ala Lys Thr Arg Gly Pro
305                 310                 315                 320

Gly Trp Gly Phe Gly Tyr Leu Ser Ala Val Leu Asp Asp Pro Ala Ala
                325                 330                 335

Ala Gly Thr Pro Gln His Ala Gly Thr Leu Gln Trp Gly Gly Val Tyr
               340                 345                 350

Gly His Ser Trp Phe Val Asp Arg Ala Leu Gly Leu Ser Val Leu Leu
       355                 360                 365

Leu Thr Asn Thr Ala Tyr Glu Gly Met Ser Gly Pro Leu Thr Ile Ala
370                 375                 380

Leu Arg Asp Ala Val Tyr Ala Arg
385                 390

<210> SEQ ID NO 5
<211> LENGTH: 194
<212> TYPE: PRT
<213> ORGANISM: Humicola insolens
<220> FEATURE:
<221> NAME/KEY: MISC_FEATURE
<223> OTHER INFORMATION: Cutinase from Humicula insolens

<400> SEQUENCE: 5

Gly Thr Gly Ala Ile Glu Asn Gly Leu Glu Ser Gly Ser Ala Asn Ala
1               5                  10                  15
```

-continued

```
Cys Pro Asp Ala Ile Leu Ile Phe Ala Arg Gly Ser Thr Glu Pro Gly
            20                  25                  30

Asn Met Gly Ile Thr Val Gly Pro Ala Leu Ala Asn Gly Leu Glu Ser
        35                  40                  45

His Ile Arg Asn Ile Trp Ile Gln Gly Val Gly Pro Tyr Asp Ala
 50                  55                  60

Ala Leu Ala Thr Asn Phe Leu Pro Arg Gly Thr Ser Gln Ala Asn Ile
 65                  70                  75                  80

Asp Glu Gly Lys Arg Leu Phe Ala Leu Ala Asn Gln Lys Cys Pro Asn
                85                  90                  95

Thr Pro Val Val Ala Gly Gly Tyr Ser Gln Gly Ala Ala Leu Ile Ala
            100                 105                 110

Ala Ala Val Ser Glu Leu Ser Gly Ala Val Lys Glu Gln Val Lys Gly
            115                 120                 125

Val Ala Leu Phe Gly Tyr Thr Gln Asn Leu Gln Asn Arg Gly Gly Ile
    130                 135                 140

Pro Asn Tyr Pro Arg Glu Arg Thr Lys Val Phe Cys Asn Val Gly Asp
145                 150                 155                 160

Ala Val Cys Thr Gly Thr Leu Ile Ile Thr Pro Ala His Leu Ser Tyr
                165                 170                 175

Thr Ile Glu Ala Arg Gly Glu Ala Ala Arg Phe Leu Arg Asp Arg Ile
            180                 185                 190

Arg Ala
```

```
<210> SEQ ID NO 6
<211> LENGTH: 317
<212> TYPE: PRT
<213> ORGANISM: Candida antarctica
<220> FEATURE:
<221> NAME/KEY: MISC_FEATURE
<223> OTHER INFORMATION: Lipase B from Candida antarctica

<400> SEQUENCE: 6

Leu Pro Ser Gly Ser Asp Pro Ala Phe Ser Gln Pro Lys Ser Val Leu
1               5                   10                  15

Asp Ala Gly Leu Thr Cys Gln Gly Ala Ser Pro Ser Ser Val Ser Lys
            20                  25                  30

Pro Ile Leu Leu Val Pro Gly Thr Gly Thr Thr Gly Pro Gln Ser Phe
        35                  40                  45

Asp Ser Asn Trp Ile Pro Leu Ser Ala Gln Leu Gly Tyr Thr Pro Cys
    50                  55                  60

Trp Ile Ser Pro Pro Pro Phe Met Leu Asn Asp Thr Gln Val Asn Thr
65                  70                  75                  80

Glu Tyr Met Val Asn Ala Ile Thr Thr Leu Tyr Ala Gly Ser Gly Asn
                85                  90                  95

Asn Lys Leu Pro Val Leu Thr Trp Ser Gln Gly Gly Leu Val Ala Gln
            100                 105                 110

Trp Gly Leu Thr Phe Phe Pro Ser Ile Arg Ser Lys Val Asp Arg Leu
        115                 120                 125

Met Ala Phe Ala Pro Asp Tyr Lys Gly Thr Val Leu Ala Gly Pro Leu
    130                 135                 140

Asp Ala Leu Ala Val Ser Ala Pro Ser Val Trp Gln Gln Thr Thr Gly
145                 150                 155                 160

Ser Ala Leu Thr Thr Ala Leu Arg Asn Ala Gly Gly Leu Thr Gln Ile
                165                 170                 175
```

-continued

```
Val Pro Thr Thr Asn Leu Tyr Ser Ala Thr Asp Glu Ile Val Gln Pro
            180                 185                 190

Gln Val Ser Asn Ser Pro Leu Asp Ser Ser Tyr Leu Phe Asn Gly Lys
        195                 200                 205

Asn Val Gln Ala Gln Ala Val Cys Gly Pro Leu Phe Val Ile Asp His
210                 215                 220

Ala Gly Ser Leu Thr Ser Gln Phe Ser Tyr Val Val Gly Arg Ser Ala
225                 230                 235                 240

Leu Arg Ser Thr Thr Gly Gln Ala Arg Ser Ala Asp Tyr Gly Ile Thr
                245                 250                 255

Asp Cys Asn Pro Leu Pro Ala Asn Asp Leu Thr Pro Glu Gln Lys Val
            260                 265                 270

Ala Ala Ala Ala Leu Leu Ala Pro Ala Ala Ile Val Ala Gly
        275                 280                 285

Pro Lys Gln Asn Cys Glu Pro Asp Leu Met Pro Tyr Ala Arg Pro Phe
            290                 295                 300

Ala Val Gly Lys Arg Thr Cys Ser Gly Ile Val Thr Pro
305                 310                 315

<210> SEQ ID NO 7
<211> LENGTH: 294
<212> TYPE: PRT
<213> ORGANISM: Burkholderia ambifaria

<400> SEQUENCE: 7

Met Glu Thr Asn Val Thr Ala Ala Pro Ser Asp His Pro Val Phe
1               5                   10                  15

Val Leu Val His Gly Ala Trp His Gly Ala Trp Cys Tyr Ala His Val
            20                  25                  30

Ala Ala Ala Leu Ala Glu Arg Gly Tyr Leu Ser Ile Ala Arg Asp Leu
        35                  40                  45

Pro Ala His Gly Ile Asn Ala Arg Phe Pro Ala Ser Tyr Leu Glu Arg
    50                  55                  60

Pro Leu Asp Lys Asp Ala Phe Gly Ala Glu Pro Ser Pro Val Ala Asn
65                  70                  75                  80

Thr Thr Leu Asp Asp Tyr Ala Thr Gln Val Met Glu Ala Val Asp Asp
                85                  90                  95

Ala Tyr Ala Leu Gly Arg Gly Lys Val Val Leu Val Gly His Ser Met
            100                 105                 110

Gly Gly Leu Ala Ile Thr Ala Ala Ala Glu Arg Ala Pro Glu Lys Ile
        115                 120                 125

Ala Lys Ile Val Tyr Leu Ala Ala Phe Met Pro Ala Ser Gly Val Pro
    130                 135                 140

Gly Leu Asp Tyr Val Arg Ala Pro Glu Asn Lys Gly Glu Met Leu Ala
145                 150                 155                 160

Pro Leu Met Leu Ala Ser Pro Arg Val Ala Gly Ala Leu Arg Ile Asp
                165                 170                 175

Pro Arg Ser Gly Asp Ala Ala Tyr Arg Ala Met Ala Lys Arg Ala Leu
            180                 185                 190

Tyr Asp Asp Ala Ala Gln Ala Asp Phe Glu Ala Met Ala Asn Leu Met
        195                 200                 205

Thr Cys Asp Val Pro Ala Ala Pro Phe Ala Thr Ala Ile Pro Thr Thr
    210                 215                 220

Ala Ala Arg Trp Gly Ala Ile Asp Arg His Tyr Ile Lys Cys Leu Glu
```

-continued

```
            225                 230                 235                 240
Asp Arg Val Ile Leu Pro Ala Leu Gln Gln Arg Phe Ile Asp Glu Ala
                245                 250                 255

Asp Ala Phe Val Pro Gly Asn Pro Thr His Val His Gln Leu Asp Ser
            260                 265                 270

Ser His Ser Pro Phe Val Ser Gln Pro Ala Val Leu Ala Gly Val Leu
        275                 280                 285

Val Asp Ile Ala Lys Ser
        290

<210> SEQ ID NO 8
<211> LENGTH: 311
<212> TYPE: PRT
<213> ORGANISM: Burkholderia cenocepacia

<400> SEQUENCE: 8

Met Ala Ala Gly Ser Ser Lys Met Thr Pro Phe Ser Lys Asn Thr Asp
1               5                   10                  15

Thr Met Glu Thr Asn Asp Asn Ala Thr Pro Gln Ser Asp His Pro Val
            20                  25                  30

Phe Val Leu Val His Gly Ala Trp His Gly Ala Trp Cys Tyr Ala His
        35                  40                  45

Val Ala Ala Ala Leu Ala Ala Arg Gly Tyr Leu Ser Ile Ala Arg Asp
    50                  55                  60

Leu Pro Ala His Gly Ile His Ala Arg Phe Pro Ala Ser Tyr Leu Ala
65                  70                  75                  80

Arg Pro Leu Asp Lys Asp Ala Phe Gly Ala Glu Pro Ser Pro Val Ala
                85                  90                  95

Asn Thr Thr Leu Asp Asp Tyr Ala Thr Gln Val Met Gln Ala Val Asp
            100                 105                 110

Asp Ala Tyr Ala Leu Gly Arg Gly Lys Val Val Leu Val Gly His Ser
        115                 120                 125

Met Gly Gly Leu Ala Ile Thr Ala Ala Ala Glu Arg Ala Pro Glu Lys
    130                 135                 140

Ile Ala Lys Ile Val Tyr Leu Ala Ala Phe Met Pro Ala Ser Gly Val
145                 150                 155                 160

Pro Gly Leu Asp Tyr Val Arg Ala Pro Glu Asn Lys Gly Glu Leu Leu
                165                 170                 175

Gly Pro Leu Met Leu Ala Ser Pro Arg Val Ala Gly Ala Leu Arg Val
            180                 185                 190

Asp Pro His Ser Gly Asp Ala Ala Tyr Arg Glu Leu Met Lys Arg Ala
        195                 200                 205

Leu Tyr Glu Asp Val Pro Gln Ala Asp Phe Asp Ala Val Ala Asn Leu
    210                 215                 220

Met Ser Cys Asp Val Pro Ala Ala Pro Phe Ala Thr Ala Ile Pro Thr
225                 230                 235                 240

Thr Ala Ala Arg Trp Gly Ala Ile Asp Arg His Tyr Val Lys Cys Leu
                245                 250                 255

Gln Asp Arg Val Ile Leu Pro Ala Leu Gln Gln Arg Phe Ile Asp Glu
            260                 265                 270

Ala Asp Ala Phe Ala Pro Gly Asn Pro Thr His Val His Gln Leu Asp
        275                 280                 285

Ser Ser His Ser Pro Phe Val Ser Gln Pro Ala Val Leu Ala Gly Val
    290                 295                 300
```

```
Leu Ala Asp Ile Ala Lys Ser
305                 310
```

<210> SEQ ID NO 9
<211> LENGTH: 294
<212> TYPE: PRT
<213> ORGANISM: Burkhholderia cenocepacia

<400> SEQUENCE: 9

```
Met Glu Thr Asn Asp Thr Ala Thr Pro Gln Ser Asp His Pro Ile Phe
1               5                   10                  15

Val Leu Val His Gly Ala Trp His Gly Ala Trp Cys Tyr Ala His Val
            20                  25                  30

Ala Ala Ala Leu Ala Ala Arg Gly Tyr Leu Ser Ile Ala Arg Asp Leu
        35                  40                  45

Pro Ala His Gly Ile His Ala Arg Phe Pro Ala Ser Tyr Leu Ala Arg
    50                  55                  60

Pro Leu Asp Lys Asp Ala Phe Gly Ala Glu Pro Ser Pro Val Ala Asn
65                  70                  75                  80

Thr Thr Leu Asp Asp Tyr Ala Thr Gln Val Met Gln Ala Val Asp Asp
                85                  90                  95

Ala Tyr Ala Leu Gly Arg Gly Lys Val Val Leu Val Gly His Ser Met
            100                 105                 110

Gly Gly Leu Ala Ile Thr Ala Ala Ala Glu Arg Ala Pro Glu Lys Ile
        115                 120                 125

Ala Lys Ile Val Tyr Leu Ala Ala Phe Met Pro Ala Ser Gly Val Pro
    130                 135                 140

Gly Leu Asp Tyr Val Arg Ala Pro Glu Asn Lys Gly Glu Leu Leu Gly
145                 150                 155                 160

Pro Leu Met Leu Ala Ser Pro Arg Val Ala Gly Ala Leu Arg Val Asp
                165                 170                 175

Pro Arg Ser Gly Asp Ala Ala Tyr Arg Glu Leu Met Lys Arg Ala Leu
            180                 185                 190

Tyr Glu Asp Val Pro Gln Pro Asp Phe Asp Ala Val Ala Asn Leu Met
        195                 200                 205

Ser Cys Asp Val Pro Ala Ala Pro Phe Ala Thr Ala Ile Pro Thr Thr
    210                 215                 220

Ala Ala Arg Trp Gly Ala Ile Asp Arg His Tyr Ile Lys Cys Leu Gln
225                 230                 235                 240

Asp Arg Val Ile Leu Pro Ala Leu Gln Gln Arg Phe Ile Asp Glu Ala
                245                 250                 255

Asp Ala Phe Ala Pro Gly Asn Pro Thr His Val His Gln Leu Asp Ser
            260                 265                 270

Ser His Ser Pro Phe Val Ser Gln Pro Ala Val Leu Ala Gly Val Leu
        275                 280                 285

Ala Asp Ile Ala Lys Ser
    290
```

<210> SEQ ID NO 10
<211> LENGTH: 294
<212> TYPE: PRT
<213> ORGANISM: Burkholderia cenocepacia

<400> SEQUENCE: 10

```
Met Glu Thr Asn Asp Thr Ala Thr Pro Gln Ser Asp His Pro Val Phe
1               5                   10                  15
```

```
Val Leu Val His Gly Ala Trp His Gly Ala Trp Cys Tyr Ala His Val
            20                  25                  30

Ala Ala Ala Leu Ala Ala Arg Gly Tyr Leu Ser Ile Ala Arg Asp Leu
        35                  40                  45

Pro Ala His Gly Ile His Ala Arg Phe Pro Ala Ser Tyr Leu Ala Arg
    50                  55                  60

Pro Leu Asp Lys Asp Ala Phe Gly Ala Glu Pro Ser Pro Val Ala Asn
65                  70                  75                  80

Thr Thr Leu Asp Asp Tyr Ala Thr Gln Val Met Gln Ala Val Asp Asp
                85                  90                  95

Ala Tyr Ala Leu Gly Arg Gly Lys Val Val Leu Val Gly His Ser Met
            100                 105                 110

Gly Gly Leu Ala Ile Thr Ala Ala Glu Arg Ala Pro Glu Lys Ile
        115                 120                 125

Ala Lys Ile Val Tyr Leu Ala Ala Phe Met Pro Ala Ser Gly Val Pro
    130                 135                 140

Gly Leu Asp Tyr Val Arg Ala Pro Glu Asn Lys Gly Glu Leu Leu Gly
145                 150                 155                 160

Pro Leu Met Leu Ala Ser Pro Arg Val Ala Gly Ala Leu Arg Val Asp
                165                 170                 175

Pro His Ser Gly Asp Ala Ala Tyr Arg Glu Leu Met Lys Arg Ala Leu
            180                 185                 190

Tyr Glu Asp Val Pro Gln Ala Asp Phe Asp Ala Val Ala Asn Leu Met
        195                 200                 205

Ser Cys Asp Val Pro Ala Ala Pro Phe Ala Thr Ala Ile Pro Thr Thr
210                 215                 220

Ala Ala Arg Trp Gly Ala Ile Asp Arg His Tyr Ile Lys Cys Leu Gln
225                 230                 235                 240

Asp Arg Val Ile Leu Pro Ala Leu Gln Gln Arg Phe Ile Asp Glu Ala
                245                 250                 255

Asp Ala Phe Ser Pro Gly Asn Pro Thr His Val His Gln Leu Asp Ser
            260                 265                 270

Ser His Ser Pro Phe Val Ser Gln Pro Ala Val Leu Ala Gly Val Leu
        275                 280                 285

Ser Gly Ile Ala Lys Ser
        290

<210> SEQ ID NO 11
<211> LENGTH: 294
<212> TYPE: PRT
<213> ORGANISM: Burkholderia cenocepacia

<400> SEQUENCE: 11

Met Glu Thr Asn Asp Asn Ala Thr Pro G

Ala Tyr Ala Leu Gly Arg Gly Lys Val Val Leu Val Gly His Ser Met
            100                 105                 110

Gly Gly Leu Ala Ile Thr Ala Ala Glu Arg Ala Pro Glu Lys Ile
        115                 120                 125

Ala Lys Ile Val Tyr Leu Ala Ala Phe Met Pro Ala Ser Gly Val Pro
    130                 135                 140

Gly Leu Asp Tyr Val Arg Ala Pro Glu Asn Lys Gly Glu Leu Leu Gly
145                 150                 155                 160

Pro Leu Met Leu Ala Ser Pro Arg Val Ala Gly Ala Leu Arg Val Asp
                165                 170                 175

Pro His Ser Gly Asp Ala Ala Tyr Arg Glu Leu Met Lys Arg Ala Leu
            180                 185                 190

Tyr Glu Asp Val Pro Gln Ala Asp Phe Asp Ala Val Ala Asn Leu Met
        195                 200                 205

Ser Cys Asp Val Pro Ala Ala Pro Phe Ala Thr Ala Ile Pro Thr Thr
    210                 215                 220

Ala Ala Arg Trp Gly Ala Ile Asp Arg His Tyr Val Lys Cys Leu Gln
225                 230                 235                 240

Asp Arg Val Ile Leu Pro Ala Leu Gln Gln Arg Phe Ile Asp Glu Ala
                245                 250                 255

Asp Ala Phe Ala Pro Gly Asn Pro Thr His Val His Gln Leu Asp Ser
            260                 265                 270

Ser His Ser Pro Phe Val Ser Gln Pro Ala Val Leu Ala Gly Val Leu
        275                 280                 285

Ala Asp Ile Ala Lys Ser
    290

<210> SEQ ID NO 12
<211> LENGTH: 294
<212> TYPE: PRT
<213> ORGANISM: Burkholderia cepacia

<400> SEQUENCE: 12

Met Glu Thr Asn Val Thr Ala Ala Pro Ser Asp His Pro Val Phe
1               5                   10                  15

Val Leu Val His Gly Ala Trp His Gly Ala Trp Cys Tyr Ala His Val
                20                  25                  30

Ala Ala Ala Leu Ala Glu Arg Gly Tyr Leu Ser Ile Ala Arg Asp Leu
            35                  40                  45

Pro Ala His Gly Ile Asn Ala Arg Phe Pro Ala Ser Tyr Leu Glu Arg
50 55 60

Pro Leu Asp Lys Asp Ala Phe Gly Ala Glu Pro Ser Pro Val Ala Asn
65 70 75 80

Thr Thr Leu Asp Asp Tyr Ala Thr Gln Val Met Glu Ala Val Asp Asp
85 90 95

Ala Tyr Ala Leu Gly His Gly Lys Val Val Leu Val Gly His Ser Met
100 105 110

Gly Gly Leu Ala Ile Thr Ala Ala Ala Glu Arg Ala Pro Glu Lys Ile
115 120 125

Ala Lys Ile Val Tyr Leu Ala Ala Phe Met Pro Ala Ser Gly Val Pro
130 135 140

Gly Leu Asp Tyr Val Arg Ala Pro Glu Asn Lys Gly Glu Met Leu Ala
145 150 155 160

Pro Leu Met Leu Ala Ser Pro Arg Val Ala Gly Ala Leu Arg Ile Asp

```
                    165                 170                 175
Pro Arg Ser Gly Asp Ala Ala Tyr Arg Ala Leu Ala Lys Arg Ala Leu
                180                 185                 190

Tyr Asp Asp Ala Ala Gln Ala Asp Phe Glu Ala Met Ala Asn Leu Met
            195                 200                 205

Thr Cys Asp Val Pro Ala Ala Pro Phe Ala Thr Ala Ile Pro Thr Thr
        210                 215                 220

Ala Ala Arg Trp Gly Ala Ile Asp Arg His Tyr Ile Lys Cys Leu Glu
225                 230                 235                 240

Asp Arg Val Ile Leu Pro Ala Leu Gln Gln Arg Phe Ile Asp Glu Ala
                245                 250                 255

Asp Ala Phe Val Pro Gly Asn Pro Thr His Val His Gln Leu Asp Thr
            260                 265                 270

Ser His Ser Pro Phe Val Ser Gln Pro Ala Val Leu Ala Ala Val Leu
        275                 280                 285

Val Asp Ile Ala Lys Ser
        290

<210> SEQ ID NO 13
<211> LENGTH: 294
<212> TYPE: PRT
<213> ORGANISM: Burkholderia dolosa

<400> S

Asp Arg Val Ile Leu Pro Ala Leu Gln Gln Arg Phe Ile Asp Glu Ala
                245                 250                 255

Asp Ala Phe Ala Pro Gly Asn Pro Thr His Val His Gln Leu Asp Ser
            260                 265                 270

Ser His Ser Pro Phe Val Ser Gln Pro Ala Val Leu Ala Gly Val Leu
        275                 280                 285

Ala Asp Ile Ala Lys Ser
    290

<210> SEQ ID NO 14
<211> LENGTH: 281
<212> TYPE: PRT
<213> ORGANISM: Burkholderia mallei

<400> SEQUENCE: 14

Met Pro Phe Val Leu Val His Gly Ala Trp His Gly Ala Trp Ala Tyr
1               5                   10                  15

Glu Arg Val Ile Pro Ala Leu Ala Ala His Gly His Ala Ala Val Ala
            20                  25                  30

Arg Asp Leu Pro Ala His Gly Val Asn Ala Arg Phe Pro Ala Ser Phe
        35                  40                  45

Ala Lys Arg Pro Leu Asp Ala Ala Phe Ala Ser Glu Pro Ser Pro
    50                  55                  60

Val Ala Gly Thr Thr Leu Asp Asp Tyr Val Asp His Val Leu Arg Thr
65                  70                  75                  80

Val Asp Gln Ala Arg Ala Leu Gly His Glu Arg Val Val Leu Val Gly
                85                  90                  95

His Ser Met Gly Gly Leu Ala Ile Thr Met Ala Ala Glu Arg Ala Pro
            100                 105                 110

Glu Lys Ile Ala Lys Leu Val Tyr Leu Ala Ala Phe Met Pro Thr Ala
        115                 120                 125

Gly Thr Lys Gly Leu Asp Tyr Val Arg Ala Pro Glu Asn Arg Gly Glu
    130                 135                 140

Met Leu Gly Pro Leu Met Met Ala Ser Pro Lys Ala Thr Gly Ala Leu
145                 150                 155                 160

Arg Met Asp Pro Arg Ser Asp Pro Ala Tyr Arg Ala Ala Ala Lys
                165                 170                 175

Arg Ala Leu Cys Asp Asp Ala Ser Asp Ala Asp His Ala Ala Val Gly
            180                 185                 190

His Leu Leu Gly Cys Asp Val Pro Ala Ala Pro Phe Ala Ala Arg Ile
        195                 200                 205

Glu Thr Thr Ala Ala Arg Trp Gly Ala Leu Glu Arg His Tyr Ile Lys
    210                 215                 220

Cys Leu Arg Asp Lys Val Leu Leu Pro Ala Leu Gln Gln Arg Phe Ile
225                 230                 235                 240

Asp Glu Ala Asp Ala Leu Ala Pro Gly Asn Arg Thr His Val His Thr
                245                 250                 255

Leu Asp Ser Ser His Ser Pro Phe Ile Ala His Ala Gly Ala Val Ala
            260                 265                 270

Asp Thr Leu Ala Ala Ile Ala Arg Gly
        275                 280

<210> SEQ ID NO 15
<211> LENGTH: 336
<212> TYPE: PRT
<213> ORGANISM: Burkholderia mallei

<400> SEQUENCE: 15

```
Met Gly His Asp Arg Thr Pro Arg His Arg Asp Ser Ser Leu Arg Trp
1               5                   10                  15

Arg Arg Leu Ala Ser Arg Pro Ala Ile Arg Thr Met Thr Asp Arg Gln
            20                  25                  30

Glu Thr Asp Leu Pro Thr Glu Pro Arg Asp Thr Val Ala Glu Arg Arg
        35                  40                  45

Glu Pro Ala Ala Ser Ser Leu Pro Phe Val Leu Val His Gly Ala
    50                  55                  60

Trp His Gly Ala Trp Ala Tyr Glu Arg Val Ile Pro Ala Leu Ala Ala
65              70                  75                  80

His Gly His Ala Ala Val Ala Arg Asp Leu Pro Ala His Gly Val Asn
                85                  90                  95

Ala Arg Phe Pro Ala Ser Phe Ala Lys Arg Pro Leu Asp Ala Ala Ala
            100                 105                 110

Phe Ala Ser Glu Pro Ser Pro Val Ala Gly Thr Thr Leu Asp Asp Tyr
        115                 120                 125

Val Asp His Val Leu Arg Thr Val Asp Gln Ala Arg Ala Leu Gly His
    130                 135                 140

Glu Arg Val Val Leu Val Gly His Ser Met Gly Gly Leu Ala Ile Thr
145                 150                 155                 160

Met Ala Ala Glu Arg Ala Pro Glu Lys Ile Ala Lys Leu Val Tyr Leu
                165                 170                 175

Ala Ala Phe Met Pro Thr Ala Gly Thr Lys Gly Leu Asp Tyr Val Arg
            180                 185                 190

Ala Pro Glu Asn Arg Gly Glu Met Leu Gly Pro Leu Met Met Ala Ser
        195                 200                 205

Pro Lys Ala Thr Gly Ala Leu Arg Met Asp Pro Arg Ser Asp Asp Pro
    210                 215                 220

Ala Tyr Arg Ala Ala Lys Arg Ala Leu Cys Asp Asp Ala Ser Asp
225                 230                 235                 240

Ala Asp His Ala Ala Val Gly His Leu Leu Gly Cys Asp Val Pro Ala
                245                 250                 255

Ala Pro Phe Ala Ala Arg Ile Glu Thr Thr Ala Ala Arg Trp Gly Ala
            260                 265                 270

Leu Glu Arg His Tyr Ile Lys Cys Leu Arg Asp Lys Val Leu Leu Pro
        275                 280                 285

Ala Leu Gln Gln Arg Phe Ile Asp Glu Ala Asp Ala Leu Ala Pro Gly
    290                 295                 300

Asn Arg Thr His Val His Thr Leu Asp Ser Ser His Ser Pro Phe Ile
305                 310                 315                 320

Ala His Ala Gly Ala Val Ala Asp Thr Leu Ala Ala Ile Ala Arg Gly
                325                 330                 335

<210> SEQ ID NO 16
<211> LENGTH: 358
<212> TYPE: PRT
<213> ORGANISM: Burkholderia mallei

<400> SEQUENCE: 16

Met Thr Ile Pro Glu Thr Gln Ser Met Pro Gly Glu Ala Gly Pro Arg
1               5                   10                  15

Arg Ser Gly Asp Thr Val Met Gly His Asp Arg Thr Pro Arg His Arg
            20                  25                  30
```

```
Asp Ser Ser Leu Arg Trp Arg Arg Leu Ala Ser Arg Pro Ala Ile Arg
        35                  40                  45

Thr Met Thr Asp Arg Gln Glu Thr Asp Leu Pro Thr Glu Pro Arg Asp
    50                  55                  60

Thr Val Ala Glu Arg Arg Glu Pro Ala Ala Ser Ser Ser Leu Pro Phe
65                  70                  75                  80

Val Leu Val His Gly Ala Trp His Gly Ala Trp Ala Tyr Glu Arg Val
                85                  90                  95

Ile Pro Ala Leu Ala Ala His Gly His Ala Ala Val Ala Arg Asp Leu
            100                 105                 110

Pro Ala His Gly Val Asn Ala Arg Phe Pro Ala Ser Phe Ala Lys Arg
        115                 120                 125

Pro Leu Asp Ala Ala Ala Phe Ala Ser Glu Pro Ser Pro Val Ala Gly
    130                 135                 140

Thr Thr Leu Asp Asp Tyr Val Asp His Val Leu Arg Thr Val Asp Gln
145                 150                 155                 160

Ala Arg Ala Leu Gly His Glu Arg Val Val Leu Val Gly His Ser Met
                165                 170                 175

Gly Gly Leu Ala Ile Thr Met Ala Ala Glu Arg Ala Pro Glu Lys Ile
            180                 185                 190

Ala Lys Leu Val Tyr Leu Ala Ala Phe Met Pro Thr Ala Gly Thr Lys
        195                 200                 205

Gly Leu Asp Tyr Val Arg Ala Pro Glu Asn Arg Gly Glu Met Leu Gly
    210                 215                 220

Pro Leu Met Met Ala Ser Pro Lys Ala Thr Gly Ala Leu Arg Met Asp
225                 230                 235                 240

Pro Arg Ser Asp Asp Pro Ala Tyr Arg Ala Ala Lys Arg Ala Leu
                245                 250                 255

Cys Asp Asp Ala Ser Asp Ala Asp His Ala Ala Val Gly His Leu Leu
            260                 265                 270

Gly Cys Asp Val Pro Ala Ala Pro Phe Ala Ala Arg Ile Glu Thr Thr
        275                 280                 285

Ala Ala Arg Trp Gly Ala Leu Glu Arg His Tyr Ile Lys Cys Leu Arg
    290                 295                 300

Asp Lys Val Leu Leu Pro Ala Leu Gln Gln Arg Phe Ile Asp Glu Ala
305                 310                 315                 320

Asp Ala Leu Ala Pro Gly Asn Arg Thr His Val His Thr Leu Asp Ser
                325                 330                 335

Ser His Ser Pro Phe Ile Ala His Ala Gly Ala Val Ala Asp Thr Leu
            340                 345                 350

Ala Ala Ile Ala Arg Gly
        355

<210> SEQ ID NO 17
<211> LENGTH: 309
<212> TYPE: PRT
<213> ORGANISM: Burkholderia mallei

<400> SEQUENCE: 17

Met Thr Asp Arg Gln Glu Thr Asp Leu Pro Thr Glu Pro Arg Asp Thr
1               5                   10                  15

Val Ala Glu Arg Arg Glu Pro Ala Ala Ser Ser Ser Leu Pro Phe Val
            20                  25                  30

Leu Val His Gly Ala Trp His Gly Ala Trp Ala Tyr Glu Arg Val Ile
```

```
                    35                  40                  45
Pro Ala Leu Ala Ala His Gly His Ala Val Ala Arg Asp Leu Pro
                50                  55                  60
Ala His Gly Val Asn Ala Arg Phe Pro Ala Ser Phe Ala Lys Arg Pro
 65                 70                  75                  80
Leu Asp Ala Ala Ala Phe Ala Ser Glu Pro Ser Pro Val Ala Gly Thr
                85                  90                  95
Thr Leu Asp Asp Tyr Val Asp His Val Leu Arg Thr Val Asp Gln Ala
                100                 105                 110
Arg Ala Leu Gly His Glu Arg Val Val Leu Val Gly His Ser Met Gly
                115                 120                 125
Gly Leu Ala Ile Thr Met Ala Ala Glu Arg Ala Pro Glu Lys Ile Ala
                130                 135                 140
Lys Leu Val Tyr Leu Ala Ala Phe Met Pro Thr Ala Gly Thr Lys Gly
145                 150                 155                 160
Leu Asp Tyr Val Arg Ala Pro Glu Asn Arg Gly Glu Met Leu Gly Pro
                165                 170                 175
Leu Met Met Ala Ser Pro Lys Ala Thr Gly Ala Leu Arg Met Asp Pro
                180                 185                 190
Arg Ser Asp Asp Pro Ala Tyr Arg Ala Ala Lys Arg Ala Leu Cys
                195                 200                 205
Asp Asp Ala Ser Asp Ala Asp His Ala Ala Val Gly His Leu Leu Gly
                210                 215                 220
Cys Asp Val Pro Ala Ala Pro Phe Ala Ala Arg Ile Glu Thr Thr Ala
225                 230                 235                 240
Ala Arg Trp Gly Ala Leu Glu Arg His Tyr Ile Lys Cys Leu Arg Asp
                    245                 250                 255
Lys Val Leu Leu Pro Ala Leu Gln Gln Arg Phe Ile Asp Glu Ala Asp
                260                 265                 270
Ala Leu Ala Pro Gly Asn Arg Thr His Val His Thr Leu Asp Ser Ser
                275                 280                 285
His Ser Pro Phe Ile Ala His Ala Gly Ala Val Ala Asp Thr Leu Ala
                290                 295                 300
Ala Ile Ala Arg Gly
305

<210> SEQ ID NO 18
<211> LENGTH: 301
<212> TYPE: PRT
<213> ORGANISM: Burkholderia mallei

<400> SEQUENCE: 18

Met Pro Thr Glu Pro Arg Asp Thr Val Ala Glu Arg Arg Glu Pro Ala
 1               5                  10                  15
Ala Ser Ser Ser Leu Pro Phe Val Leu Val His Gly Ala Trp His Gly
                20                  25                  30
Ala Trp Ala Tyr Glu Arg Val Ile Pro Ala Leu Ala Ala His Gly His
                35                  40                  45
Ala Ala Val Ala Arg Asp Leu Pro Ala His Gly Val Asn Ala Arg Phe
                50                  55                  60
Pro Ala Ser Phe Ala Lys Arg Pro Leu Asp Ala Ala Phe Ala Ser
 65                 70                  75                  80
Glu Pro Ser Pro Val Ala Gly Thr Thr Leu Asp Asp Tyr Val Asp His
                85                  90                  95
```

-continued

```
Val Leu Arg Thr Val Asp Gln Ala Arg Ala Leu Gly His Glu Arg Val
            100                 105                 110

Val Leu Val Gly His Ser Met Gly Gly Leu Ala Ile Thr Met Ala Ala
        115                 120                 125

Glu Arg Ala Pro Glu Lys Ile Ala Lys Leu Val Tyr Leu Ala Ala Phe
    130                 135                 140

Met Pro Thr Ala Gly Thr Lys Gly Leu Asp Tyr Val Arg Ala Pro Glu
145                 150                 155                 160

Asn Arg Gly Glu Met Leu Gly Pro Leu Met Met Ala Ser Pro Lys Ala
                165                 170                 175

Thr Gly Ala Leu Arg Met Asp Pro Arg Ser Asp Asp Pro Ala Tyr Arg
            180                 185                 190

Ala Ala Ala Lys Arg Ala Leu Cys Asp Asp Ala Ser Asp Ala Asp His
        195                 200                 205

Ala Ala Val Gly His Leu Leu Gly Cys Asp Val Pro Ala Ala Pro Phe
    210                 215                 220

Ala Ala Arg Ile Glu Thr Thr Ala Ala Arg Trp Gly Ala Leu Glu Arg
225                 230                 235                 240

His Tyr Ile Lys Cys Leu Arg Asp Lys Val Leu Leu Pro Ala Leu Gln
                245                 250                 255

Gln Arg Phe Ile Asp Glu Ala Asp Ala Leu Ala Pro Gly Asn Arg Thr
            260                 265                 270

His Val His Thr Leu Asp Ser Ser His Ser Pro Phe Ile Ala His Ala
        275                 280                 285

Gly Ala Val Ala Asp Thr Leu Ala Ala Ile Ala Arg Gly
    290                 295                 300

<210> SEQ ID NO 19
<211> LENGTH: 294
<212> TYPE: PRT
<213> ORGANISM: Burkholderia multivorans

<400> SEQUENCE: 19

Met Glu Thr Asn Val Thr Ala Pro Ser Gln Ser Asp His Pro Val Phe
1               5                   10                  15

Val Leu Val His Gly Ala Trp His Gly Ala Trp Cys Phe Ala His Val
            20                  25                  30

Ala Ala Ala Leu Ala Ala Arg Gly His Leu Ser Ile Ala Arg Asp Leu
        35                  40                  45

Pro Ala His Gly Leu His Ala Arg Phe Pro Val Ser Tyr His Val Arg
    50                  55                  60

Pro Leu Asp Lys Asp Ala Phe Gly Ala Glu Pro Ser Pro Val Ala Asn
65                  70                  75                  80

Thr Thr Leu Asp Asp Tyr Ala Thr Gln Val Met Gln Ala Val Asp Asp
                85                  90                  95

Ala Tyr Ala Leu Gly Arg Gly Lys Val Ile Leu Val Gly His Ser Met
            100                 105                 110

Gly Gly Leu Ala Ile Thr Ala Ala Ala Glu Arg Ala Pro Asp Lys Ile
        115                 120                 125

Ala Lys Leu Val Tyr Leu Ala Ala Phe Met Pro Ala Ala Gly Val Pro
    130                 135                 140

Gly Leu Asp Tyr Val Arg Ala Pro Glu Asn Arg Gly Glu Leu Leu Gly
145                 150                 155                 160

Pro Leu Met Leu Ala Ser Pro Arg Val Ala Gly Ala Leu Arg Ile Asp
                165                 170                 175
```

```
Pro Arg Ser Gly Asp Ala Asp Tyr Arg Ala Thr Arg Arg Ala Leu
        180                 185                 190

Cys Asp Asp Val Pro Gln Ala Asp Phe Asp Ala Val Ala Asn Leu Met
            195                 200                 205

Ser Cys Asp Val Pro Ala Ala Pro Phe Ala Thr Ala Ile Pro Thr Thr
210                 215                 220

Ala Ala Arg Trp Gly Ala Ile Asp Arg His Tyr Ile Lys Cys Leu Gln
225                 230                 235                 240

Asp Arg Val Leu Leu Pro Ala Leu Gln Gln Arg Phe Ile Asp Glu Ala
            245                 250                 255

Asp Ala Phe Ala Pro Gly Asn Pro Thr His Val His Gln Leu Asp Ser
        260                 265                 270

Ser His Ser Pro Phe Met Ser Gln Pro Ala Val Leu Ala Gly Val Leu
    275                 280                 285

Ala Asp Ile Ala Lys His
    290

<210> SEQ ID NO 20
<211> LENGTH: 281
<212> TYPE: PRT
<213> ORGANISM: Burkholderia pseudomallei

<400> SEQUENCE: 20

Met Pro Phe Val Leu Val His Gly Ala Trp His Gly Ala Trp Ala Tyr
1               5                   10                  15

Glu Arg Val Ile Pro Ala Leu Ala Ala His Gly His Ala Ala Val Ala
            20                  25                  30

Arg Asp Leu Pro Ala His Gly Val Asn Ala Arg Phe Pro Ala Ser Phe
        35                  40                  45

Ala Lys Arg Pro Leu Asp Ala Ala Phe Ala Ser Glu Pro Ser Pro
50                  55                  60

Val Ala Gly Thr Thr Leu Asp Asp Tyr Val Asp His Val Leu Arg Thr
65                  70                  75                  80

Val Asp Gln Ala Arg Ala Leu Gly His Glu Arg Val Val Leu Val Gly
            85                  90                  95

His Ser Met Gly Gly Leu Ala Ile Thr Met Ala Ala Glu Arg Ala Pro
        100                 105                 110

Glu Lys Ile Ala Lys Leu Val Tyr Leu Ala Ala Phe Met Pro Thr Ala
    115                 120                 125

Gly Thr Lys Gly Leu Asp Tyr Val Arg Ala Pro Glu Asn Gln Gly Glu
130                 135                 140

Met Leu Gly Pro Leu Met Met Ala Ser Pro Lys Ala Thr Gly Ala Leu
145                 150                 155                 160

Arg Met Asp Pro Arg Ser Asp Pro Ala Tyr Arg Ala Ala Lys
            165                 170                 175

Arg Ala Leu Cys Asp Asp Ala Ser Asp Ala His Ala Ala Val Gly
        180                 185                 190

His Leu Leu Gly Cys Asp Val Pro Ala Ala Pro Phe Ala Ala Arg Ile
    195                 200                 205

Glu Thr Thr Ala Ala Arg Trp Gly Ala Leu Glu Arg His Tyr Ile Lys
210                 215                 220

Cys Leu Arg Asp Lys Val Leu Leu Pro Ala Leu Gln Gln Arg Phe Ile
225                 230                 235                 240

Asp Glu Ala Asp Ala Leu Ala Pro Gly Asn Arg Thr His Val His Thr
```

Leu Asp Ser Ser His Ser Pro Phe Ile Ala His Ala Gly Ala Val Ala
            260                 265                 270

Asp Thr Leu Ala Ala Ile Ala Arg Gly
        275                 280

<210> SEQ ID NO 21
<211> LENGTH: 281
<212> TYPE: PRT
<213> ORGANISM: Burkholderia pseudomallei

<400> SEQUENCE: 21

Met Pro Phe Val Leu Val His Gly Ala Trp His Gly Ala Trp Ala Tyr
1               5                   10                  15

Glu Arg Val Ile Pro Ala Leu Ala Ala His Gly His Ala Ala Val Ala
            20                  25                  30

Arg Asp Leu Pro Ala His Gly Val Asn Ala Arg Phe Pro Ala Ser Phe
        35                  40                  45

Ala Lys Arg Pro Leu Asp Ala Ala Phe Ala Ser Glu Pro Ser Pro
    50                  55                  60

Val Ala Gly Thr Thr Leu Asp Asp Tyr Val Asp His Val Leu His Thr
65                  70                  75                  80

Val Asp Gln Ala Arg Ala Leu Gly His Glu Arg Val Val Leu Val Gly
                85                  90                  95

His Ser Met Gly Gly Leu Ala Ile Thr Met Ala Ala Glu Arg Ala Pro
            100                 105                 110

Glu Lys Ile Ala Lys Leu Val Tyr Leu Ala Ala Phe Met Pro Thr Ala
        115                 120                 125

Gly Thr Lys Gly Leu Asp Tyr Val Arg Ala Pro Glu Asn Gln Gly Glu
    130                 135                 140

Met Leu Gly Pro Leu Met Met Ala Ser Pro Lys Ala Thr Gly Ala Leu
145                 150                 155                 160

Arg Met Asp Pro Arg Ser Asp Pro Ala Tyr Arg Ala Ala Ala Lys
                165                 170                 175

Arg Ala Leu Cys Asp Asp Ala Ser Asp Ala Asp His Ala Ala Val Gly
            180                 185                 190

His Leu Leu Gly Cys Asp Val Pro Ala Ala Pro Phe Ala Ala Arg Ile
        195                 200                 205

Glu Thr Thr Ala Ala Arg Trp Gly Ala Leu Glu Arg His Tyr Ile Lys
    210                 215                 220

Cys Leu Arg Asp Lys Val Leu Leu Pro Ala Leu Gln Gln Arg Phe Ile
225                 230                 235                 240

Asp Glu Ala Asp Ala Leu Ala Pro Gly Asn Arg Thr His Val His Thr
                245                 250                 255

Leu Asp Ser Ser His Ser Pro Phe Ile Ala His Ala Gly Ala Val Ala
            260                 265                 270

Asp Thr Leu Ala Ala Ile Ala Arg Gly
        275                 280

<210> SEQ ID NO 22
<211> LENGTH: 281
<212> TYPE: PRT
<213> ORGANISM: Burkholderia pseudomallei

<400> SEQUENCE: 22

Met Pro Phe Val Leu Val His Gly Ala Trp His Gly Ala Trp Ala Tyr

```
            1               5                   10                  15
        Glu Arg Val Ile Pro Ala Leu Ala Ala His Gly His Ala Ala Val Ala
                        20                  25                  30

Arg Asp Leu Pro Ala His Gly Val Asn Ala Arg Phe Pro Ala Ser Phe
                    35                  40                  45

Ala Lys Arg Pro Leu Asp Ala Ala Phe Ala Ser Glu Pro Ser Pro
                50                  55                  60

Val Ala Gly Thr Thr Leu Asp Asp Tyr Val Asp His Val Leu His Thr
        65                  70                  75                  80

Val Asp Gln Ala Arg Ala Leu Gly His Glu Arg Val Val Leu Val Gly
                        85                  90                  95

His Ser Met Gly Gly Leu Ala Ile Thr Met Ala Ala Glu Arg Ala Pro
                        100                 105                 110

Glu Lys Ile Ala Lys Leu Val Tyr Leu Ala Ala Phe Met Pro Thr Ala
                        115                 120                 125

Gly Thr Lys Gly Leu Asp Tyr Val Arg Ala Pro Glu Asn Arg Gly Glu
                    130                 135                 140

Met Leu Gly Pro Leu Met Met Ala Ser Pro Lys Ala Thr Gly Ala Leu
        145                 150                 155                 160

Arg Met Asp Pro Arg Ser Asp Pro Ala Tyr Arg Ala Ala Lys
                        165                 170                 175

Arg Ala Leu Cys Asp Asp Ala Ser Asp Ala Asp His Ala Ala Val Gly
                    180                 185                 190

His Leu Leu Gly Cys Asp Val Pro Ala Ala Pro Phe Ala Ala Arg Ile
                    195                 200                 205

Glu Thr Thr Ala Ala Arg Trp Gly Ala Leu Glu Arg His Tyr Ile Lys
                    210                 215                 220

Cys Leu Arg Asp Lys Val Leu Leu Pro Ala Leu Gln Gln Arg Phe Ile
        225                 230                 235                 240

Asp Glu Ala Asp Ala Leu Ala Pro Gly Asn Arg Thr His Val His Thr
                        245                 250                 255

Leu Asp Ser Ser His Ser Pro Phe Ile Ala His Ala Gly Ala Val Ala
                    260                 265                 270

Asp Thr Leu Ala Ala Ile Ala Arg Gly
                    275                 280

<210> SEQ ID NO 23
<211> LENGTH: 336
<212> TYPE: PRT
<213> ORGANISM: Burkholderia pseudomallei

<400> SEQUENCE: 23

Met Gly His Asp Arg Thr Pro Arg His Arg Asp Ser Ser Leu Arg Trp
        1               5                   10                  15

Arg Arg Leu Ala Ser Arg Pro Ala Ile Arg Thr Met Thr Asp Arg Gln
                        20                  25                  30

Glu Thr Asp Leu Pro Thr Glu Pro Arg Asp Thr Val Ala Glu Arg Arg
                    35                  40                  45

Glu Pro Ala Ala Ser Ser Leu Pro Phe Val Leu Val His Gly Ala
                50                  55                  60

Trp His Gly Ala Trp Ala Tyr Glu Arg Val Ile Pro Ala Leu Ala Ala
        65                  70                  75                  80

His Gly His Ala Ala Val Ala Arg Asp Leu Pro Ala His Gly Val Asn
                        85                  90                  95
```

```
Ala Arg Phe Pro Ala Ser Phe Ala Lys Arg Pro Leu Asp Ala Ala Ala
            100                 105                 110

Phe Ala Ser Glu Pro Ser Pro Val Ala Gly Thr Thr Leu Asp Asp Tyr
        115                 120                 125

Val Asp His Val Leu His Thr Val Asp Gln Ala Arg Ala Leu Gly His
    130                 135                 140

Glu Arg Val Val Leu Val Gly His Ser Met Gly Gly Leu Ala Ile Thr
145                 150                 155                 160

Met Ala Ala Glu Arg Ala Pro Glu Lys Ile Ala Lys Leu Val Tyr Leu
                165                 170                 175

Ala Ala Phe Met Pro Thr Ala Gly Thr Lys Gly Leu Asp Tyr Val Arg
            180                 185                 190

Ala Pro Glu Asn Gln Gly Glu Met Leu Gly Pro Leu Met Met Ala Ser
        195                 200                 205

Pro Lys Ala Thr Gly Ala Leu Arg Met Asp Pro Arg Ser Asp Asp Pro
    210                 215                 220

Ala Tyr Arg Ala Ala Lys Arg Ala Leu Cys Asp Asp Ala Ser Asp
225                 230                 235                 240

Ala Asp His Ala Ala Val Gly His Leu Leu Gly Cys Asp Val Pro Ala
                245                 250                 255

Ala Pro Phe Ala Ala Arg Ile Glu Thr Thr Ala Ala Arg Trp Gly Ala
            260                 265                 270

Leu Glu Arg His Tyr Ile Lys Cys Leu Arg Asp Lys Val Leu Leu Pro
        275                 280                 285

Ala Leu Gln Gln Arg Phe Ile Asp Glu Ala Asp Ala Leu Ala Pro Gly
    290                 295                 300

Asn Arg Thr His Val His Thr Leu Asp Ser Ser His Ser Pro Phe Ile
305                 310                 315                 320

Ala His Ala Gly Ala Val Ala Asp Thr Leu Ala Ala Ile Ala Arg Gly
                325                 330                 335

<210> SEQ ID NO 24
<211> LENGTH: 301
<212> TYPE: PRT
<213> ORGANISM: Burkholderia pseudomallei

<400> SEQUENCE: 24

Met Pro Thr Glu Pro Arg Asp Thr Val Ala Glu Arg Arg Glu Pro Ala
1               5                   10                  15

Ala Ser Ser Leu Pro Phe Val Leu Val His Gly Ala Trp His Gly
            20                  25                  30

Ala Trp Ala Tyr Glu Arg Val Ile Pro Ala Leu Ala Ala His Gly His
        35                  40                  45

Ala Ala Val Ala Arg Asp Leu Pro Ala His Gly Val Asn Ala Arg Phe
    50                  55                  60

Pro Ala Ser Phe Ala Lys Arg Pro Leu Asp Ala Ala Phe Ala Ser
65                  70                  75                  80

Glu Pro Ser Pro Val Ala Gly Thr Thr Leu Asp Asp Tyr Val Asp His
                85                  90                  95

Val Leu Arg Thr Val Asp Gln Ala Arg Ala Leu Gly His Glu Arg Val
            100                 105                 110

Val Leu Val Gly His Ser Met Gly Gly Leu Ala Ile Thr Met Ala Ala
        115                 120                 125

Glu Arg Ala Pro Glu Lys Ile Ala Lys Leu Val Tyr Leu Ala Ala Phe
    130                 135                 140
```

```
Met Pro Thr Ala Gly Thr Lys Gly Leu Asp Tyr Val Arg Ala Pro Glu
145                 150                 155                 160

Asn Gln Gly Glu Met Leu Gly Pro Leu Met Met Ala Ser Pro Lys Ala
                165                 170                 175

Thr Gly Ala Leu Arg Met Asp Pro Arg Ser Asp Pro Ala Tyr Arg
            180                 185                 190

Ala Ala Ala Lys Arg Ala Leu Cys Asp Asp Ala Ser Asp Ala Asp His
            195                 200                 205

Ala Ala Val Gly His Leu Leu Gly Cys Asp Val Pro Ala Ala Pro Phe
        210                 215                 220

Ala Ala Arg Ile Glu Thr Thr Ala Ala Arg Trp Gly Ala Leu Glu Arg
225                 230                 235                 240

His Tyr

```
                210                 215                 220
Ala Ala Arg Ile Glu Thr Thr Ala Ala Arg Trp Gly Ala Leu Glu Arg
225                 230                 235                 240

His Tyr Ile Lys Cys Leu Arg Asp Lys Val Leu Leu Pro Ala Leu Gln
                245                 250                 255

Gln Arg Phe Ile Asp Glu Ala Asp Ala Leu Ala Pro Gly Asn Arg Thr
                260                 265                 270

His Val His Thr Leu Asp Ser Ser His Ser Pro Phe Ile Ala His Ala
                275                 280                 285

Gly Ala Val Ala Asp Thr Leu Ala Ala Ile Ala Arg Gly
                290                 295                 300

<210> SEQ ID NO 26
<211> LENGTH: 301
<212> TYPE: PRT
<213> ORGANISM: Burkholderia pseudomallei

<400> SEQUENCE: 26

Met Pro Thr Glu Pro Arg Asp Ile Val Ala Glu Arg Glu Pro Ala
1               5                   10                  15

Ala Ser Ser Leu Pro Phe Val Leu Val His Gly Ala Trp His Gly
                20                  25                  30

Ala Trp Ala Tyr Glu Arg Val Ile Pro Ala Leu Ala Ala His Gly His
            35                  40                  45

Ala Ala Val Ala Arg Asp Leu Pro Ala His Gly Val Asn Ala Arg Phe
        50                  55                  60

Pro Ala Ser Phe Ala Lys Arg Pro Leu Asp Ala Ala Phe Ala Ser
65                  70                  75                  80

Glu Pro Ser Pro Val Ala Gly Thr Thr Leu Asp Asp Tyr Val Asp His
                85                  90                  95

Val Leu Arg Thr Val Asp Gln Ala Arg Ala Leu Gly His Glu Arg Val
                100                 105                 110

Val Leu Val Gly His Ser Met Gly Gly Leu Ala Ile Thr Met Ala Ala
                115                 120                 125

Glu Arg Ala Pro Glu Lys Ile Ala Lys Leu Val Tyr Leu Ala Ala Phe
                130                 135                 140

Met Pro Thr Ala Gly Thr Lys Gly Leu Asp Tyr Val Arg Ala Pro Glu
145                 150                 155                 160

Asn Arg Gly Glu Met Leu Gly Pro Leu Met Met Ala Ser Pro Lys Ala
                165                 170                 175

Thr Gly Ala Leu Arg Met Asp Pro Arg Ser Asp Pro Ala Tyr Arg
                180                 185                 190

Ala Ala Ala Lys Arg Ala Leu Cys Asp Asp Ala Ser Asp Ala Asp His
                195                 200                 205

Ala Ala Val Gly His Leu Leu Gly Cys Asp Val Pro Ala Ala Pro Phe
                210                 215                 220

Ala Ala Arg Ile Glu Thr Thr Ala Ala Arg Trp Gly Ala Leu Glu Arg
225                 230                 235                 240

His Tyr Ile Lys Cys Leu Arg Asp Lys Val Leu Leu Pro Ala Leu Gln
                245                 250                 255

Gln Arg Phe Ile Asp Glu Ala Asp Ala Leu Ala Pro Gly Asn Arg Thr
                260                 265                 270

His Val His Thr Leu Asp Ser Ser His Ser Pro Phe Ile Ala His Ala
                275                 280                 285
```

```
Gly Ala Val Ala Asp Thr Leu Ala Ala Ile Ala Arg Gly
    290                 295                 300
```

<210> SEQ ID NO 27
<211> LENGTH: 294
<212> TYPE: PRT
<213> ORGANISM: Burkholderia sp.

<400> SEQUENCE: 27

```
Met Glu Thr Asn Ala Ser Ala Thr Pro Gln Ser Asp His Pro Val Phe
1               5                   10                  15

Val Leu Val His Gly Ala Trp His Gly Ala Trp Ser Tyr Ala His Val
            20                  25                  30

Ala Ala Ala Leu Ala Ala Arg Gly His Leu Ser Ile Ala Arg Asp Leu
        35                  40                  45

Pro Ala His Gly Ile Asn Ala Arg Phe Pro Ala Ser Tyr Phe Ala Arg
    50                  55                  60

Pro Leu Asp Lys Asp Ala Phe Gly Ala Glu Pro Ser Pro Val Ala Asn
65                  70                  75                  80

Thr Thr Leu Asp Asp Tyr Ala Thr Gln Val Met Gln Ala Val Asp Asp
                85                  90                  95

Ala Tyr Ala Leu Gly His Gly Lys Val Val Leu Val Gly His Ser Met
            100                 105                 110

Gly Gly Leu Ala Ile Thr Ala Ala Glu Arg Ala Pro Glu Lys Ile
        115                 120                 125

Ala Lys Ile Val Tyr Leu Ala Ala Phe Met Pro Ala Ser Gly Val Pro
    130                 135                 140

Gly Leu Asp Tyr Val Arg Ala Pro Glu Asn Lys Gly Glu Met Leu Gly
145                 150                 155                 160

Pro Leu Met Leu Ala Ser Pro Arg Val Ala Gly Ala Leu Arg Ile Asp
                165                 170                 175

Pro Arg Ser Gly Asp Ala Ala Tyr Arg Asp Leu Ala Lys Arg Ala Leu
            180                 185                 190

Tyr Asp Asp Val Pro Gln Ala Asp Phe Glu Ala Val Ala Asn Leu Met
        195                 200                 205

Thr Cys Asp Val Pro Ala Ala Pro Phe Ala Thr Ala Ile Pro Thr Thr
    210                 215                 220

Ala Ala Arg Trp Gly Ala Ile Asp Arg His Tyr Ile Lys Cys Leu Gln
225                 230                 235                 240

Asp Arg Val Ile Leu Pro Ala Leu Gln Gln Arg Phe Ile Asp Glu Ala
                245                 250                 255

Asp Ala Phe Ala Pro Gly Asn Pro Thr His Val His Gln Leu Asp Ser
            260                 265                 270

Ser His Ser Pro Phe Met Ser Gln Pro Ala Val Leu Ala Gly Val Leu
        275                 280                 285

Ala Asp Ile Ala Lys Ser
    290
```

<210> SEQ ID NO 28
<211> LENGTH: 301
<212> TYPE: PRT
<213> ORGANISM: Burkholderia thailandensis

<400> SEQUENCE: 28

```
Met Pro Thr Glu Pro Arg Asp Thr Pro Ala Asp Arg Arg Ala Pro Ala
1               5                   10                  15
```

```
Ala Pro Ser Pro Leu Pro Phe Val Leu Val His Gly Ala Trp His Gly
             20                  25                  30

Ala Trp Ala Tyr Glu Arg Val Ile Pro Ala Leu Ala Ala His Gly His
         35                  40                  45

Ala Ala Val Ala Arg Asp Leu Pro Ala His Gly Ile Asn Ala Arg Phe
     50                  55                  60

Pro Ala Ser Phe Phe Glu Arg Pro Leu Asp Ala Ala Phe Ala Ser
 65                  70                  75                  80

Glu Pro Ser Pro Val Ala Gly Thr Thr Leu Asp Asp Tyr Val Asp His
                 85                  90                  95

Val Leu His Thr Ile Asp Gln Ala Arg Ala Leu Gly His Glu Arg Val
            100                 105                 110

Val Leu Val Gly His Ser Met Gly Gly Leu Ala Ile Thr Met Ala Ala
            115                 120                 125

Glu Arg Ala Pro Glu Lys Ile Ala Lys Ile Val Tyr Leu Ala Ala Phe
            130                 135                 140

Met Pro Thr Ala Gly Thr Lys Gly Leu Asp Tyr Val Arg Ala Pro Glu
145                 150                 155                 160

Asn Gln Gly Glu Met Leu Ala Pro Leu Met Met Ala Ser Pro Lys Ala
                165                 170                 175

Thr Gly Ala Leu Arg Met Asp Pro Arg Ser Glu Asp Pro Ala Tyr Arg
            180                 185                 190

Ala Ala Ala Lys Arg Ala Leu Cys Asp Asp Ala Asn Asp Ala Asp His
            195                 200                 205

Ala Ala Val Gly His Leu Leu Ser Cys Asp Thr Pro Ala Ala Pro Phe
210                 215                 220

Ala Ala Arg Ile Glu Thr Thr Ala Ala Arg Trp Gly Ala Ile Glu Arg
225                 230                 235                 240

His Tyr Ile Lys Cys Leu Arg Asp Arg Val Leu Leu Pro Ala Leu Gln
                245                 250                 255

Gln Arg Phe Ile Asp Glu Ala Asp Ala Leu Ala Pro Gly Asn Arg Thr
            260                 265                 270

His Val His Thr Leu Asp Ser Ser His Ser Pro Phe Ile Ala Gln Pro
            275                 280                 285

Gly Ala Leu Ala Asp Thr Leu Ala Ala Ile Ala Arg Gly
    290                 295                 300

<210> SEQ ID NO 29
<211> LENGTH: 294
<212> TYPE: PRT
<213> ORGANISM: Burkholderia vietnamensis

<400> SEQUENCE: 29

Met Glu Thr Asn Val Thr Ala Ala Gln Gln Ser Asp His Pro Val Phe
 1               5                  10                  15

Val Leu Val His Gly Ala Trp His Gly Ala Trp Ser Tyr Ala Pro Val
             20                  25                  30

Ala Ala Ala Leu Ala Arg Gly Tyr Leu

```
Ala Tyr Ala Leu Gly Arg Gly Lys Val Val Leu Val Gly His Ser Met
            100                 105                 110

Gly Gly Leu Ala Ile Thr Ala Ala Ala Glu Arg Ala Pro Glu Lys Ile
            115                 120                 125

Ala Lys Leu Val Tyr Leu Ala Ala Phe Met Pro Ala Ser Gly Val Pro
        130                 135                 140

Gly Leu Asp Tyr Val Arg Ala Pro Glu Asn His Gly Asp Met Leu Gly
145                 150                 155                 160

Ala Leu Met Leu Ala Ser Pro Arg Val Ala Gly Ala Leu Arg Ile Asp
                165                 170                 175

Pro Arg Ser Gly Asp Ala Ala Tyr Arg Ala Gln Leu Lys Gln Ala Leu
            180                 185                 190

Tyr Asp Asp Val Pro Gln Ala Asp Phe Asp Ala Val Ala Asn Leu Met
        195                 200                 205

Thr Cys Asp Val Pro Ala Ala Pro Phe Ala Thr Ala Ile Pro Thr Ser
        210                 215                 220

Ala Ala Arg Trp Gly Ala Ile Asp Arg His Tyr Ile Lys Cys Leu Ala
225                 230                 235                 240

Asp Arg Val Leu Leu Pro Ala Leu Gln Gln Arg Phe Ile Asp Glu Ala
                245                 250                 255

Asp Ala Phe Ala Pro Asp Asn Pro Thr His Val His Gln Leu Asp Ser
            260                 265                 270

Ser His Ser Pro Phe Met Ser Gln Pro Ala Val Leu Ala Gly Val Leu
        275                 280                 285

Ala Asp Ile Ala Lys Ser
        290

<210> SEQ ID NO 30
<211> LENGTH: 282
<212> TYPE: PRT
<213> ORGANISM: Mycobacterium smegmatis

<400> SEQUENCE: 30

Met Asn Asp Ser Arg Asn Ser Gly Thr Leu Ala Val Leu Val His Gly
1               5                   10                  15

Ala Trp His Ser Ser Leu His Trp Ala Ala Gln Arg Gly Leu Ala
            20                  25                  30

Arg Arg Gly Val Ala Ser Ile Ala Val Asp Leu Pro Gly His Gly Leu
            35                  40                  45

Asp Ala Pro Val Pro Ser Gly Tyr Leu Thr Ala Gly Gln Pro Gly Leu
        50                  55                  60

Glu Thr Glu Lys Ser Ala Leu Ala Asp Ile Thr Met Asp Asp Leu Ala
65                  70                  75                  80

Asp Ala Val Val Asp Ala Leu Ala Glu Val Arg Ser Arg Phe Ala Arg
                85                  90                  95

Val Leu Leu Val Ala His Ser Ala Gly Gly Pro Ala Ser Leu Ala
            100                 105                 110

Ala Glu Lys Ala Pro Glu Leu Val Asp His Leu Val Tyr Leu Ala Ala
        115                 120                 125

Phe Val Pro Ala Ala Arg Pro Arg Phe Thr Asp Tyr Ile Asn Ala Pro
        130                 135                 140

Glu Asn Ala Asp Val Val Ala Leu Pro Ile Phe Ser Asp Pro Ala Asn
145                 150                 155                 160

Leu Gly Ala His Arg Leu Asn Pro Leu Ser Ser Asp Ala Ile Glu Val
```

```
                165                 170                 175
Asp Ala Ile Arg Arg Ala Phe Leu Thr Asp Met Pro Pro Asp Ala Pro
            180                 185                 190

Glu Gly Trp Arg His Leu Leu His Pro Asp Glu Pro Tyr Ala Ser Leu
            195                 200                 205

Ser Ala Pro Val Pro Val Thr Pro Arg Arg Trp Gly Arg Ile Pro Arg
        210                 215                 220

Thr Tyr Ile Arg Leu Asp Gly Asp Arg Ala Leu Ala Pro Thr Thr Gln
225                 230                 235                 240

Asn Leu Met Ile Ala Glu Ala Asp Arg Leu Thr Pro Asp Asn Pro Phe
                245                 250                 255

Gly Val Arg Ser Leu Pro Gly Asp His Ser Pro Met Val His Arg Pro
            260                 265                 270

Gly Glu Leu Ala Asp Leu Leu Ala Gly Ile
            275                 280

<210> SEQ ID NO 31
<211> LENGTH: 294
<212> TYPE: PRT
<213> ORGANISM: Saccharopolyspora erythraea

<400> SEQUENCE: 31

Met Ile Asp Leu Val Thr His Thr Ser Pro Thr Phe Val Leu Val Thr
1               5                   10                  15

Gly Ser Gly Ala Thr Ser Phe Leu Trp Asn Pro Leu Val Thr Glu Ile
            20                  25                  30

Val Leu Arg Gly His Arg Ala Leu Pro Val Glu Leu Pro Gly His Gly
        35                  40                  45

Phe Asp Ala Val Phe Pro Asp Gly Tyr Gly Ser Pro Gln Asp Thr Glu
    50                  55                  60

Val Phe Ala Gly Ala Pro Ser Pro Leu Ala Ala Leu Thr Leu Asp Asp
65                  70                  75                  80

Tyr Ala Asp His Ala Leu Gly Val Val Arg Arg Ala Ala Glu His Gly
                85                  90                  95

Pro Val Val Leu Val Gly His Ser Leu Gly Gly Ala Thr Val Thr Arg
            100                 105                 110

Val Ala Asn Ala Ala Pro Glu Leu Leu Ala His Val Val Tyr Leu Cys
        115                 120                 125

Ala Tyr Cys Cys Val Asp Glu Pro Ser Val Ala Ala Tyr Ala Pro Ser
    130                 135                 140

Ala Pro Ala Pro Gly Ser Pro Leu Glu Arg Ala Arg Arg Ile Ala Phe
145                 150                 155                 160

Leu Gly Asp Pro Arg Gly Thr Gly Val Met Arg Thr Asn Pro Arg Thr
                165                 170                 175

Gly Asp Pro Asp Val Leu Ala Val Gln His Glu Leu Leu Met Ala Asp
            180                 185                 190

Leu Asp Ala Ala Arg Val Pro Ala Val Leu Ala Tyr Ala Thr Gln Pro
        195                 200                 205

Asp Glu Pro Leu Arg Val Val Leu Ala Asp Ala Arg Val Asp Pro Ala
    210                 215                 220

Thr Trp Gly Arg Leu Pro Arg Thr Tyr Val Arg Thr Ser Arg Asp Glu
225                 230                 235                 240

Val Val Pro Pro Ala Leu Gln Asp Arg Met Ile Ala Glu Ala Asp Arg
                245                 250                 255
```

```
Arg Thr Pro Gly Asn Thr Phe Thr Ser His Thr Val Glu Ala Ser His
            260                 265                 270

Phe Ala Pro Leu Thr His Pro Ala Glu Ile Ala Asp Ile Leu Val Gly
        275                 280                 285

Ala Leu Arg Gln Glu Gly
    290
```

<210> SEQ ID NO 32
<211> LENGTH: 289
<212> TYPE: PRT
<213> ORGANISM: Saccharopolyspora erythraea

<400> SEQUENCE: 32

```
Met Thr Arg Pro Ser Ser Glu Thr Val Phe Leu Phe Val His Gly
1               5                   10                  15

Ala Trp His Ser Ser Leu His Trp Ala Glu Thr Leu Arg Ala Leu Ala
                20                  25                  30

Leu Gln Asp Leu Ala Gly Ile Ala Ile Asp Leu Pro Gly Ser Gly Leu
            35                  40                  45

Gly Ala Pro Val Pro Thr Gly Tyr Phe Gln Pro Gly Gln Pro Gly Leu
    50                  55                  60

Ala Thr Glu Lys Ser Ala Leu Ala Glu Val Thr Pro Ala Gln Ile Thr
65                  70                  75                  80

Asp Val Val Leu Asp Ala Leu Ala Ala Val Arg Thr Arg Phe Arg Asn
                85                  90                  95

Val Val Leu Val Ala His Ser Ala Gly Gly Ala Pro Ala Ser Ala Ala
            100                 105                 110

Ala Glu Arg Ala Pro Glu Leu Val Asp His Leu Val Tyr Leu Ser Ser
        115                 120                 125

Phe Val Pro Ala Gly Arg Pro Arg Phe Ser Asp Tyr Ile Glu Ala Glu
    130                 135                 140

Gln Asn Ala Gly Ala Val Arg Ile Pro Pro Leu Gly Asp Pro Ala Glu
145                 150                 155                 160

Leu Gly Ala Phe Arg Ile Asn Pro Leu Ser Pro Asp Pro Ala Asp Ile
                165                 170                 175

Asp Val Ile Arg Arg Ala Phe Leu Asn Asp Leu Pro Ala Thr Ala Pro
            180                 185                 190

Asp Thr Trp Arg Gln Phe Leu His Pro Asp Gln Pro Phe Thr Ser Val
        195                 200                 205

Thr Thr Pro Val Pro Val Thr Pro Glu Arg Trp Gly Arg Ile Ala Arg
    210                 215                 220

Thr Phe Ile Arg Leu Thr Asp Asp Leu Ala Leu Pro Leu Val Thr Gln
225                 230                 235                 240

Asp Leu Met Ile Asp Glu Ala Asn Gln Val Val Pro Asp Leu Pro Leu
                245                 250                 255

Gln Val Arg Thr Leu Pro Gly Gly His Ser Pro Phe Val Thr Arg Pro
            260                 265                 270

Ala Glu Leu Ala Ala Val Leu Ala Ser Val Ala Leu Gln Arg Thr Ala
        275                 280                 285

Arg
```

<210> SEQ ID NO 33
<211> LENGTH: 281
<212> TYPE: PRT
<213> ORGANISM: Saccharopolyspora erythraea

<400> SEQUENCE: 33

Met Ser His Thr Phe Val Leu Val His Gly Ser Asn Cys Asn Ser Phe
1               5                   10                  15

Thr Trp Ala Pro Met Gln Arg Glu Leu Ala Leu Leu Gly His Arg Ser
            20                  25                  30

Leu Ala Val Asp Leu Pro Gly His Gly Phe Ala Ala Gly Trp His Pro
        35                  40                  45

Ser Tyr Gln Ala Pro Gln Asp Pro Ala Ala Leu Ala Ser Ala Pro Ser
    50                  55                  60

Gly Gln Ala Gly Arg Thr Val Ala Glu Cys Val Glu His Val Val Glu
65                  70                  75                  80

Val Val Arg Arg Ala Ala Ala His Gly Pro Val Thr Leu Val Gly His
                85                  90                  95

Ser Arg Gly Gly Leu Thr Leu Thr Gly Val Gly Asn Ala Val Pro Glu
            100                 105                 110

Leu Val Asp Arg Leu Val Tyr Val Ser Ala Trp Cys Cys Val Asp Ser
        115                 120                 125

Thr Val Ala Glu Tyr Val Ala Ser Pro Glu Asn Ala Asp Ser Val Leu
    130                 135                 140

Gly Glu Ala Ala Gly Val Met Val Gly Asp Ile Ala Ala Leu Gly Ala
145                 150                 155                 160

Ile Arg Met Asn Trp Arg Thr Ala Asp Ala Gly Leu Leu Ala Thr Leu
                165                 170                 175

Lys Thr Ala Met Leu Ala Asp Gly Thr Asp Glu Glu Phe Leu Ala Phe
            180                 185                 190

Leu Asn Thr Leu Glu Pro Asp Glu Ser Leu Asp Ala Gly Gly Ile Gly
        195                 200                 205

Val Gln Ala Asp Ala Ala Thr Trp Gly Arg Val Pro Arg Ser Tyr Val
    210                 215                 220

Arg Leu Thr Arg Asp Arg Ser Leu Pro Val Ala Leu Gln Asp Arg Phe
225                 230                 235                 240

Ile Ala Glu Ala Asp Ala Leu Thr Pro Gly Asn Pro Phe Asp Val His
                245                 250                 255

Ser Val Glu Gly Ser His Val Gly Phe Leu Val His Pro Gln Glu Val
            260                 265                 270

Ala Gly Ile Leu Ala Glu Leu Ala Ala
        275                 280

<210> SEQ ID NO 34
<211> LENGTH: 308
<212> TYPE: PRT
<213> ORGANISM: Stigmatella aurantiaca

<400> SEQUENCE: 34

Met Asn Arg Arg Asn Leu Leu Lys Ser Ala Val Leu Thr Thr Ala Thr
1               5                   10                  15

Leu Pro Leu Ala Gly Gly Gly Ala Val Ala Leu Ala Ala Pro Arg Ala
            20                  25                  30

Ala Ser Lys Thr Phe Leu Leu Val His Gly Ala Trp His Asn Ala Leu
        35                  40                  45

His Trp Gly Arg Val Ala Gln His Leu Ser Ala Leu Gly His Arg Val
    50                  55                  60

Leu Ser Ile Asp Leu Pro Gly His Gly Leu Asn Ala Arg Phe Pro Ser
65                  70                  75                  80

```
Ala Tyr Ile Thr Gly Glu Trp Ala Lys Phe Ala Glu Pro Ser Pro
                85                  90                  95

Gln Arg Asp Ile Ser Leu Asp Gly Cys Ala Ser Ala Val Val Asp Ala
            100                 105                 110

Leu Arg Ala Leu Lys Gly Gly Pro Arg Pro Ile Leu Val Gly His Ser
            115                 120                 125

Met Gly Gly Thr Val Ile Thr Arg Val Gly Glu Leu Ala Pro Asp Gln
    130                 135                 140

Val Gly Arg Leu Val Tyr Leu Ser Ala Tyr Cys Pro Leu Arg Leu Lys
145                 150                 155                 160

Lys Pro Ser Ala Tyr Gly Ala Leu Pro Glu Ala Lys Thr Asp Gln Gly
                165                 170                 175

Ser Thr Leu Ile Ile Gly Asn Pro Ala Ala Leu Gly Ala Val Arg Ile
            180                 185                 190

Asn Pro Arg Gly Asn Ala Ser Tyr Leu Glu Ala Leu Arg Ser Ala Tyr
        195                 200                 205

Tyr Asn Asp Val Glu Met Arg Glu Phe Leu Pro Phe Ala Leu Ala Leu
    210                 215                 220

Thr Pro Asp Leu Pro Ala Ala Leu Trp Thr Ser Glu Val Val Ala Thr
225                 230                 235                 240

Arg Glu Arg Trp Gly Arg Ile Pro Arg Ser Tyr Ile Arg Cys Thr Gln
                245                 250                 255

Asp Arg Ala Leu Met Pro Gly Leu Gln Asp Leu Met Ile Arg Glu Ala
            260                 265                 270

Asp Ala Phe Thr Pro Thr Asn Thr Phe Glu Gln Lys Thr Leu Glu Thr
        275                 280                 285

Ser His Ser Pro Phe Ala Ser Gln Pro Ala Arg Leu Ala Glu Leu Leu
    290                 295                 300

Thr Ser Leu Arg
305

<210> SEQ ID NO 35
<211> LENGTH: 287
<212> TYPE: PRT
<213> ORGANISM: Streptomyces ambofaciens

<400> SEQUENCE: 35

Met Gln Pro Thr Phe Val Leu Val His Gly Ala Phe Ala Asn Ser Phe
1               5                   10                  15

Ser Phe Ala Pro Leu Gln Ala Glu Leu Gly Leu Leu Gly His Arg Ser
            20                  25                  30

Val Ala Val Asp Leu Pro Gly His Gly Phe Ala Ala Ser Tyr Ser His
        35                  40                  45

Ala Tyr Gln Ala Pro Gln Asp Ala Glu Gly Leu Ala Thr Ala Pro Gly
    50                  55                  60

Ser Leu Lys Gly Val Thr Leu Ala Asp Asn Ala Ala His Val Ile Gly
65                  70                  75                  80

Val Leu Glu Arg Ala Lys Glu His Gly Pro Val Ile Leu Val Ala His
                85                  90                  95

Ser Arg Gly Gly Ile Thr Ala Thr Ala Val Ala Asn Ala Arg Pro Asp
            100                 105                 110

Leu Ile Asp Arg Ile Val Tyr Val Ala Ala Trp Cys Pro Val Arg Leu
        115                 120                 125

Asp Val Asn Asp Tyr Tyr Ala Glu Pro Glu Met Ala Thr Val Asp Ala
    130                 135                 140
```

```
Ala Ser Val Gly Leu Ala Met Ala Gly Asn Pro Ala Glu Leu Gly Leu
145                 150                 155                 160

Leu Arg Val Asn Phe Arg Thr Ala Asp Gln Ala Leu Ala Ala Leu
            165                 170                 175

Lys Ala Ala Phe Leu Ala Asp Gly Thr Glu Glu Phe Leu Thr Phe
        180                 185                 190

Leu Asn Thr Phe Gln Pro Asp Glu Asn Leu Asp Val Gly Gly Ala Ala
            195                 200                 205

Asp Arg Ala Gln Ala Ala Thr Trp Gly Arg Val Pro Lys Thr Phe Val
210                 215                 220

Arg Leu Ala Asp Asp Ala Ser Met Pro Leu Val Met Gln Asp Arg Leu
225                 230                 235                 240

Ile Arg Glu Gly Asp Glu Leu Thr Pro Asp Asn Pro Tyr Asp Val Arg
                245                 250                 255

Thr Leu Gly Gly Ser His Leu Lys Trp Leu Val Asp Pro Ala Pro Ala
            260                 265                 270

Ala Arg Val Leu Gly Glu Leu Ser Ala Leu Thr Ala Gly Ala Ser
            275                 280                 285

<210> SEQ ID NO 36
<211> LENGTH: 327
<212> TYPE: PRT
<213> ORGANISM: Streptomyces coelicolor

<400> SEQUENCE: 36

Met Phe Met Thr Asp Asp Thr Asn Glu Glu Gly Glu Gly Ala Thr Arg
1               5                   10                  15

Arg Thr Ala Leu Arg Gly Leu Gly Leu Ala Val Gly Gly Met Ala Leu
            20                  25                  30

Ala Ala Gly Pro Gly Thr Ser Pro Ala Ala Ala Pro Arg Arg Arg
        35                  40                  45

Leu Val Thr Tyr Val Leu Val His Gly Thr His Ser Ala Gly Ala Phe
50                  55                  60

Trp Thr Pro Ile Ala Arg Glu Leu Gly Leu Arg Gly His Arg Val Val
65                  70                  75                  80

Met Val Asp Gln Pro Arg His Gly Ala Glu Ala Phe Val Ala Glu Ser
                85                  90                  95

Tyr Gln Arg Gln Asp Leu Ala Ala Met Ala Val Glu Pro Ser Pro Leu
            100                 105                 110

Lys Gly Leu Gly Leu Asp Asp Tyr Glu Ala Arg Val Ala Gly Ile Val
        115                 120                 125

Arg Arg Ala Ala Arg Asn Gly Pro Val Val Leu Val Gly His Ser Leu
130                 135                 140

Gly Gly Val Ser Val Ser Arg Val Gly Glu Ala Val Pro His Leu Leu
145                 150                 155                 160

His His Ile Cys Tyr Met Ala Ala Phe Cys Pro Ser Arg Val Leu Pro
                165                 170                 175

Thr Ala Asp Ala Cys Thr Ala Ala Pro Glu Asn Ala Asn Ala Val Ser
            180                 185                 190

Pro Val Glu Leu Thr Val Gly Asp Pro Asp Arg Leu Gly Val Leu Arg
        195                 200                 205

Leu Asn Phe Arg Thr Gly Val Ser Gly Glu Leu Ala Leu Leu Lys Glu
210                 215                 220

Met Ile Cys Ala Asp Tyr Pro Asp Ala Asp Phe Arg Arg Ile Leu Ala
```

```
                   225                 230                 235                 240

Gly Met Gln Thr Asp Glu Pro Val Ala Ala Tyr Ala Gly Arg Ala Val
                245                 250                 255

Gly Arg Ala Gly Arg Trp Gly Arg Ile Pro Arg Thr Tyr Leu Arg Phe
                260                 265                 270

Gly Arg Asp Arg Thr Ile Ala Thr Ala Leu Gln Asp Arg Val Ile Ala
                275                 280                 285

Glu Ala Asp Ala Ala Thr Pro Gly Asn Gly Phe Arg Val His Asp Phe
                290                 295                 300

Pro Glu Ala Ser His Val Gly Pro Leu Asp Pro Thr Pro Val Ala Asp
305                 310                 315                 320

Val Leu Asp Arg Leu Ala Gly
                325

<210> SEQ ID NO 37
<211> LENGTH: 388
<212> TYPE: PRT
<213> ORGANISM: Artificial sequence
<220> FEATURE:
<223> OTHER INFORMATION: deletion mutant EstB_Short4; derived from
      SEQ ID NO:3
<220> FEATURE:
<221> NAME/KEY: MISC_FEATURE
<223> OTHER INFORMATION: corresponds to EstB_N27, whereby amino acids
      317-319 (RGP) of EstB_N27 (SEQ ID NO:3) have been deleted

<400> SEQUENCE: 37

Met Thr Ala Ala Ser Leu Asp Pro Thr Ala Phe Ser Leu Asp Ala Ala
1               5                   10                  15

Leu Leu Ala Ala Arg Leu Asp Ala Val Phe Asp Gln Ala Leu Arg Glu
                20                  25                  30

Arg Arg Leu Val Gly Ala Val Ala Ile Val Ala Arg His Gly Glu Ile
                35                  40                  45

Leu Tyr Arg Arg Ala Gln Gly Leu Ala Asp Arg Glu Ala Gly Arg Pro
                50                  55                  60

Met Arg Glu Asp Thr Leu Phe Arg Leu Ala Ser Val Thr Lys Pro Ile
65                  70                  75                  80

Val Ala Leu Ala Val Leu Arg Leu Val Ala Arg Gly Glu Leu Ala Leu
                85                  90                  95

Asp Ala Pro Val Thr Arg Trp Leu Pro Glu Phe Arg Pro Arg Leu Ala
                100                 105                 110

Asp Gly Ser Glu Pro Leu Val Thr Ile His His Leu Leu Thr His Thr
                115                 120                 125

Ser Gly Leu Ser Tyr Trp Leu Leu Glu Gly Ala Gly Ser Val Tyr Asp
                130                 135                 140

Arg Leu Gly Ile Ser Asp Gly Ile Asp Leu Arg Asp Phe Asp Leu Asp
145                 150                 155                 160

Glu Asn Leu Arg Arg Leu Ala Ser Ala Pro Leu Ser Phe Ala Pro Gly
                165                 170                 175

Ser Gly Trp Gln Tyr Ser Leu Ala Leu Asp Val Leu Gly Ala Val Val
                180                 185                 190

Glu Arg Ala Thr Gly Gln Pro Leu Ala Ala Ala Val Asp Ala Leu Val
                195                 200                 205

Ala Gln Pro Leu Gly Met Arg Asp Cys Gly Phe Val Ser Ala Glu Pro
                210                 215                 220

Glu Arg Phe Ala Val Pro Tyr His Asp Gly Gln Pro Glu Pro Val Arg
225                 230                 235                 240
```

```
Met Arg Asp Gly Ile Glu Val Pro Leu Pro Gly Gly His Gly Ala Ala
                245                 250                 255

Val Arg Phe Ala Pro Ser Arg Val Phe Glu Pro Gly Ala Tyr Pro Ser
            260                 265                 270

Gly Gly Ala Gly Met Tyr Gly Ser Ala Asp Asp Val Leu Arg Ala Leu
        275                 280                 285

Glu Ala Ile Arg Ala Asn Pro Gly Phe Leu Pro Glu Thr Leu Ala Asp
    290                 295                 300

Ala Ala Arg Arg Asp Gln Val Gly Val Gly Ala Lys Thr Gly Trp Gly
305                 310                 315                 320

Phe Gly Tyr Leu Ser Ala Val Leu Asp Asp Pro Ala Ala Gly Thr
                325                 330                 335

Pro Gln His Ala Gly Thr Leu Gln Trp Gly Gly Val Tyr Gly His Ser
            340                 345                 350

Trp Phe Val Asp Arg Ala Leu Gly Leu Ser Val Leu Leu Thr Asn
        355                 360                 365

Thr Ala Tyr Glu Gly Met Ser Gly Pro Leu Thr Ile Ala Leu Arg Asp
    370                 375                 380

Ala Val Tyr Ala
385

<210> SEQ ID NO 38
<211> LENGTH: 388
<212> TYPE: PRT
<213> ORGANISM: Artificial sequence
<220> FEATURE:
<223> OTHER INFORMATION: EstB_N27 Short5; derived from SEQ ID NO:3
<220> FEATURE:
<221> NAME/KEY: MISC_FEATURE
<223> OTHER INFORMATION: amino acids 248-255 (PLPGGHGA) of SEQ ID NO:3
      have been replaced by SLGTT

<400> SEQUENCE: 38

Met Thr Ala Ala Ser Leu Asp Pro Thr Ala Phe Ser Leu Asp Ala Ala
1               5                   10                  15

Leu Leu Ala Ala Arg Leu Asp Ala Val Phe Asp Gln Ala Leu Arg Glu
            20                  25                  30

Arg Arg Leu Val Gly Ala Val Ala Ile Val Ala Arg His Gly Glu Ile
        35                  40                  45

Leu Tyr Arg Arg Ala Gln Gly Leu Ala Asp Arg Glu Ala Gly Arg Pro
    50                  55                  60

Met Arg Glu Asp Thr Leu Phe Arg Leu Ala Ser Val Thr Lys Pro Ile
65                  70                  75                  80

Val Ala Leu Ala Val Leu Arg Leu Val Ala Arg Gly Glu Leu Ala Leu
                85                  90                  95

Asp Ala Pro Val Thr Arg Trp Leu Pro Glu Phe Arg Pro Arg Leu Ala
            100                 105                 110

Asp Gly Ser Glu Pro Leu Val Thr Ile His His Leu Thr His Thr
        115                 120                 125

Ser Gly Leu Ser Tyr Trp Leu Leu Glu Gly Ala Gly Ser Val Tyr Asp
    130                 135                 140

Arg Leu Gly Ile Ser Asp Gly Ile Asp Leu Arg Asp Phe Asp Leu Asp
145                 150                 155                 160

Glu Asn Leu Arg Arg Leu Ala Ser Ala Pro Leu Ser Phe Ala Pro Gly
                165                 170                 175

Ser Gly Trp Gln Tyr Ser Leu Ala Leu Asp Val Leu Gly Ala Val Val
```

```
                 180                 185                 190

Glu Arg Ala Thr Gly Gln Pro Leu Ala Ala Val Asp Ala Leu Val
                195                 200                 205

Ala Gln Pro Leu Gly Met Arg Asp Cys Gly Phe Val Ser Ala Glu Pro
        210                 215                 220

Glu Arg Phe Ala Val Pro Tyr His Asp Gly Gln Pro Glu Pro Val Arg
    225                 230                 235                 240

Met Arg Asp Gly Ile Glu Val Ser Leu Gly Thr Thr Ala Val Arg Phe
                    245                 250                 255

Ala Pro Ser Arg Val Phe Glu Pro Gly Ala Tyr Pro Ser Gly Gly Ala
                260                 265                 270

Gly Met Tyr Gly Ser Ala Asp Val Leu Arg Ala Leu Glu Ala Ile
            275                 280                 285

Arg Ala Asn Pro Gly Phe Leu Pro Glu Thr Leu Ala Asp Ala Ala Arg
            290                 295                 300

Arg Asp Gln Val Gly Val Gly Ala Lys Thr Arg Gly Pro Gly Trp Gly
    305                 310                 315                 320

Phe Gly Tyr Leu Ser Ala Val Leu Asp Asp Pro Ala Ala Gly Thr
                325                 330                 335

Pro Gln His Ala Gly Thr Leu Gln Trp Gly Val Tyr Gly His Ser
            340                 345                 350

Trp Phe Val Asp Arg Ala Leu Gly Leu Ser Val Leu Leu Leu Thr Asn
            355                 360                 365

Thr Ala Tyr Glu Gly Met Ser Gly Pro Leu Thr Ile Ala Leu Arg Asp
            370                 375                 380

Ala Val Tyr Ala
    385

<210> SEQ ID NO 39
<211> LENGTH: 35
<212> TYPE: DNA
<213> ORGANISM: Artificial sequence
<220> FEATURE:
<223> OTHER INFORMATION: PCR-Primer
<220> FEATURE:
<221> NAME/KEY: misc_feature
<223> OTHER INFORMATION: introduces the amino acid exchange Phe138Val

<400> SEQUENCE: 39
gctgctcttg tatatcttgc tgcggtcatg cctgc                              35

<210> SEQ ID NO 40
<211> LENGTH: 35
<212> TYPE: DNA
<213> ORGANISM: Artificial sequence
<220> FEATURE:
<223> OTHER INFORMATION: PCR-Primer
<220> FEATURE:
<221> NAME/KEY: misc_feature
<223> OTHER INFORMATION: introduces the amino acid exchange Phe138Ala

<400> SEQUENCE: 40
gctgctcttg tatatcttgc tgcggccatg cctgc                              35

<210> SEQ ID NO 41
<211> LENGTH: 35
<212> TYPE: DNA
<213> ORGANISM: Artificial sequence
<220> FEATURE:
<223> OTHER INFORMATION: PCR-Primer
<220> FEATURE:
```

<221> NAME/KEY: misc_feature
<223> OTHER INFORMATION: introduces the amino acid exchange Glu154Ala

<400> SEQUENCE: 41
gtaagagcac cagcaaacca tggcgaaatg ctggc                                35

<210> SEQ ID NO 42
<211> LENGTH: 27
<212> TYPE: DNA
<213> ORGANISM: Artificial sequence
<220> FEATURE:
<223> OTHER INFORMATION: PCR-Primer
<220> FEATURE:
<221> NAME/KEY: misc_feature
<223> OTHER INFORMATION: introduces the amino acid exchange Leu163Ala

<400> SEQUENCE: 42
ctggcctcgg cgatctgcgc cagccct                                         27

<210> SEQ ID NO 43
<211> LENGTH: 25
<212> TYPE: DNA
<213> ORGANISM: Artificial sequence
<220> FEATURE:
<223> OTHER INFORMATION: PCR-Primer
<220> FEATURE:
<221> NAME/KEY: misc_feature
<223> OTHER INFORMATION: introduces the amino acid exchange Leu189Ala

<400> SEQUENCE: 43
cggcctatct cgccacggcg aagca                                           25

<210> SEQ ID NO 44
<211> LENGTH: 35
<212> TYPE: DNA
<213> ORGANISM: Artificial sequence
<220> FEATURE:
<223> OTHER INFORMATION: PCR-Primer
<220> FEATURE:
<221> NAME/KEY: misc_feature
<223> OTHER INFORMATION: introduces the amino acid exchange
      Leu189AlaLeu193Ala

<400> SEQUENCE: 44
gccacggcga agcaggcggc gttcgaggat gttga                                35

<210> SEQ ID NO 45
<211> LENGTH: 25
<212> TYPE: DNA
<213> ORGANISM: Artificial sequence
<220> FEATURE:
<223> OTHER INFORMATION: PCR-Primer
<220> FEATURE:
<221> NAME/KEY: misc_feature
<223> OTHER INFORMATION: introduces the amino acid exchange Leu193Ala

<400> SEQUENCE: 45
gcaggcggcg ttcgaggatg ttgac                                           25

<210> SEQ ID NO 46
<211> LENGTH: 30
<212> TYPE: DNA
<213> ORGANISM: Artificial sequence
<220> FEATURE:
<223> OTHER INFORMATION: PCR-Primer
<220> FEATURE:
<221> NAME/KEY: misc_feature
<223> OTHER INFORMATION: introduces the amino acid exchange Val150Ala

<400> SEQUENCE: 46
gtacctggtc ttgattacgc gagagctcct                                              30

<210> SEQ ID NO 47
<211> LENGTH: 25
<212> TYPE: DNA
<213> ORGANISM: Artificial sequence
<220> FEATURE:
<223> OTHER INFORMATION: PCR-Primer
<220> FEATURE:
<221> NAME/KEY: misc_feature
<223> OTHER INFORMATION: introduces the amino acid exchange Thr188Ser

<400> SEQUENCE: 47
gcctatctcg cctcgctgaa gcagg                                                   25

<210> SEQ ID NO 48
<211> LENGTH: 25
<212> TYPE: DNA
<213> ORGANISM: Artificial sequence
<220> FEATURE:
<223> OTHER INFORMATION: PCR-Primer
<220> FEATURE:
<221> NAME/KEY: misc_feature
<223> OTHER INFORMATION: introduces the amino acid exchange

<400> SEQUENCE: 48
cgaaatggcg gcctcgctga tctgc                                                   25

<210> SEQ ID NO 49
<211> LENGTH: 35
<212> TYPE: DNA
<213> ORGANISM: Artificial sequence
<220> FEATURE:
<223> OTHER INFORMATION: PCR-Primer
<220> FEATURE:
<221> NAME/KEY: misc_feature
<223> OTHER INFORMATION: introduces the amino acid exchanges
      Thr188AlaLeu189AlaLeu193Ala

<400> SEQUENCE: 49
tatctcgcct cggcgaagca ggcggcgttc gagga                                        35

<210> SEQ ID NO 50
<211> LENGTH: 1179
<212> TYPE: DNA
<213> ORGANISM: Burkholderia gladioli
<220> FEATURE:
<221> NAME/KEY: misc_feature
<223> OTHER INFORMATION: sequence coding for SEQ ID NO:1

<400> SEQUENCE: 50
atgaccgctg cctcgctcga cccgaccgct ttctccctcg atgccgcctc gctggccgcg 60
cgtctcgatg ccgtgttcga ccaggcgctg cgcgaacggc gcctggtcgg cgcggtggcg 120
atcgtcgcgc ggcacggcga gatcctgtat cgccgcgccc agggcctggc cgaccgagag 180
gcaggtcggc cgatgcgcga ggacacgctg ttccggctcg cttcggtgac caagccgatc 240
gtcgcgctgg cggtgctgcg gctggtggcg cgcggcgaac tcgcgctcga cgcgccggtc 300
acgcgctggt tgcccgaatt ccggccgcgg ctggccgacg gcagcgagcc gctcgtcacg 360
attcaccacc tgctcacgca cacgtcgggg ctcggctact ggctgctcga gggcgccggc 420
tccgtgtacg accggctcgg catctcggac ggcatcgacc tgcgcgactt cgatctcgac 480
gaaaacctgc gccgcctcgc ctcggcgccg ctgtccttcg cgccgggcag cggctggcag 540

```
tattcgctgg cgctcgacgt gctcggcgcg gtggtcgagc gcgccaccgg gcagccgctg      600
gccgcggcgg tggacgcgtt ggtcgcccag ccgctcggca tgcgcgattg cggtttcgtc      660
tcggcggagc ccgagcgctt cgccgtgcct taccacgacg gccagccgga gccggtgcgc      720
atgcgcgacg gcatcgaggt gccgctgccg gaaggccacg gcgcggccgt gcgtttcgcg      780
ccctcccgcg tgttcgagcc gggcgcctat ccctcgggcg gcgccggcat gtacggctcg      840
gccgacgacg tcctgcgcgc gctcgaggcg atccgcgcca atccggtttt cctgcccgag      900
acgctggccg acgcggcgcg ccgcgaccag gccggagtcg gcgccgagac gcgcggcccc      960
ggctggggct tcggctacct gagcgcggtg ctcgacgatc cggccgcggc cggcacccccg      1020 cagcacgccg ggacgctgca atggggcggc gtctatggcc attcctggtt cgtcgaccgc      1080
gcgctgggac tcagcgtgct gctgctcacc aataccgcct acgaaggcat gtcgggcccg      1140
ctgacgatcg ccttgcgcga cgccgtctac gcgcgctga                            1179

<210> SEQ ID NO 51
<211> LENGTH: 897
<212> TYPE: DNA
<213> ORGANISM: Burkholderia gladioli
<220> FEATURE:
<221> NAME/KEY: misc_feature
<223> OTHER INFORMATION: sequence coding for SEQ ID NO:2

<400> SEQUENCE: 51
atgaaccatc ccgatatcga cactcattca cgaaatgccg ccgcgccttt acccttttgtg     60 ttggtccatg gagcctggca tggagcctgg gcctatgaac gattaggagc ggcgttggcg     120
gcgcgtggac atgccagtgt cgcgcatgat ttacccgcgc atggaattaa tgcccgatat     180
ccggccgcgt tttggcaagg agatgcgcaa gcgttagcgc aagaaccgtc tccggtcgcg     240
gccacaactt tagacgatta tacaggacaa gtgttacgag cgatcgatgc tgcttgtgct     300
cttggtcacc cgagagtagt gcttgtaggt catagtatgg gtggtgtagc tatcacagcc     360
gcggctgaaa gagctccgga agaatcgct gctcttgtat atcttgctgc gttcatgcct     420
gctagtggtg tacctggtct tgattacgtg agagctcctg aaaaccatgg cgaaatgctg     480
gcctcgctga tctgcgccag ccctcgcgcg atcgcgcgcg tgcgcatcaa cccggccagc     540
cgcgacgcgg cctatctcgc cacgctgaag caggcgctgt tcgaggatgt tgacgaggcg     600
acgttccgcg ccgtgacacg gctgatgtcc tcggacgtgc cgaccgcgcc attcgccacg     660
ccgatcgcga ccacggccga gcgctggggc tcgatcgcgc gccactacgt gacctgcgcc     720
gaggatcgcg tgatcctgcc ggcgctgcag cggcgcttca tcgccgaggc cgacgccttc     780
ctgcccgagc ggccgacgcg cgtccacgca ctcgacagca gccattcgcc gttcctgtcc     840
cagcccgaca cgctcgccga gttgctgacg ggcatcgcgc gcaacacggc gatctga       897

<210> SEQ ID NO 52
<211> LENGTH: 585
<212> TYPE: DNA
<213> ORGANISM: Humicola insolens
<220> FEATURE:
<221> NAME/KEY: misc_feature
<223> OTHER INFORMATION: codes for cutinase according to SEQ ID NO:5

<400> SEQUENCE: 52
ggtaccggcg caatcgaaaa cggcctggaa tccggctccg caaacgcatg cccagatgca     60
atcctgatct tcgcacgcgg ctccaccgaa ccaggcaaca tgggcatcac cgtgggccca     120
gcactggcaa acggcctgga atcccacatc cgcaacatct ggatccaggg cgtgggcggc     180
```

| | |
|---|---|
| ccatacgatg cagcactggc aaccaacttc ctgccacgcg gcacctccca ggcaaacatc | 240 |
| gatgaaggca agcgcctgtt cgcactggca aaccagaagt gcccaaacac cccagtggtg | 300 |
| gcaggcggct actcccaggg cgcagcactg atcgcagcag cagtgtccga actgtccggc | 360 |
| gcagtgaagg aacaggtgaa gggcgtggca ctgttcggct acacccagaa cctgcagaac | 420 |
| cgcggcggca tcccaaacta cccacgcgaa cgcaccaagg tgttctgcaa cgtgggcgat | 480 |
| gcagtgtgca ccggcaccct gatcatcacc ccagcacacc tgtcctacac catcgaagca | 540 |
| cgcggcgaag cagcacgctt cctgcgcgat cgcatccgcg cataa | 585 |

<210> SEQ ID NO 53
<211> LENGTH: 954
<212> TYPE: DNA
<213> ORGANISM: Candida antarctica
<220> FEATURE:
<221> NAME/KEY: misc_feature
<223> OTHER INFORMATION: codes for lipase B according to SEQ ID NO:6

<400> SEQUENCE: 53

| | |
|---|---|
| ctaccttccg gttcggaccc tgccttttcg cagcccaagt cggtgctcga tgcgggtctg | 60 |
| acctgccagg tgcttcgcc atcctcggtc tccaaaccca tccttctcgt ccccggaacc | 120 |
| ggcaccacag gtccacagtc gttcgactcg aactggatcc ccctctctgc gcagctgggt | 180 |
| tacacaccct gctggatctc accccgccg ttcatgctca acgacaccca ggtcaacacg | 240 |
| gagtacatgg tcaacgccat caccacgctc tacgctggtt cgggcaacaa caagcttccc | 300 |
| gtgctcacct ggtcccaggg tggtctggtt gcacagtggg gtctgacctt cttccccagt | 360 |
| atcaggtcca aggtcgatcg acttatggcc tttgcgcccg actacaaggg caccgtcctc | 420 |
| gccggccctc tcgatgcact cgcggttagt gcacctccg tatggcagca aaccaccggt | 480 |
| tcggcactca ctaccgcact ccgaaacgca ggtggtctga cccagatcgt gcccaccacc | 540 |
| aacctctact cggcgaccga cgagatcgtt cagcctcagg tgtccaactc gccactcgac | 600 |
| tcatcctacc tcttcaacgg aaagaacgtc caggcacagg ctgtgtgtgg gccgctgttc | 660 |
| gtcatcgacc atgcaggctc gctcacctcg cagttctcct acgtcgtcgg tgatcgcc | 720 |
| ctgcgctcca ccacgggcca ggctcgtagt gcagactatg gcattacgga ctgcaaccct | 780 |
| cttcccgcca atgatctgac tccgagcaa aaggtcgccg cggctgcgct cctggcgccg | 840 |
| gcggctgcag ccatcgtggc gggtccaaag cagaactgcg agcccgacct catgccctac | 900 |
| gcccgcccct ttgcagtagg caaaaggacc tgctccggca tcgtcacccc ctga | 954 |

<210> SEQ ID NO 54
<211> LENGTH: 1179
<212> TYPE: DNA
<213> ORGANISM: Artificial sequence
<220> FEATURE:
<223> OTHER INFORMATION: Gene coding for modified EstB_N27 (according to SEQ ID NO:3)
<220> FEATURE:
<221> NAME/KEY: misc_feature
<223> OTHER INFORMATION: codes for N27 according to SEQ ID NO:3
<220> FEATURE:
<221> NAME/KEY: misc_feature
<222> LOCATION: (1)..(42)
<223> OTHER INFORMATION: coding for amino acids which are missing in the active protein
<220> FEATURE:
<221> NAME/KEY: misc_feature
<222> LOCATION: (49)..(51)
<223> OTHER INFORMATION: codon TCG of wildtype (SEQ ID NO:50) mutated to TTG, resulting in Ser17Leu
<220> FEATURE:
<221> NAME/KEY: misc_feature
<222> LOCATION: (60)..(60)
<223> OTHER INFORMATION: silent nucleotide exchange G to A
<220> FEATURE:
<221> NAME/KEY: misc_feature
<222> LOCATION: (394)..(396)
<223> OTHER INFORMATION: codon GGC of wildtype (SEQ ID NO:50) mutated to
    AGC, resulting in Gly132Ser
<220> FEATURE:
<221> NAME/KEY: misc_feature
<222> LOCATION: (513)..(513)
<223> OTHER INFORMATION: silent nucleotide exchange G to A
<220> FEATURE:
<221> NAME/KEY: misc_feature
<222> LOCATION: (751)..(753)
<223> OTHER INFORMATION: codon GAA of wildtype (SEQ ID NO:50) mutated to
    GAA, resulting in Glu251Gly
<220> FEATURE:
<221> NAME/KEY: misc_feature
<222> LOCATION: (931)..(933)
<223> OTHER INFORMATION: codon GCC of wildtype (SEQ ID NO:50) mutated to
    GTC, resulting in Ala311Val
<220> FEATURE:
<221> NAME/KEY: misc_feature
<222> LOCATION: (946)..(948)
<223> OTHER INFORMATION: codon GAG of wildtype (SEQ ID NO:50) mutated to
    AAG, resulting in Glu316Lys

<400> SEQUENCE: 54

```
atgaccgctg cctcgctcga cccgaccgct ttctccctcg atgccgcctt gctggccgca    60
cgtctcgatg ccgtgttcga ccaggcgctg cgcgaacggc gcctggtcgg cgcggtggcg   120
atcgtcgcgc ggcacggcga gatcctgtat cgccgcgccc agggcctggc cgaccgagag   180
gcaggtcggc cgatgcgcga ggacacgctg ttccggctcg cttcggtgac caagccgatc   240
gtcgcgctgg cggtgctgcg actggtggcg cgcggcgaac tcgcgctcga cgcgccggtc   300
acgcgctggt tgcccgaatt ccggccgcgg ctggccgacg gcagcgagcc gctcgtcacg   360
attcaccacc tgctcacgca cacgtcgggg ctcagctact ggctgctcga gggcgccggc   420
tccgtgtacg accggctcgg catctcggac ggcatcgacc tgcgcgactt cgatctcgac   480
gaaaacctgc ccgcctcgc ctcggcgccg ctatccttcg cgccgggcag cggctggcag   540
tattcgctgg cgctcgacgt gctcggcgcg gtggtcgagc gcgccaccgg gcagccgctg   600
gcggcggcgg tggacgcgtt ggtcgcccag ccgctcggca tgcgcgattg cggtttcgtc   660
tcggcggagc ccgagcgctt cgccgtgcct taccacgacg ccagccgga gccggtcgcg   720
atgcgcgacg gcatcgaggt gccgctgccg ggaggccacg gcgcggccgt gcgtttcgcg   780
ccctcccgcg tgttcgagcc gggcgcctat ccctcgggcg cgccggcat gtacggctcg   840
gccgacgacg tcctgcgcgc gctcgaggcg atccgcgcca atcccggttt cctgcccgag   900
acgctggcca cgcggcgcg ccgcgaccag gtcgagtcg cgccaagac gcgcggcccc   960
ggctggggct tcggctacct gagcgcggtg ctcgacgatc cggccgcggc cggcaccccg   1020
cagcacgccg ggacgctgca atggggcggc gtctatggcc attcctggtt cgtcgaccgc   1080
gcgctgggac tcagcgtgct gctgctcacc aataccgcct acgaaggcat gtcgggcccg   1140
ctgacgatcg ccttgcgcga cgccgtctac gcgcgctga                          1179
```

<210> SEQ ID NO 55
<211> LENGTH: 1179
<212> TYPE: DNA
<213> ORGANISM: Artificial sequence
<220> FEATURE:
<223> OTHER INFORMATION: DNA coding for EstB_NJ70 (SE ID NO:4)
<220> FEATURE:

<221> NAME/KEY: misc_feature
<223> OTHER INFORMATION: codes for NJ_70 according to SEQ ID NO:4

<400> SEQUENCE: 55

| | |
|---|---|
| atgaccgctg cctcactcga cctgaccgcc ttctccctcg atgccgcctc gctggccgcg | 60 |
| cgtctcgatg ccgtgttcga ccaggcgctg cgcgaacggc gcctggtcgg cgcggtggcg | 120 |
| atcgtcgcgc ggcacggcga gatcctgtat cgccgcgccc agggcctggc cgaccgagag | 180 |
| gcaggtcggc cgatgcgcga ggacacgctg ttccggctcg cttcggtgac caagccgatc | 240 |
| gtcgcgctgg cggtgctgcg gctggtggcg cgcggcgagc tcgcgctcga cgcgccggtc | 300 |
| acgcgctggt tgcccgaatt ccggccgcgg ctggccgacg gcagcgagcc gctcgtcacg | 360 |
| attcaccacc tgctcacgca cacgtcgggg ctcagctaca ggctgctcga gggcgccggc | 420 |
| tccgtgtacg accggctcgg catctcggac ggcatcgacc tgtgcgactt cgatctcgac | 480 |
| gaaaacctgc gccgcctcgc ctcggcgccg ctgtccttcg cgccgggcag cggctggcag | 540 |
| tattcgctgg cgctcgacgt gctcggcgcg gtggtcgagc gcgccaccgg gcagccgctg | 600 |
| gccgcggcgg tggacgcgtt ggtcgcccag ccgctcggca tgcgcgattg cggtttcgtc | 660 |
| tcggcggagc ccgagcgctt cgccgtgcct taccacgacg gccagcctga ccggtgcgc | 720 |
| atgcgcgacg gcatcgaggt gccgctgccg ggaggccacg gcgcggccgt gcgtttcgcg | 780 |
| ccctcccgcg tgttcgagcc gggcgcctat ccctcgggcg gcgccggcat gtacggctcg | 840 |
| gccgacgacg tcctgcgcgc gctcgaggcg atccgcgcca atcccggttt cctgcccgag | 900 |
| acgctggccg acgcggcgcg ccgcgaccag gtcggagtcg gcgccaagac gcgcggcccc | 960 |
| ggctggggct tcggctactt gagcgcggtg ctcgacgatc cggccgcggc cggcaccccg | 1020 |
| cagcacgccg ggacgctgca atggggcggc gtctatggcc attcctggtt cgtcgaccgc | 1080 |
| gcgctgggac tcagcgtgct gctgctcacc aataccgcct acgaaggcat gtcgggcccg | 1140 |
| ctgacgatcg ccttgcgcga cgccgtctac gcgcgctga | 1179 |

<210> SEQ ID NO 56
<211> LENGTH: 1170
<212> TYPE: DNA
<213> ORGANISM: Artificial sequence
<220> FEATURE:
<223> OTHER INFORMATION: sequence coding for EstB_N27_Short4 (SEQ ID NO:37)
<220> FEATURE:
<221> NAME/KEY: misc_feature
<222> LOCATION: (951)..(952)
<223> OTHER INFORMATION: nucleotides CGCGGCCCC of position 952 to 960 of N27 (SEQ ID NO:54) are deleted between nucleotids 952 and 952 of N27_Short4 (SEQ ID NO:56)

<400> SEQUENCE: 56

| | |
|---|---|
| atgaccgctg cctcgctcga cccgaccgct ttctccctcg atgccgcctt gctggccgca | 60 |
| cgtctcgatg ccgtgttcga ccaggcgctg cgcgaacggc gcctggtcgg cgcggtggcg | 120 |
| atcgtcgcgc ggcacggcga gatcctgtat cgccgcgccc agggcctggc cgaccgagag | 180 |
| gcaggtcggc cgatgcgcga ggacacgctg ttccggctcg cttcggtgac caagccgatc | 240 |
| gtcgcgctgg cggtgctgcg actggtggcg cgcggcgaac tcgcgctcga cgcgccggtc | 300 |
| acgcgctggt tgcccgaatt ccggccgcgg ctggccgacg gcagcgagcc gctcgtcacg | 360 |
| attcaccacc tgctcacgca cacgtcgggg ctcagctact ggctgctcga gggcgccggc | 420 |
| tccgtgtacg accggctcgg catctcggac ggcatcgacc tgtgcgactt cgatctcgac | 480 |
| gaaaacctgc gccgcctcgc ctcggcgccg ctatccttcg cgccgggcag cggctggcag | 540 |

```
tattcgctgg cgctcgacgt gctcggcgcg gtggtcgagc gcgccaccgg gcagccgctg    600
gcggcggcgg tggacgcgtt ggtcgcccag ccgctcggca tgcgcgattg cggtttcgtc    660
tcggcggagc ccgagcgctt cgccgtgcct taccacgacg gccagccgga gccggtgcgc    720
atgcgcgacg gcatcgaggt gccgctgccg ggaggccacg gcgcggccgt gcgtttcgcg    780
ccctcccgcg tgttcgagcc gggcgcctat ccctcgggcg gcgccggcat gtacggctcg    840
gccgacgacg tcctgcgcgc gctcgaggcg atccgcgcca atcccggttt cctgcccgag    900
acgctggccg acgcggcgcg ccgcgaccag gtcggagtcg gcgccaagac gggctggggc    960
ttcggctacc tgagcgcggt gctcgacgat ccggccgcgg ccggcacccc gcagcacgcc   1020
gggacgctgc aatgggcgg cgtctatggc cattcctggt tcgtcgaccg cgcgctggga   1080
ctcagcgtgt gctgctcac caataccgcc tacgaaggca tgtcgggccc gctgacgatc   1140
gccttgcgcg acgccgtcta cgcgcgctga                                    1170
```

<210> SEQ ID NO 57
<211> LENGTH: 1170
<212> TYPE: DNA
<213> ORGANISM: Artificial sequence
<220> FEATURE:
<223> OTHER INFORMATION: codes for EstB_N27_Short5 (SEQ ID NO:38)
<220> FEATURE:
<221> NAME/KEY: misc_feature
<223> OTHER INFORMATION: codes for EstB_N27_Short5
<220> FEATURE:
<221> NAME/KEY: misc_feature
<222> LOCATION: (1)..(42)
<223> OTHER INFORMATION: codes for EstB_N27_Short5
<220> FEATURE:
<221> NAME/KEY: misc_feature
<222> LOCATION: (746)..(759)
<223> OTHER INFORMATION: the sequence ctgGGGACGACGgcc from nucleotide
      746 to 759 of N27_Short 5 corresponds to nucleotides 745 to 768
      of EstB-wt (SEQ ID NO:50), i.e. ctgCCGGAAGGCCACGGCGCGgcc

<400> SEQUENCE: 57

```
atgaccgctg cctcgctcga cccgaccgct ttctccctcg atgccgcctt gctggccgca     60
cgtctcgatg ccgtgttcga ccaggcgctg cgcgaacggc gcctggtcgg cgcggtggcg    120
atcgtcgcgc ggcacggcga gatcctgtat cgccgcgccc agggcctggc cgaccgagag    180
gcaggtcggc cgatgcgcga ggacacgctg ttccggctcg cttcggtgac caagccgatc    240
gtcgcgctgg cggtgctgcg actggtggcg cgcggcgaac tcgcgctcga cgcgccggtc    300
acgcgctggt tgcccgaatt ccggccgcgg ctggccgacg cagcgagcc gctcgtcacg    360 attcaccacc tgctcacgca cacgtcgggg ctcagctact ggctgctcga gggcgccggc    420
tccgtgtacg accggctcgg catctcggac ggcatcgacc tgcgcgactt cgatctcgac    480
gaaaacctgc gccgcctcgc ctcggcgccg ctatccttcg cgccgggcag cggctggcag    540
tattcgctgg cgctcgacgt gctcggcgcg gtggtcgagc gcgccaccgg gcagccgctg    600
gcggcggcgg tggacgcgtt ggtcgcccag ccgctcggca tgcgcgattg cggtttcgtc    660
tcggcggagc ccgagcgctt cgccgtgcct taccacgacg gccagccgga gccggtgcgc    720
atgcgcgacg gcatcgaggt gtcgctgggg acgacgccgc tgcgtttcgc gccctcccgc    780
gtgttcgagc cgggcgccta tccctcgggc ggcgccggca tgtacggctc ggccgacgac    840
gtcctgcgcg cgctcgaggc gatccgcgcc aatcccggtt tcctgcccga cgcgctggcc    900
gacgcggcgc gccgcgacca ggtcggagtc ggcgccaaga cgcgcggccc cggctggggc    960
ttcggctacc tgagcgcggt gctcgacgat ccggccgcgg ccggcacccc gcagcacgcc   1020
```

```
gggacgctgc aatggggcgg cgtctatggc cattcctggt tcgtcgaccg cgcgctggga    1080
ctcagcgtgc tgctgctcac caataccgcc tacgaaggca tgtcgggccc gctgacgatc    1140
gccttgcgcg acgccgtcta cgcgcgctga                                      1170
```

<210> SEQ ID NO 58
<211> LENGTH: 257
<212> TYPE: PRT
<213> ORGANISM: Hevea brasiliensis
<220> FEATURE:
<221> NAME/KEY: MISC_FEATURE
<223> OTHER INFORMATION: Hydroxynitrile lyase, GenBank No. AAC49184

<400> SEQUENCE: 58

```
Met Ala Phe Ala His Phe Val Leu Ile His Thr Ile Cys His Gly Ala
1               5                   10                  15

Trp Ile Trp His Lys Leu Lys Pro Leu Leu Glu Ala Leu Gly His Lys
            20                  25                  30

Val Thr Ala Leu Asp Leu Ala Ala Ser Gly Val Asp Pro Arg Gln Ile
        35                  40                  45

Glu Glu Ile Gly Ser Phe Asp Glu Tyr Ser Glu Pro Leu Leu Thr Phe
    50                  55                  60

Leu Glu Ala Leu Pro Pro Gly Glu Lys Val Ile Leu Val Gly Glu Ser
65                  70                  75                  80

Cys Gly Gly Leu Asn Ile Ala Ile Ala Ala Asp Lys Tyr Cys Glu Lys
                85                  90                  95

Ile Ala Ala Ala Val Phe His Asn Ser Val Leu Pro Asp Thr Glu His
            100                 105                 110

Cys Pro Ser Tyr Val Val Asp Lys Leu Met Glu Val Phe Pro Asp Trp
        115                 120                 125

Lys Asp Thr Thr Tyr Phe Thr Tyr Thr Lys Asp Gly Lys Glu Ile Thr
    130                 135                 140

Gly Leu Lys Leu Gly Phe Thr Leu Leu Arg Glu Asn Leu Tyr Thr Leu
145                 150                 155                 160

Cys Gly Pro Glu Glu Tyr Glu Leu Ala Lys Met Leu Thr Arg Lys Gly
                165                 170                 175

Ser Leu Phe Gln Asn Ile Leu Ala Lys Arg Pro Phe Phe Thr Lys Glu
            180                 185                 190

Gly Tyr Gly Ser Ile Lys Lys Ile Tyr Val Trp Thr Asp Gln Asp Glu
        195                 200                 205

Ile Phe Leu Pro Glu Phe Gln Leu Trp Gln Ile Glu Asn Tyr Lys Pro
    210                 215                 220

Asp Lys Val Tyr Lys Val Glu Gly Gly Asp His Lys Leu Gln Leu Thr
225                 230                 235                 240

Lys Thr Lys Glu Ile Ala Glu Ile Leu Gln Glu Val Ala Asp Thr Tyr
                245                 250                 255

Asn
```

<210> SEQ ID NO 59
<211> LENGTH: 258
<212> TYPE: PRT
<213> ORGANISM: Manihot esculenta
<220> FEATURE:
<221> NAME/KEY: misc_feature
<223> OTHER INFORMATION: Hydroxynitrile lyase; SwissProt No. P52705

<400> SEQUENCE: 59

```
Met Val Thr Ala His Phe Val Leu Ile His Thr Ile Cys His Gly Ala
1               5                   10                  15

Trp Ile Trp His Lys Leu Lys Pro Ala Leu Glu Arg Ala Gly His Lys
                20                  25                  30

Val Thr Ala Leu Asp Met Ala Ala Ser Gly Ile Asp Pro Arg Gln Ile
            35                  40                  45

Glu Gln Ile Asn Ser Phe Asp Glu Tyr Ser Glu Pro Leu Leu Thr Phe
    50                  55                  60

Leu Glu Lys Leu Pro Gln Gly Glu Lys Val Ile Ile Val Gly Glu Ser
65                  70                  75                  80

Cys Ala Gly Leu Asn Ile Ala Ile Ala Ala Asp Arg Tyr Val Asp Lys
                85                  90                  95

Ile Ala Ala Gly Val Phe His Asn Ser Leu Leu Pro Asp Thr Val His
                100                 105                 110

Ser Pro Ser Tyr Thr Val Glu Lys Leu Leu Glu Ser Phe Pro Asp Trp
            115                 120                 125

Arg Asp Thr Glu Tyr Phe Thr Phe Thr Asn Ile Thr Gly Glu Thr Ile
    130                 135                 140

Thr Thr Met Lys Leu Gly Phe Val Leu Leu Arg Glu Asn Leu Phe Thr
145                 150                 155                 160

Lys Cys Thr Asp Gly Glu Tyr Glu Leu Ala Lys Met Val Met Arg Lys
                165                 170                 175

Gly Ser Leu Phe Gln Asn Val Leu Ala Gln Arg Pro Lys Phe Thr Glu
            180                 185                 190

Lys Gly Tyr Gly Ser Ile Lys Lys Val Tyr Ile Trp Thr Asp Gln Asp
    195                 200                 205

Lys Ile Phe Leu Pro Asp Phe Gln Arg Trp Gln Ile Ala Asn Tyr Lys
    210                 215                 220

Pro Asp Lys Val Tyr Gln Val Gln Gly Gly Asp His Lys Leu Gln Leu
225                 230                 235                 240

Thr Lys Thr Glu Glu Val Ala His Ile Leu Gln Glu Val Ala Asp Ala
                245                 250                 255

Tyr Ala
```

METHOD FOR THE ENZYME-CATALYSED HYDROLYSIS OF POLYACRYLIC ACID ESTERS, AND ESTERASES USED THEREFOR

RELATED APPLICATIONS

This application is a continuation of U.S. application Ser. No. 14/100,680 filed Dec. 9, 2013, which is a continuation of U.S. application Ser. No. 13/003,597 filed Jan. 11, 2011, which is a national stage application under 35 U.S.C. §371 of PCT/EP2009/059212, filed Jul. 17, 2009, which claims benefit of European application 08160774.9, filed Jul. 18, 2008. The entire content of each aforementioned application is hereby incorporated by reference in its entirety.

SUBMISSION OF SEQUENCE LISTING

The Sequence Listing associated with this application is filed in electronic format via EFS-Web and is hereby incorporated by reference in its entirety into the specification. The name of the text file containing the Sequence Listing is Sequence_Listing_074012_0286_01. The size of the text file is 125 KB, and the text file was created on Feb. 24, 2016.

FIELD OF THE INVENTION

The present invention relates to a method for the enzyme-catalyzed hydrolysis of polyacrylic acid esters, the enzymes used and mutants thereof, the enzymes encoding nucleic acids, the nucleic acids comprising vectors, the vectors comprising microorganisms, the use of the enzymes, the vectors or the microorganisms for carrying out a method for the enzyme-catalyzed hydrolysis of polyacrylic acid esters. The present application relates furthermore to polymeric reaction products obtainable by the method and methods for the production of esterases.

BACKGROUND OF THE INVENTION

Polyacrylic acid esters (polyacrylates) are compounds with numerous uses. For polyacrylates from homopolymers the possible uses are rather limited, whereas in the case of polyacrylates from copolymers it is possible, by selecting the comonomers to be used (for example methylacrylates, styrene, acrylonitrile, vinyl acetate, vinyl chloride, vinylidene chloride and butadiene) to exert an influence on the properties of the polyacrylates in various ways and therefore provide access to the most varied possible uses.

Chemical methods for cleavage of polyacrylic acid esters, for example alkaline saponification (U.S. Pat. No. 3,926,891), are known by a person skilled in the art. US patent application 2004/0082023 A1 describes a method of enzymatic esterification of polymers bearing carboxyl groups using enzymes such as lipases or esterases. Polyacrylates are not named explicitly as possible polymers, nor is there any mention of the suitability of the method for the enzyme-catalyzed ester cleavage of polyacrylate esters.

O'Sullivan and Birkinshaw described an attempt to hydrolyze poly-(n-butylcyanoacrylate) nanoparticles by esterase from pig's liver (O'Sullivan, Birkinshaw, Polymer Degradation and Stability 78: 7-15, 2002). Belucci et al. reported on the careful removal of acrylic resin coatings from the surface of paintings using lipase (Belluci et al., Study in Conservation 44: 278-281, 1999).

A large number of esterases are known by a person skilled in the art. Esterases of *Burkholderia gladioli* are described for example in Peterson et al., J. Biotechnol. 89:11-25 (2001), Valinger et al., J. Biotechnol. 129:98-108 (2007), Ivancic et al., J. Biotechnol. 129:109-122 (2007) and Reiter et al., Appl. Microbiol. Biotechnol. 54:778-785 (2000). Suitability of these esterases for the cleavage of polymer substrates has not been described before.

The problem on which the present invention is based therefore consists of providing a method for the enzyme-catalyzed hydrolysis of polyacrylic acid esters and suitable enzymes therefor, their nucleic acids, the nucleic acid-containing vectors or the vector-containing microorganisms, and reaction products obtainable by the method.

BRIEF SUMMARY OF THE INVENTION

The aforementioned problem was solved, surprisingly, by the use of esterases, in particular enzymes selected from carboxyl esterases, triacyl lipases and cutinases, in a method for the enzyme-catalyzed hydrolysis of polyacrylic acid esters and by the provision of corresponding esterases and of the nucleic acids encoding them.

BRIEF DESCRIPTION OF THE DRAWINGS

FIGS. 5a and 5b give an overview of active mutants and activities. The results were obtained by pH-shift assays with esterase C (FIG. 5a) and esterase B (FIG. 5b) and various functional mutants thereof. The following symbols were used for the activity: +++=very active, ++=active, +=weakly active, ○=not active EstB and mutants thereof were not tested for α-naphthyl acetate in obtaining these data, however, the inventors have data available showing that all three EstB variants have activity with respect to this substrate.

DETAILED DESCRIPTION OF THE INVENTION

I. Explanations of General Terms

Figure 1:
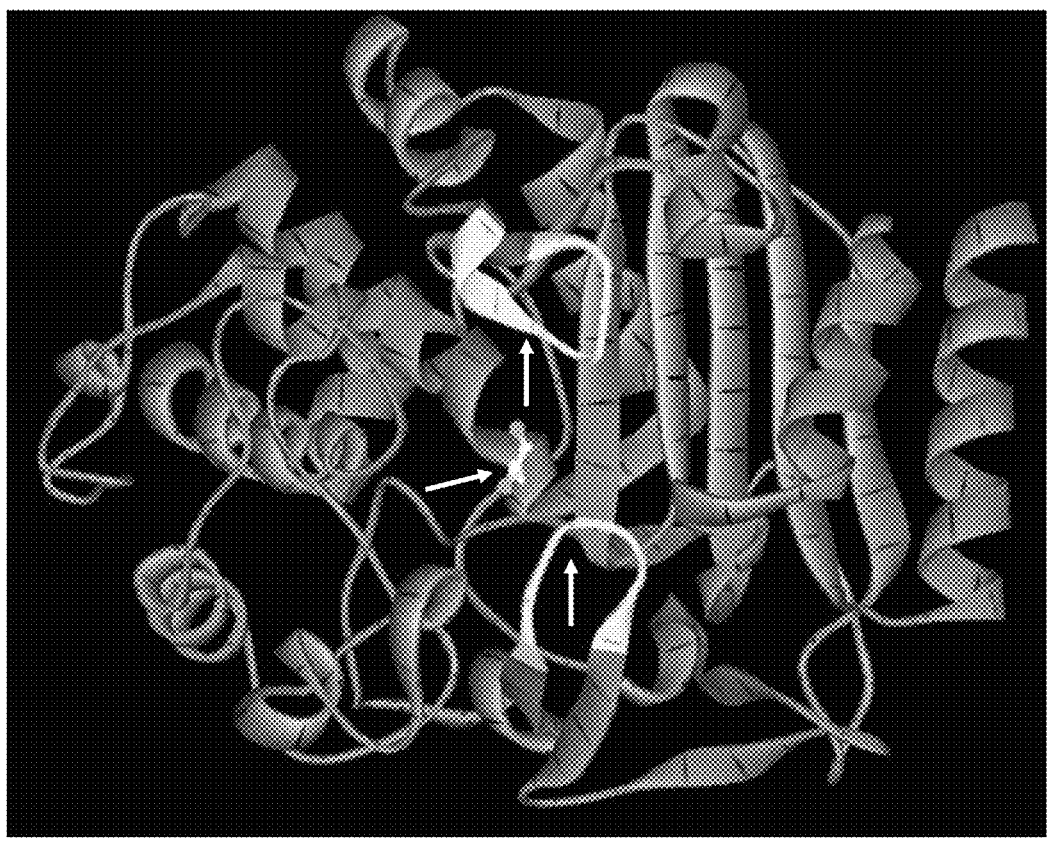
FIG. 1 shows a structural model of EstB. Two loops, which were identified as covering the access to the catalytically active center, are highlighted and marked with arrows. The amino acid residue, highlighted and also indicated with an arrow, represents the nucleophilic serine of the active center.

Within the scope of the present invention, unless specified otherwise, the term "esterases" generally denotes enzymes that catalyze the hydrolysis of ester bonds.

"Enzymes acting on ester bonds" means enzymes of class 3.1 according to the EC classification. "Carboxylic acid ester hydrolases" means enzymes of class 3.1.1 according to the EC classification. "Carboxyl esterases", "triacylglycerol lipases" or "cutinases" mean enzymes of EC classes 3.1.1.1, 3.1.1.3 and/or 3.1.1.74.

"Esterases of family VIII" are covered by the definition given in Petersen et al., J Biotechnol 89:11-25 (2001) and in Arpigny and Jaeger, Biochem J 343:177-183 (1999). Esterases of family VIII are therefore characterized by an active site that has a Ser-X-X-Lys motif (where X stands for any amino acid) and therefore have similarity with the active site of β-lactamases of class C, it being possible for the esterase activity to be detected if necessary by one of the esterase activity assays described in Petersen et al. (ibid.).

Within the scope of the invention, type C esterases are to be understood as enzymes that have at least 50% identity at the amino acid level with EstC from *Burkholderia gladioli* (Reiter et al., Appl Microbiol Biotechnol 54:778-785 (2000) according to SEQ ID NO:2, and moreover at least 20% identity at the amino acid level with the hydroxynitrile lyase from *Hevea brasiliensis* (Hasslacher M et al., J Biol Chem 271:5884-5891 (1996), GenBank accession No. AAC49184), SEQ ID NO:58, and/or the hydroxynitrile lyase from *Manihot esculenta* (Hughes et al., Arch Biochem Biophys 311:96-502 (1994), Swiss-Prot accession No. P52705), SEQ ID NO:59.

Within the scope of the present invention, an "enzyme-catalyzed hydrolysis" of a polyacrylic acid ester also comprises reactions that include a partial autolysis. In "partial autolysis" a proportion of 0-90 mol. %, 0-50 mol. %, 0-25 mol. %, 0-20 mol. %, in particular 0-15 mol. %, 0-10 mol. %, 0-5 mol. % or 0-1 mol. % of the ester groups is cleaved autolytically.

Halogen means fluorine, chlorine, bromine or iodine.

A loop or a loop structure means a segment of successive amino acids in the primary structure, which forms a loop-shaped structural element in the tertiary structure of the protein.

Hydrolysis of polyacrylic acid esters or hydrolysis activity against polyacrylic acid esters means the incomplete or complete hydrolysis of the ester bonds of the polyacrylic acid esters.

The statement "about" means that the value given optionally has a deviation of up to 25% above or below, in particular up to 10% above or below, or up to 5% above or below.

Average molecular weight means, unless further specified, the weight-average molecular weight.

An alternating copolymer is to be understood as a copolymer consisting of two monomers A and B, the monomers being in a strictly alternating sequence $(AB)_n$. A random copolymer means a copolymer in which the monomers (e.g. A and B) are incorporated randomly in the macromolecule that forms during copolymerization, i.e. in a purely random order. A gradient copolymer is a copolymer in which there is a gradient of the distribution of the monomer building blocks (e.g. the building blocks A and B) along the chains of the copolymers. A block polymer is a polymer whose molecules consist of linearly linked blocks. A block is to be understood as a segment of a polymer molecule that comprises several identical repeat units and has at least one constitutional or configurative feature that differs from those of the adjoining segments (blocks). The blocks are joined together directly or via constitutional units, which are not part of the blocks. Block copolymers are block polymers that consist of more than one kind of monomer and can be described e.g. for block copolymers constructed from two kinds of monomers A and B by the general formula $-A_k-B_l-A_m-B_n-$, where k, l, m and n stand for the number of repeat units in the individual blocks. Graft copolymers are polymers produced according to the method of graft copolymerization, with their structure having the characteristic that they possess, on their main chain, side chains that are of a length such that they could already be regarded as polymers. The main and side chains can be chemically identical or different.

Alcohol derivatives are to be understood as molecules derived from alcohols, for example alcohols in which one or more hydroxyl groups are replaced with other functional groups, for example amino groups or sulfhydryl groups.

A "partial" ester cleavage occurs when, after carrying out the method according to the invention, the ester groups originally present (i.e. basically cleavable) have not been cleaved. For example, a partial cleavage can relate to values from 0.1 to 99.9% of the ester groups originally contained, e.g. at least 1, 2, 3, 4, 5, 6, 7, 8, 9, 10, 11, 12, 13, 14, 15, 16, 17, 18, 19 or 20%, or at most 99, 98, 97, 96, 95, 94, 93, 92, 91, 90, 89, 88, 87, 86, 85, 84, 83, 82, 81, 80%, for example 1 to 95, 2 to 90, 3 to 85, 4 to 80, 5 to 75, 6 to 70, 7 to 65, 8 to 60, 9 to 55, 10 to 50, 11 to 45, 12 to 40, 13 to 35, 14 to 30, 15 to 25 or 16 to 20%. The cleavage can take place regio-nonspecifically, i.e. essentially randomly distributed in the polymer molecule, or regio-specifically, i.e. nonrandomly distributed, predominantly in one or more specific regions of the molecule, e.g. in one or more terminal regions of the molecule.

A "mutant of an esterase according to SEQ ID NO: X" or a "mutant derived from SEQ ID NO:X" means that, starting from this SEQ ID NO:X, this mutant is produced by undertaking at least one mutation described herein or at least one combination of mutations described herein.

The following abbreviations are used, among others:
DG: 2,4-dimethylglutaric acid-dimethyl ester
DB: 2,4-dimethylglutaric acid-dibutyl ester
PMA: polymethylacrylate
PBA: polybutylacrylate
α-N: α-naphthyl acetate
p-NPA: para-nitrophenylacetate
p-NPB: para-nitrophenylbutyrate II. Special Objects of the Invention A first object of the invention relates to methods for the enzyme-catalyzed hydrolysis of polyacrylic acid esters, with at least one polyacrylic acid ester being prepared, and the at least one polyacrylic acid ester is incubated with at least one enzyme, which is selected from enzymes acting on ester bonds (EC 3.1), until the ester groups contained in the polyacrylic acid ester have been hydrolytically cleaved partially or completely, and optionally the resultant modified polymer is isolated. In this method, the polyacrylic acid ester can be a homopolymer or a copolymer from two or more different monomers.

According to further embodiments, the enzyme is selected from carboxylic acid ester hydrolases (EC 3.1.1). According to especially preferred embodiments the carboxylic acid ester hydrolases are selected from carboxyl esterases (E.C 3.1.1.1), triacylglycerol lipases (EC 3.1.1.3) and cutinases (EC 3.1.1.74).

According to further embodiments the polyacrylic acid ester is a homopolymer or a copolymer. Examples of copolymers are alternating copolymers, statistical copolymers, gradient copolymers, block copolymers or graft copolymers. The monomers of the copolymers can be for example all the monomers disclosed here.

According to a preferred embodiment of the method, the polymer comprises monomer building blocks of general formula I

$$R^1R^2C=CR^3-COOR^4 \quad (I),$$

in which
$R^1$, $R^2$ and $R^3$ may be identical or different and are selected from H, a linear $C_1$-$C_{20}$ hydrocarbyl residue and a branched $C_3$-$C_{20}$ hydrocarbyl residue, and $R^4$ is selected from H, a linear $C_1$-$C_{20}$ or $C_1$-$C_6$ hydrocarbyl residue, a branched $C_3$-$C_{20}$ or $C_3$-$C_6$ hydrocarbyl residue and a cyclic $C_3$-$C_{20}$ or $C_5$-$C_7$ hydrocarbyl residue, the hydrocarbyl residue optionally being substituted with one or more identical or different groups, which are selected from hydroxyl, amino, epoxide groups and halogen atoms, and in the polymer, in at least one monomer building block of formula I, $R^4$ is selected from a linear $C_1$-$C_{20}$ or $C_1$-$C_6$ hydrocarbyl residue, a branched $C_3$-$C_{20}$ or $C_3$-$C_6$ hydrocarbyl residue and a cyclic $C_3$-$C_{20}$ or $C_5$-$C_7$ hydrocarbyl residue, the hydrocarbyl residue optionally being substituted with one or more identical or different groups, which are selected from hydroxyl, amino, epoxide, thiol groups and halogen atoms.

Linear $C_1$-$C_{20}$ hydrocarbyl residues comprise methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonodecyl and eicosyl residues. Branched $C_3$-$C_{20}$ hydrocarbyl residues comprise for example isopropyl, isobutyl, isopentyl, 2,2-dimethylpropyl, isohexyl, 3-methylpentyl, 2,2-dimethylbutyl, 2,3-dimethylbutyl, isoheptyl, 3-methylhexyl, 2,2-dimethylpentyl, 2,3-dimethylpentyl, 2,4-dimethylpentyl, 2,2,3-trimethylbutyl, isooctyl, 3-methylheptyl, 4-methylheptyl, 2,2-dimethylhexyl, 2,4-dimethylhexyl, 2,5-dimethylhexyl, 2,2,3-trimethylpentyl, 2,2,4-trimethylpentyl, 2,2,5-trimethylpentyl and isononyl residues. Examples of $C_3$-$C_{20}$ cycloalkyl residues are cyclopropyl, cyclobutyl, cyclopentyl, cyclohexyl, cycloheptyl, cyclooctyl, cyclononyl, cyclodecyl, cycloundecyl, cyclododecyl, cyclotridecyl, cyclotetradecyl, cyclopentadecyl, cyclohexadecyl, cycloheptadecyl, cyclooctadecyl, cyclononadecyl and cycloeicosyl residues. Nonlimiting examples of substituted hydroxycarbyl residues are hydroxymethyl, hydroxyethyl, hydroxypropyl, hydroxybutyl, hydroxypentyl, hydroxyhexyl, hydroxyheptyl, hydroxyoctyl, hydroxynonyl and hydroxydecyl residues. The polymer of general formula (I) can thus, if several hydroxyl groups are present, be a polyol. According to further, nonlimiting examples, the hydroxycarbyl residues are selected from carbohydrates, thus in particular polyhydroxyaldehydes and polyhydroxyketones, which can be in the form of monomers, oligomers or polymers. Identical or different monomers can be present in one polyacrylic acid ester, and oligomers or polymers can comprise identical or different monomers. Carbohydrates are known by a person skilled in the art, and nonlimiting examples of polyhydroxyaldehydes include threose, ribose, arabinose, xylose, lyxose; nonlimiting examples of polyhydroxyketones include dihydroxyacetone, erythrulose, ribulose, xylulose, fructose, sorbose, mannoheptulose.

According to a further embodiment, the method according to the invention is characterized in that the polyacrylic acid ester contains, additionally to the monomers of formula I, at least one further monomer component different therefrom, in a molar proportion from 0 to 15 mol. %, which preferably is selected from N-vinylformamide, methacrylic acid, methacrylic acid ester, itaconic acid, itaconic acid ester, vinylphosphonic acid, vinylsulfonic acid, vinyl alcohol, N-vinylimidazole, N-vinylformamide, styrene, maleic acid, maleic acid ester, ethylene, propylene acrylamide and substituted acrylamides, where the substituent is selected from a linear $C_1$-$C_{20}$ or $C_1$-$C_6$ hydrocarbyl residue, a branched $C_3$-$C_{20}$ or $C_3$-$C_6$ hydrocarbyl residue and a cyclic $C_3$-$C_{20}$ or $C_5$-$C_7$ hydrocarbyl residue, the hydrocarbyl residue optionally being substituted with one or more identical or different groups, which are selected from hydroxyl, amino, epoxide, thiol groups and halogen atoms.

In one embodiment of the method, the acrylic acid groups of the polyacrylic acid esters are completely or substantially completely esterified prior to the hydrolysis.

In the methods according to the invention the average molecular weight of the polyacrylic acid ester is up to about 3 000 000, for example from about 1000 up to about 3 000 000, in particular up to about 200 000, 150 000, 100 000 or 50 000. The polyacrylic acid ester is preferably selected from polyacrylic acid methyl esters with an average molecular weight from about 20 000 to about 3 000 000, in particular about 30 000 to about 50 000, in particular about 40 000, and polyacrylic acid butyl esters with an average molecular weight from about 20 000 to about 3 000 000, in particular about 90 000 to about 110 000, in particular about 99 000.

In further embodiments of the method according to the invention the incubation takes place at a pH from 5 to 14, preferably 7 to 12, 8.5 to 11.5, in particular at a pH from 9 to 11 or at a pH from 7 to 9.

According to further embodiments of the method according to the invention, the enzyme is in a solution, in particular in an aqueous, organic or aqueous-organic, organic-aqueous or organic solution. Within the scope of the present invention, organic-aqueous or aqueous-organic solutions comprise not only homogeneous solutions of fully miscible components (for example water and organic solvent), but also two-phase systems or multiphase systems, for example water-in-oil emulsions, oil-in-water emulsions, water-in-oil-in-water emulsions, etc. The enzyme is then preferably completely or mainly in the aqueous phase, and the polyacrylic acid ester preferably completely or mainly in the organic phase. According to special embodiments the volume ratio of aqueous to organic component or of aqueous to organic phase is about 75:25 to 25:75, for example about 60:40 to about 40:60, about 55:45 to about 45:55, in particular about 50:50.

According to special embodiments the enzyme is present in nonimmobilized form.

According to a further embodiment of the method according to the invention, the enzyme is present in immobilized form. Examples of immobilized enzymes are enzymes bound covalently or noncovalently on microspheres or flat-shaped supports. Suitable methods for immobilization of enzymes are known by a person skilled in the art and are described for example in S. Fukui, A. Tanaka, "Enzymes", in: Ullmann's Encyclopedia of Industrial Chemistry, 5th edition, Wiley-VCH, New York, Berlin, 1985; J. E. Prenosil, O. M. Kut, I. J. Dunn, E. Heinzle, "Immobilized Biocatalysts", in: Ullmann's Encyclopedia of Industrial Chemistry, 6th edition, VCH, New York, Berlin, 2003, p. 503-554; J. F. Kennedy, J. M. S. Cabral, in: H. J. Rehm, G. Reed (Eds.), Biotechnology: A comprehensive treatise in 8 volumes; Vol. 7a, p. 349-404; VCH, Weinheim, 1987. Noncovalent binding of the enzyme can for example be achieved by labeling the enzyme with biotin and immobilization on a support provided with avidin or streptavidin, labeling of the enzyme by incorporating histidine tags in its amino acid sequence and immobilization on a support provided with nickel chelate, immobilization of the enzyme by antibodies directed against the enzyme (the binding epitopes preferably being selected so that the binding between antibody and binding epitope does not, or substantially does not, impair the access of substrate molecules to the active site), preparation of fusion proteins from the enzyme and a foreign protein and immobilization of the protein by antibodies directed against the foreign protein. By analogy with the above account, enzymes present in immobilized form can be a constituent of a two-phase system or multiphase system. For example, an enzyme immobilized on a solid support (for example a microsphere) can be regarded as solid phase, which is present within a two-phase system in a liquid phase (water or organic solvent), or the enzyme immobilized on a solid support can be present as solid phase in an already two-phase or multiphase liquid system (for example a water-in-oil emulsion or an oil-in-water emulsion).

According to a further embodiment, the method is carried out in a bioreactor.

In a further embodiment of the method according to the invention the enzyme is an esterase, which is selected from esterases of family VIII, type C esterases, a cutinase according to SEQ ID NO:5 or cutinases derived therefrom, and a triacylglycerol lipase according to SEQ ID NO:6 or triacylglycerol lipases derived therefrom. In a special embodiment the esterase of type VIII is the esterase B from *Burkholderia gladioli* (ATCC 10248) according to SEQ ID NO:1, in another special embodiment the type C esterase is the esterase C from *Burkholderia gladioli* (ATCC 10248) according to SEQ ID NO:2. The invention also relates to functional mutants of the aforesaid esterases.

According to further embodiments of the method according to the invention the esterase is a functional mutant of an esterase according to SEQ ID NO:1 or SEQ ID NO:2 with comparable or increased activity with respect to the hydrolysis of polyacrylic acid esters relative to SEQ ID NO:1 or SEQ ID NO:2, and/or a functional mutant of an esterase according to SEQ ID NO:1 or SEQ ID NO:2 with increased stability relative to SEQ ID NO:1 or SEQ ID NO:2, for example against the influence of organic solvents or with respect to denaturation by elevated temperatures.

According to further embodiments of the method according to the invention the mutant displays, in comparison with an esterase according to SEQ ID NO:1 or SEQ ID NO:2, an increased hydrolysis activity with respect to polyacrylic acid methyl esters and/or polyacrylic acid butyl esters. The hydrolysis activity can for example be determined quantitatively by a titration assay, in which ester cleavage takes place in solution and the decrease in pH caused by the acid groups that are released is compensated by adding NaOH (or another pH correctant). Increased hydrolysis activity occurs for example when the mutant brings about, in comparison with the corresponding esterase according to SEQ ID NO:1 or SEQ ID NO:2, a quicker establishment of reaction equilibrium (i.e. the same amount of NaOH has to be added in a shorter time) and/or displaces the equilibrium towards more complete hydrolysis (i.e. more NaOH must be added). The hydrolysis activity can furthermore be determined semi-quantitatively in a pH-shift assay by incubation of the enzyme mutant or of a microorganism producing the enzyme mutant with a substrate containing polyacrylic acid ester, which can be supplied for example in an agar medium or on a filter membrane, and determination of the drop in pH due to acid groups being released, by color change of a pH indicator that is also present. There is increased hydrolysis activity if the mutant, in comparison with the corresponding esterase according to SEQ ID NO:1 or SEQ ID NO:2, brings about a quicker change to low pH values or a more intense change (larger color change halos around enzyme-containing sites) to lower pH values.

According to further embodiments, the method according to the invention is characterized in that
(a) the esterase is a mutant of an esterase according to SEQ ID NO:1, which has at least one mutation, e.g. 1, 2, 3, 4, 5, 6 or 7 mutations, in one or more of the amino acid residues Ser17, Gly132, Trp134, Arg155, Glu251, Ala311 and Glu316; or
(b) the esterase is a mutant of an esterase according to SEQ ID NO:2, which has at least one mutation, e.g. 1, 2, 3, 4 or 5 mutations, in one or more of the amino acid residues Phe138, Val150, Leu160, Thr188 and Leu193.

In further embodiments the method according to the invention is characterized in that the esterase is derived from SEQ ID NO:1 and comprises
a) at least one, e.g. 1, 2, 3, 4 or 5 mutations, of the mutations Ser17Leu, Gly132Ser, Glu251Gly, Ala31Val and Glu316Lys and/or
b) at least one, e.g. 1, 2, 3, 4, 5, 6 or 7 mutations, of the mutations Pro8Leu, Gly132Ser, Trp134Arg, Arg155Cys, Glu251Gly, Ala311Val and Glu316Lys.

In especially preferred embodiments the method according to the invention is characterized in that the esterase is derived from SEQ ID NO:1 and comprises
(a) the mutations Ser17Leu, Gly132Ser, Glu251Gly, Ala31Val and Glu316Lys; or
(b) the mutations Pro8Leu, Gly132Ser, Trp134Arg, Arg155Cys, Glu251Gly, Ala311Val and Glu316Lys.

Esterases according to SEQ ID NO:3 or SEQ ID NO:4 represent special embodiments.

In further special embodiments the method according to the invention is characterized in that the esterase is derived from SEQ ID NO:2 and comprises one of the following mutations or combinations of mutations (i.e. one of the single or multiple mutations listed below):
(a) Phe138Ala
(b) Phe138Ala, Thr188Ser
(c) Phe138Ala, Leu160Ala, Thr188Ser
(d) Leu193Ala
(e) Leu193Ala, Phe138Ala, Thr188Ser, Val150Ala
(f) Leu193Ala, Phe138Ala, Thr188Ser
(g) Leu193Ala, Phe138Ala, Thr188Ser, Leu160Ala, Val150Ala
(h) Val150Ala
(i) Val150Ala, Thr188Ser
(j) Leu193Ala, Phe138Val
(k) Leu193Ala, Phe138Val, Thr188Ser, Val150Ala
(l) Leu193Ala, Thr188Ser
(m) Leu193Ala, Phe138Val, Thr188Ser
(n) Leu193Ala, Phe138Val, Thr188Ser, Leu160Ala
(o) Phe138Val, Val150Ala, Thr188Ser
(p) Phe138Val
(q) Phe138Val, Thr188Ser According to further embodiments of the method according to the invention the esterase is a deletion mutant of an esterase of type VIII or of a type C esterase. Preferably the esterase has a loop shortening. Suitable regions for a loop shortening in the case of an esterase according to SEQ ID NO:1 (EstB of *B. gladioli*) are for example the regions Glu246 to Arg258 and Gly312 to 323. Loop shortenings can be effected by removing one or more amino acids, and in the case when several amino acids are removed, in their turn one or more adjacent or nonadjacent amino acids in SEQ ID NO:1 can be removed. Deletion mutants of the amino acid sequences given under SEQ ID NO:37 and SEQ ID NO:38 represent special embodiments.

Another object of the invention relates to the previously mentioned functional esterase mutants.

Another object of the invention relates to nucleic acids
a) which code for functional esterase mutants, or
b) which represent nucleic acids complementary to a), and/or
c) nucleic acids hybridizing with a nucleic acid according to a) or b) under stringent conditions, in particular those nucleic acids that have a sequence identity of at least 80% and code for a mutant of an esterase of family VIII or a type C esterase mutant, which hydrolyzes polyacrylic acid esters.

Another object of the invention relates to a vector, comprising one of the aforementioned nucleic acids. According to a special embodiment the nucleic acid is linked operatively with a promoter.

Another object of the invention relates to a microorganism, comprising at least one of the aforementioned vectors.

Another object of the invention relates to a method of production of one of the aforementioned functional esterase mutants, in which
   a) a host organism capable of expressing the esterase, for example the aforementioned microorganism, which contains at least one of the aforementioned vectors, is cultivated
   b) optionally the expression of the esterase is induced, and
   c) optionally the esterase is isolated from the host organism and/or the culture medium.

Another object of the invention relates to the use of one of the aforementioned esterases, one of the aforementioned vectors, or one of the aforementioned microorganisms for carrying out one of the aforementioned methods of ester hydrolysis, or for the corresponding transesterification of said polyacrylic acid esters.

Another object of the invention relates to a polymeric reaction product, which is obtainable by one of the aforementioned methods.

III. Further Information Regarding Carrying Out of the Invention

1. Method for the Enzyme-Catalyzed Hydrolysis of Polyacrylic Acid Esters

The method according to the invention relates to an enzyme-catalyzed hydrolysis of polyacrylic acid esters, which in this text is also called enzymatic ester cleavage (or briefly: ester cleavage).

Within the scope of the method according to the invention, the preparation of at least one polyacrylic acid ester and its incubation with at least one esterase are envisaged. Preparation preferably takes place in a solution, which can be an aqueous solution, an organic solution (comprising one or more organic solvents) or aqueous-organic solution (with the organic solvent component comprising one or more organic solvents). The organic solvents that can be used include for example alcohols, such as methanol, ethanol, propanol, isopropanol and butanol, aromatic hydrocarbons, such as benzene and toluene, ethers, such as dimethyl ether, diethyl ether, 1,2-dimethoxyethane, and tetrahydrofuran. Aqueous solutions or aqueous-organic solutions are preferred. In an aqueous-organic solution, the organic solution or the sum of the organic solvent components can represent a proportion by volume from 1 to 80 vol. %, preferably from 10 to 60 vol. %, and in particular about 40 vol. %. The aqueous-organic solutions or organic-aqueous solutions can be, within the scope of the invention, homogeneous solutions, or two- or multiphase systems (for example oil-in-water, water-in-oil, water-in-oil-in-water emulsions). To permit easy contact between enzyme and polyacrylic acid ester, the solutions are preferably not gel-like. The solutions preferably have viscosities of less than 4000 mPa*s, in particular less than 2000 mPa*s, less than 1000 mPa*s, less than 500 mPa*s, less than 400 mPa*s, less than 200 mPa*s, less than 100 mPa*s, less than 50 mPa*s, less than 25 mPa*s, less than 10 mPa*s, less than 5 mPa*s or less than 2.5 mPa*s. The aqueous solution or the aqueous component of an aqueous-organic solution can be a buffer. The pH of the buffer is preferably adjusted to the pH at which the enzyme-catalyzed ester cleavage is to take place. If the method according to the invention is carried out in a bioreactor, in which microorganisms that produce at least one esterase, which cleaves the at least one polyacrylic acid ester, then the pH is preferably adjusted to a value suitable for the cultivation of the microorganism. A person skilled in the art is familiar with the determination of suitable pH values. Suitable buffers for use in the method according to the invention are also known by a person skilled in the art and comprise for example PBS, Tris-HCl buffer, triethanolamine hydrochloride/NaOH buffer, diethanolamine/HCl buffer, sodium borate/HCl buffer, glycine/NaOH buffer, sodium carbonate/sodium bicarbonate buffer, $Na_2HPO_4$/NaOH buffer, 2-(cyclohexylamino)ethanesulfonic acid/NaOH buffer and 3-(cyclohexylamino)-1-propanesulfonic acid/NaOH buffer. Other buffer systems are known by a person skilled in the art, and are described for example in Harris and Angal (Eds.), Protein purification methods—a practical approach, IRL Press at Oxford University Press, 1st edition (reprint) 1990.

The method according to the invention can be carried out at all temperatures at which the esterases used are active, for example at temperatures from 5° C. to 85° C., preferably from 10° C. to 50° C., especially preferably from 20° C. to 40° C. A person skilled in the art is familiar with the fact that enzymes have optimal temperatures with respect to their stability and/or their catalytic activity, which may possibly also vary depending on the solvent or solvent mixture used, and can determine the optimum temperature or the optimum temperature range for each esterase used. If the method according to the invention is carried out using microorganisms that produce the at least one esterase that is used for the hydrolytic cleavage of the polyacrylic acid ester, then the temperature requirements of the microorganisms can also be taken into account by a person skilled in the art when selecting the process temperature.

The polyacrylic acid esters prepared can be esterified completely (i.e. each acrylic acid group is esterified with an alcohol or alcohol derivative) or esterified partially (i.e. there are still free acrylic acid groups in the molecule of the polyacrylic acid ester). According to preferred embodiments the polyacrylic acid ester prepared or the polyacrylic acid esters prepared is/are esterified completely or substantially completely. Esterification is substantially complete when at least 75%, in particular at least 80%, at least 85%, at least 90%, at least 95%, at least 96%, at least 97%, at least 98% or at least 99% of the acrylic acid groups of the polyacrylic acid have been esterified. Accordingly, substantially completely esterified polyacrylic acid esters have for example degrees of esterification of 75% to 100%, 75% to 99%, 75% to 98%, 75% to 97%, 75% to 96%, 75% to 95%, 85% to 100%, 85% to 99%, 85% to 98%, 85% to 97%, 85% to 96%, 85% to 95%, 90% to 100%, 90% to 99%, 90% to 98%, 90% to 97%, 90% to 96%, 90% to 95%, 95% to 100%, 95% to 99%, 95% to 98%, 95% to 97% or 95% to 96%.

The method according to the invention can take place in batch mode, or continuously. In batch mode, the at least one polyacrylic acid ester and the at least one esterase are prepared, incubation is carried out and at a chosen point of time the reaction mixture is discharged from the reaction vessel and optionally sent for further processing (for example isolation of the reaction product or recovery of the at least one esterase). Discharge can take place after completion of ester cleavage (i.e. after establishment of an equilibrium between polyacrylic acid ester on the one hand and polyacrylic acid or partially esterified polyacrylic acid on the other hand) or after incomplete ester cleavage. The suitable point of time for discharge of the respective batch can be determined by a person skilled in the art by various methods, for example by prior sampling and analysis, or by continuous monitoring of the course of reaction on the basis of suitable parameters, for example the pH or the viscosity of the solution, which vary as ester cleavage progresses. The batch can optionally also be discharged at the end of a predetermined reaction time. In batch mode, after initial provision of the at least one polyacrylic acid ester and the at least one esterase, before final discharge of the reaction mixture, a single or multiple further addition of polyacrylic acid ester and/or esterase can take place independently of one another. In continuous mode, after the initial provision of the at least one polyacrylic acid ester and the at least one esterase, at specified points of time a portion of the reaction mixture is discharged and the reaction mixture remaining in the reaction vessel is supplemented by adding polyacrylic acid ester and/or esterase. The time points can be periodical or can be selected depending on measurements of the course of reaction. Continuous addition of the at least one polyacrylic acid ester and/or of the at least one esterase is also possible. Independently of this, continuous discharge of the reaction mixture is also possible. A person skilled in the art knows how to optimize the individual process variables (e.g. amount and point of time of addition or discharge), in order to obtain the desired reaction product. Continuous operation can take place for different lengths of time, for example for hours, days, weeks, months or years, and can be interrupted or halted, for example for cleaning, inspection or maintenance.

If isolation of the modified polymer obtained as a result of ester cleavage is envisaged, this can take place by the methods usually employed in this field, for example by chromatographic methods, dialysis, chemical precipitation, solvent extraction or evaporation of the solvent contained in the reaction mixture. If the at least one esterase is to be reused, it can be separated by the methods usually employed in this field, preferably before isolation of the modified polymer takes place by methods that may possibly damage the enzyme. The esterase can be separated for example by affinity purification by means of esterase-binding molecules (for example antibodies), dialysis or precipitation (for example with ammonium sulfate). According to further embodiments the at least one esterase is present in immobilized form. Various methods of immobilization are known by a person skilled in the art, and are described for example in S. Fukui, A. Tanaka, "Enzymes", in: Ullmann's Encyclopedia of Industrial Chemistry, 5th edition, Wiley-VCH, New York, Berlin, 1985; J. E. Prenosil, O. M. Kut, I. J. Dunn, E. Heinzle, "Immobilized Biocatalysts", in: Ullmann's Encyclopedia of Industrial Chemistry, 6th edition, VCH, New York, Berlin, 2003, p. 503-554; J. F. Kennedy, J. M. S. Cabral, in: H. J. Rehm, G. Reed (Eds.), Biotechnology: A comprehensive treatise in 8 volumes; Vol. 7a, p. 349-404; VCH, Weinheim, 1987. A noncovalent binding of the enzyme can for example be achieved by labeling the enzyme with biotin and immobilization on a support provided with avidin or streptavidin, labeling of the enzyme by incorporating histidine tags in its amino acid sequence and immobilization on a support provided with nickel chelate, immobilization of the enzyme by antibodies directed against the enzyme (the binding epitopes preferably being selected so that the binding between antibody and binding epitope does not, or does not substantially, impair access of substrate molecules to the active site), production of fusion proteins from the enzyme and a foreign protein and immobilization of the protein by antibodies directed against the foreign protein, or by adsorptive adhesion on microspheres (beads) or on carrier materials. As a result of immobilization, the esterase molecules remain stationary in the reaction vessel (for example on the walls of the reaction vessel or on surfaces present in the reaction vessel) and during discharge of the reaction mixture, only the polyacrylic acid esters and/or the polymers modified by ester cleavage are discharged. Alternatively, in the case of adhesion on microspheres, the esterase molecules can be freely floating in the reaction solution and can interact with the polyacrylic acid ester molecules, but are prevented by various means (for example filters or the use of fluidized-bed reactors) from leaving the reaction vessel together with the polyacrylic acid ester molecules and/or the polyacrylic acid molecules. Discharge of the microspheres together with the polyacrylic acid ester molecules and/or the polyacrylic acid molecules and subsequent separation, for example by centrifugation or filtration, is also possible.

The method according to the invention can be carried out until partial or complete hydrolytic cleavage of the ester groups contained in the polyacrylic acid ester has occurred, and in the case of complete hydrolysis, polyacrylic acid would be obtained. Discharge after partial hydrolysis is preferred. In this case the initially supplied polyacrylic acid esters still contain ester groups, which endowed the polymers modified in the course of the reaction with certain properties. The modified polymer can then be used for further purposes, for example as starting substances for further chemical modifications.

2. Enzymes

In the method according to the invention it is possible to use esterases in general, and in particular enzymes that act on ester bonds, of EC class 3.1 according to the classification of the "Nomenclature Committee of the International Union of Biochemistry and Molecular Biology". The classification of the EC classes is given in "Enzyme Nomenclature", published in 1992 by Academic Press for the International Union of Biochemistry and Molecular Biology" under ISBN 0-12-227164-5, with subsequent supplements, or online on the Internet at chem.qmul.ac.uk/iupac/jcbn/index.html#6. Preferred embodiments are carboxylic acid ester hydrolases (E.C. 3.1.1), in particular carboxyl esterases (E.C. 3.1.1.1), triacylglycerol lipases (E.C. 3.1.1.3) and cutinases (E.C. 3.1.1.74).

For the methods according to the invention, it is also possible to use "functional mutants" (also called "functional esterase mutants", "esterase mutants" or "mutants") of the concretely disclosed esterases, with the functional mutants, optionally after isolation from a microorganism producing these, themselves being an object of the invention. Within the scope of the present invention, functional mutants are polypeptides that differ from the concretely disclosed esterases, e.g. those that are less than 100% identical to the esterases according to SEQ ID NO:1 to SEQ ID NO:38 (for Example 40% to less than 100%, 50% to less than 100%, 60% to less than 100%, 75% to less than 100%, 85% to less than 100%, 90% to less than 100%, 95% to less than 100% or 99% to less than 100%), but which still possess the desired enzyme activity. The desired enzyme activity can for example be detected by cleavage of polyacrylic acid esters, for example polyacrylic acid methyl esters or polyacrylic acid butyl esters. The desired enzyme activity is regarded as present if the functional mutant has at least 10% of the cleavage activity of the esterase (which can be determined for example as conversion of the substrate in unit time), taken as reference, in particular at least 20%, at least 30%, at least 40%, at least 50%, at least 60%, at least 70%, at least 80%, at least 90%, at least 95% or 100% of said cleavage activity. The desired enzyme activity is of course in particular also present if the functional mutant has a higher cleavage activity than the esterase taken as reference, for example up to 105%, 110%, 120%, 150%, 200% or more than 200% of the cleavage activity of the esterase in question. Furthermore, it is also present if the functional mutant is able to cleave a new substrate, i.e. a polyacrylic acid ester that is not, or under comparable reaction conditions (for example temperature, pH, solvent or solvent composition, salt concentration, substrate concentration, enzyme concentration) is not, cleaved by the esterase taken as reference.

"Functional mutants" means, according to the invention, in particular altered proteins, which in at least one of the sequence positions of the aforementioned concrete sequences, have a different amino acid than that concretely stated, but nevertheless possess the desired enzyme activity. "Functional mutants" therefore comprise the altered proteins obtainable by one or more, e.g. 1-50, 1-40, 1-30, or 1-20, i.e. for example 1, 2, 3, 4, 5, 6, 7, 8, 9, 10, 11, 12, 13, 14, 15, 16, 17, 18, 19, 20 amino acid additions, substitutions, deletions and/or inversions, and the stated changes can occur in any sequence position, provided they lead to a functional mutant with the profile of properties according to the invention. Functional mutants are in particular also present when the pattern of reactivity between mutant and unaltered polypeptide coincides qualitatively, i.e. for example the enzymatic parameters (for example substrate affinity, turnover number) are identical, but quantitatively are present to different degrees. Examples of suitable substitutions of amino acid residues are as follows:

| Original residue | Examples of substitution |
|---|---|
| Ala | Val, Gly, Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Functional mutants" in the above sense are also precursors of the esterases described and functional derivatives and salts of the esterases. The term "salts" means salts of carboxyl groups as well as salts of acid addition of amino groups of the protein molecules according to the invention. Salts of carboxyl groups can be prepared in a manner known per se and comprise inorganic salts, for example sodium, calcium, ammonium, iron and zinc salts, and salts with organic bases, for example amines, such as triethanolamine, arginine, lysine, piperidine and the like. Salts of acid addition, for example salts with mineral acids, such as hydrochloric acid or sulfuric acid and salts with organic acids, such as acetic acid and oxalic acid, are also covered by the invention. "Functional derivatives" of esterases described in the invention or functional esterase mutants according to the invention can also be prepared on functional amino acid sides groups or at their N- or C-terminal ends by known techniques. Derivatives of this kind comprise for example aliphatic esters of carboxylic acid groups, amides of carboxylic acid groups, obtainable by reaction with ammonia or with a primary or secondary amine; N-acyl derivatives of free amino groups, prepared by reaction with acyl groups; or O-acyl derivatives of free hydroxyl groups, prepared by reaction with acyl groups.

"Functional mutants" naturally also comprise esterases that are accessible from other organisms, and naturally occurring variants. For example regions of homologous sequence regions can be found by sequence comparisons and, on the basis of the concrete guidelines of the invention, functional mutants can be determined. Examples of organisms are *Burkholderia* (for example *B. gladioli, B. mallei, B. pseudomallei, B. thailandensis, B. cenocepacia, B. aurantiaca, B. vietnamensis, B. dolosa, B. multivorans, B. ambi-*

*faria*), *Stigmatella* (for example *S. aurantiaca*), *Streptomyces* (for example *S. ambofaciens, S. coelicolor*), *Saccharopolyspora* (for example *S. erythraea*), *Mycobacterium* (for example *M. smegmatis, M. bovis, M. tuberculosis, M. leprae*).

"Functional mutants" are moreover fusion proteins, which have one of the aforementioned polypeptide sequences of esterases or functional mutants derived therefrom and at least one further, functionally different therefrom, heterologous sequence in functional N- or C-terminal linkage (i.e. without mutual, substantial functional impairment of the fusion protein portions). Nonlimiting examples of heterologous sequences of this kind are e.g. enzymes, protein A and immunoglobulins, it being possible for protein A and immunoglobulin fusions to be used for example for noncovalent immobilization of the functional mutants on supports (for example microspheres).

Furthermore, methods of production of functional mutants are known by a person skilled in the art. Methods for modifying genes and therefore for modifying the proteins encoded by these have long been familiar to a person skilled in the art, for example site-directed mutagenesis, in which there is targeted exchange of individual or several nucleotides of a gene (Trower M K (ed.) 1996; In vitro mutagenesis protocols. Humana Press, New Jersey), saturation mutagenesis, in which a codon for any desired amino acid can be exchanged or added at any point of a gene (Kegler-Ebo D M, Docktor C M, DiMaio D (1994) Nucleic Acids Res 22:1593; Barettino D, Feigenbutz M, Valcárel R, Stunnenberg H G (1994) Nucleic Acids Res 22:541; Barik S (1995) Mol Biotechnol 3:1), error-prone polymerase chain reaction (error-prone PCR), in which nucleotide sequences are mutated by defectively operating DNA polymerases (Eckert K A, Kunkel T A (1990) Nucleic Acids Res 18:3739); passaging of genes in mutator strains, in which there is an increased mutation rate of nucleotide sequences, for example owing to defective DNA repair mechanisms (Greener A, Callahan M, Jerpseth B (1996) An efficient random mutagenesis technique using an *E. coli* mutator strain. In: Trower M K (ed.) In vitro mutagenesis protocols. Humana Press, New Jersey), or DNA shuffling, in which a pool of closely related genes is formed and digested and the fragments are used as template for a polymerase chain reaction, in which by repeated strand separation and bringing together again, full-length mosaic genes are finally produced (Stemmer W P C (1994) Nature 370:389; Stemmer W P C (1994) Proc Natl Acad Sci USA 91:10747). Depending on the technology used, a person skilled in the art can insert completely random or also more targeted mutations into genes or also noncoding nucleic acid regions (which for example are important for the regulation of expression) and then set up gene banks. The methods of molecular biology required for this are known by a person skilled in the art and for example are described in Sambrook and Russell, Molecular Cloning. 3rd edition, Cold Spring Harbor Laboratory Press 2001.

Using so-called directed evolution (described inter alia in Reetz M T and Jaeger K-E (1999), Topics Curr Chem 200:31; Zhao H, Moore J C, Volkov A A, Arnold F H (1999), Methods for optimizing industrial enzymes by directed evolution, in: Demain A L, Davies J E (Eds.) Manual of industrial microbiology and biotechnology. American Society for Microbiology), a person skilled in the art can also produce functional mutants in a targeted manner and on a large scale. In this, in a first step, gene banks of the respective proteins are first produced, for example employing the methods mentioned above. The gene banks are expressed in a suitable manner, for example by bacteria or by phage display systems. Moreover, methods are known by a person skilled in the art for controlling, by the choice of suitable expression vectors, the localization of the protein in the host, for example as intracellular proteins in the cytoplasm, as membrane protein by adding-on a membrane anchor, or as extracellular protein by adding-on a signal peptide with recognition site for a signal peptidase. Then in a second step, clones that express proteins with a desired property are selected or screened. During selection, only the clones that express proteins with desired properties survive, as these provide the host organisms with a survival advantage (for example enzymes that enable certain substrates to be utilized, or growth at certain temperatures). During screening, all clones survive, so that suitable assays are used for determining which one of the clones expresses a protein with the desired property. A person skilled in the art knows how assays can be suitably set up for the particular purpose. For example, when searching for proteins with specified binding properties, it is possible to screen for host organisms that express the proteins in question on their surface and adhere to a substrate coated with the binding partner (in contrast to host organisms that do not express functional proteins); when searching for functional mutants with catalytic properties, host organisms can for example be cultivated in microtiter plates with substrate-containing medium or on substrate-containing agar plates and the presence of functional mutants (optionally after lysis of the host organisms, to permit contact with the medium) can be indicated for example by color reactions after reaction of the substrate. In this connection it is possible to use automated systems (e.g. pipeting robots for microtiter plates, screening robots, image recognition systems for identifying colonies on agar plates), to make high-throughput screening possible. The relevant genes of host organisms that express functional mutants with properties that largely correspond to the desired properties are submitted to another round of mutation. The steps of mutation and of selection or screening can, on the other hand, be repeated iteratively until the functional mutants that are present have the desired properties to a sufficient degree.

Using an iterative procedure it is possible to conduct targeted screening for proteins with desired properties, although the insertion of many mutations into a protein sequence is more likely to lead to the loss of a function than to the acquisition or improvement of a desired function. Within the scope of the iterative procedure, we start from a reference protein, for example a wild-type protein, and prepare, on the basis of its nucleotide sequence, a gene library with mutations. For this, the mutation rate is selected at the nucleotide level so that following expression of the mutated nucleic acids, only a relatively small number of amino acids in the translated peptides or proteins have been mutated, for example 1 to 3 amino acids. The mutated peptides or proteins obtained are screened for representatives with desired properties (for example a higher catalytic activity for one or more substrates, an expanded or altered substrate spectrum, improved stability at increased or altered temperatures or pH values or in certain solvents). On the basis of the sequences of peptides or proteins found with the desired properties (which possibly are only slight), a second gene library is constructed, in which once again a relatively small rate of mutations is introduced, and the proteins translated from it are again screened for the desired property. This cycle of constructing a mutated gene library and screening of the peptides or proteins expressed from it for desired properties can be repeated as often as required. On the one hand, because of the low mutation rate used per cycle, it is avoided that practically all proteins have a loss of function because of too many mutations in their amino acid sequence, and on the other hand, through iterative repetition of mutation and selection, favorable mutations are accumulated and so finally there is a good prospect of success in preparing proteins that have the desired, greatly improved properties. Furthermore, through sequence analysis of mutants with improved properties, a person skilled in the art obtains sequence information that indicates to him which sequence positions or sequence regions of a peptide or protein are important for a desired property. Based on this information, he can intentionally put mutations at these sites or in these regions and accordingly obtain even more targeted mutants with desired properties. Examples in the literature for the production of proteins with desired properties, from which the relevant methods of production of mutations can also be seen, are described in Zhao and Arnold, Protein Engineering 12:47-53 (1999) or May et al., Nature Biotechnology 18:317-320 (2000).

Other "functional mutants" included according to the invention are homologs of the concretely disclosed esterases. These possess at least 40% or at least 50%, or at least 60%, e.g. at least 75% or in particular at least 85%, e.g. 90%, 95% or 99%, homology to one of the concretely disclosed sequences, e.g. calculated according to the algorithm of Pearson and Lipman, Proc. Natl. Acad, Sci. (USA) 85(8), 1988, 2444-2448. A percentage homology of a homologous polypeptide according to the invention means in particular the percentage identity of the amino acid residues relative to the total length of one of the amino acid sequences concretely described herein.

A "derived" amino acid sequence means according to the invention, if no other information is given, a sequence that has identity with the starting sequence of at least 80% or at least 90%, in particular about 91%, 92%, 93%, 94%, 95%, 96%, 97%, 98% and 99%. For example, the invention relates to the amino acid sequences derived from all amino acid sequences disclosed here.

"Identity" or "homology" between two sequences means identity of the amino acid residues over the whole sequence length in each case, e.g. the identity that is calculated by comparison using the Vector NTI Suite 7.1 Software from the company Informax (USA) using the clustal method (Higgins D G, Sharp P M. Fast and sensitive multiple sequence alignments on a microcomputer. Comput Appl. Biosci. 1989 April; 5(2): 151-1) on setting the following parameters:

Multiple Alignment Parameters:

| | |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |

Pairwise Alignment Parameters:

| | |
|---|---|
| FAST algorithm | on |
| K-tuplesize | 1 |
| Gap penalty | 3 |
| Window size | 5 |
| Number of best diagonals | 5 |

These values can be varied further if necessary by a person skilled in the art in relation to the concrete sequences to be compared.

In the case of a possible protein glycosylation, the functional mutants according to the invention comprise proteins of the type designated above in deglycosylated or glycosylated form and modified forms obtainable by altering the glycosylation pattern.

Homologs of the esterases described or of their functional mutants according to the invention can be identified by screening combinatorial banks of mutants, e.g. shortened mutants. For example, a bank of peptide variants can be produced by combinatorial mutagenesis at the nucleic acid level, e.g. by enzymatic ligation of a mixture of synthetic oligonucleotides. There are many methods that can be used for the production of banks of potential homologs from a degenerated oligonucleotide sequence. The chemical synthesis of a degenerated gene sequence can be carried out in an automatic DNA synthesizer, and the synthetic gene can then be ligated into a suitable expression vector. The use of a degenerated set of genes makes it possible to provide all sequences in one mixture, which encode the desired set of potential protein sequences. Methods of synthesis of degenerated oligonucleotides are known by a person skilled in the art (e.g. Narang, S. A. (1983) Tetrahedron 39:3; Itakura et al. (1984) Annu. Rev. Biochem. 3:323; Itakura et al. (1984) Science 198:1056; Ike et al. (1983) Nucleic Acids Res. 11:477).

Within the scope of the research forming the basis of the present invention, the inventors found, surprisingly, that ester bonds of polyacrylic acid esters, i.e. polymer substrates, can be cleaved by esterases. Esterases from various organisms can be used, and the following may be mentioned as nonlimiting examples: *Burkholderia* (for example *B. gladioli, B. mallei, B. pseudomallei, B. thailandensis, B. cenocepacia, B. aurantiaca, B. vietnamensis, B. dolosa, B. multivorans, B. ambifaria*), *Stigmatella* (for example *S. aurantiaca*), *Streptomyces* (for example *S. ambofaciens, S. coelicolor*), *Saccharopolyspora* (for example *S. erythraea*), *Mycobacterium* (for example *M. smegmatis, M. bovis, M. tuberculosis, M. leprae*).

Esterases that are preferred for carrying out the method according to the invention are enzymes that act on ester bonds in EC class 3.1, in particular carboxylic acid ester hydrolases (EC 3.1.1). Carboxyl esterases, triacylglycerol lipases and cutinases are especially preferred. Esterases of family VIII (in particular esterase B from *Burkholderia gladioli* according to SEQ ID NO:1 and functional mutants thereof) and type C esterases (in particular esterase C from *Burkholderia gladioli* according to SEQ ID NO:2 and functional mutants thereof) represent further special embodiments. Other, nonlimiting examples of usable esterases are the sequences according to SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, on the basis of which functional mutants can in their turn be produced or derived.

Within the scope of the present invention, furthermore, functional mutants of known esterases were therefore produced, which can also be used in the method according to the invention and furthermore—optionally after isolation from a microorganism producing the functional mutants—are themselves also covered by the invention.

These functional mutants relate in particular to esterases with an altered amino acid sequence relative to the known wild type, with a new esterase being provided by the altered sequence, with which optionally the access of polymer substrates to the catalytically active site is made possible or is facilitated, and/or the stability of the esterase is increased, for example the stability at certain pH values or in various solvents or solvent mixtures are covered by the invention, therefore among other things functional mutants of esterases, in which structural elements are altered or removed, which prevent or impede the access of substrates to the active site, for example loops. Suitable regions for loop shortening in the case of an esterase according to SEQ ID NO:1 (EstB from *B. gladioli*) are for example the regions Glu246 to Arg 258 and Gly312 to 323. In this case loop shortenings can be carried out by removing one or more amino acids, and in the case of removal of several amino acids, once again one or more amino acids with adjacent or nonadjacent location in SEQ ID NO:1 can be removed. The invention relates furthermore to functional mutants of esterases, in which the access to the catalytically active site (also called active center), which can for example be of tunnel, funnel, furrow or crevice shape, was made more accessible for molecules from the surroundings of the esterase. This can take place for example by removing amino acids with large side chains, which are a constituent of the access to the catalytically active site, or replacing them with amino acids with smaller side chains (for example alanine with glycine, valine with alanine or glycine, leucine with valine, etc.). As a result the spatial access of partial regions of polyacrylic acid esters, which are macromolecules with large space filling, to the catalytic center is made possible or facilitated. Regarding the charging of polyacrylic acid esters, which can have a negative charge because there are still free carboxyl groups, this can moreover take place by exchange of acidic amino acids in the access region of the active site for neutral or basic amino acids. With regard to polyacrylic acid esters, which for example because of alcohol constituents of the ester substituted with basic groups can rather have a positive charge, the access to the catalytically active site can correspondingly be made possible or facilitated by exchange of basic amino acids in the access region of the catalytically active site for less basic, optionally neutral or acidic amino acids. For example, suitable amino acids, exchange of which for amino acids with smaller side chains should improve the access to the active site, are Tyr181, Trp348 and Trp149 in the case of SEQ ID NO:1. For SEQ ID NO:2, for example Leu163, Val213 and Pro168 are possibilities for this, and especially in the case of Pro168, exchange for Ala or Gly can also increase the flexibility of the associated loops, so that a larger substrate can be allowed. The invention further relates to functional mutants of esterases with increased stability, for example increased pH, temperature or solvent stability. This increased stability can for example be achieved by amino acid exchanges, with which intramolecular interactions within a protein molecule become possible for the first time or are intensified, by which there is better fixation of unstable loops of the protein molecule, or individual protein domains acquire better cohesion.

Accordingly, special embodiments of the present invention are functional mutants of EstB according to SEQ ID NO:1, in which loops positioned above the catalytically active site were removed or shortened by more or less complete deletion of the loop-forming amino acids. FIG. 1 shows a molecular model of EstB according to SEQ ID NO:1, in which two loops were identified, which lie between the catalytically active site and the external medium of the EstB.

Figure 2:
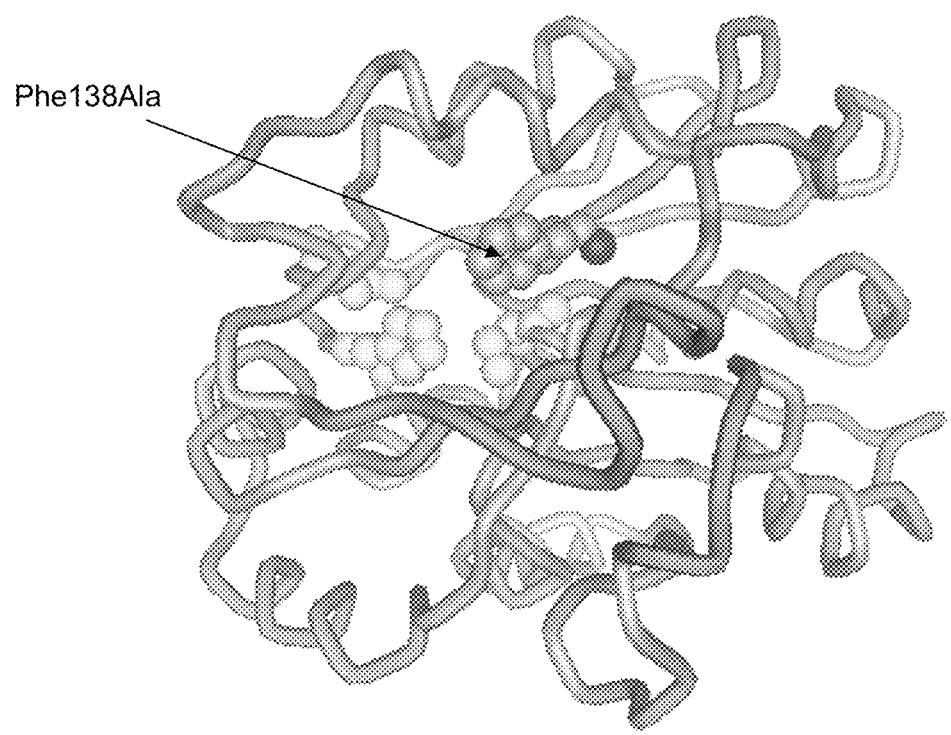
FIG. 2 shows a structural model of EstC according to SEQ ID NO:2, with phenylalanine 138 replaced with alanine (Phe138Ala; corresponding to the mutant 1K22 in FIG. 5). The backbone of the polypeptide chain is shown. The amino acid phenylalanine in position 138, marked with an arrow, is represented as a space-filling model, the amino acids given in the illustration below Phe138 as space-filling model correspond to the amino acids Ser112, Asp242 and His275 belonging to the catalytically active center.
Figure 3:
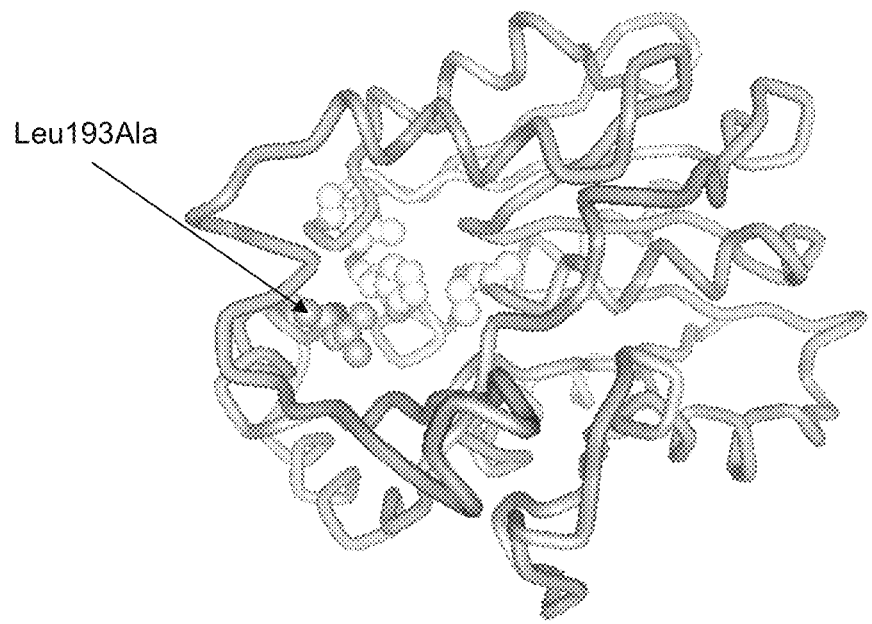
FIG. 3 shows a structural model of EstC according to SEQ ID NO:2, with leucine 193 replaced with alanine (Leu193Ala; corresponding to the mutant 2K20 in FIG. 5). The backbone of the polypeptide chain is shown. The amino acid leucine in position 193, marked with an arrow, is represented as a space-filling model, the amino acids given in the illustration above Leu193 as space-filling model correspond to the amino acids Ser112, Asp242 and His275 belonging to the catalytically active center.
Figure 4:
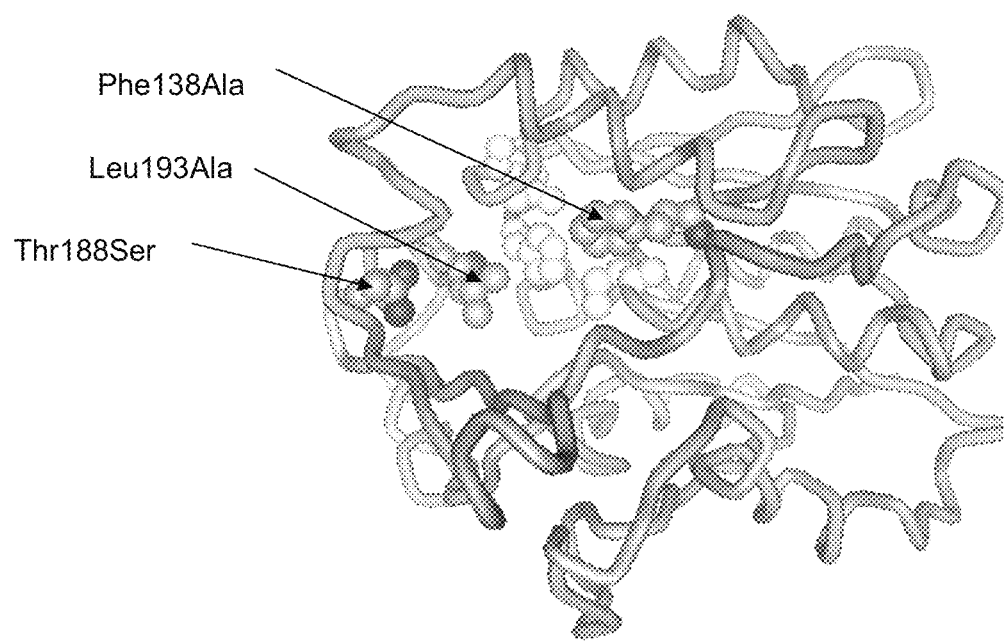
FIG. 4 shows a structural model of EstC according to SEQ ID NO:2, with phenylalanine 138 replaced with alanine, leucine 193 with alanine, and threonine 188 with serine (Phe138Ala, Leu193Ala, Thr188Ser; corresponding to mutant B48 in FIG. 5). The backbone of the polypeptide chain is shown. The amino acids Phe138, Thr188 and Leu193 represented as a space-filling model are marked with an arrow. The other amino acids given as a space-filling model correspond to the amino acids Ser112, Asp242 and His275 belonging to the catalytically active center.

Further special embodiments of the present invention are accordingly functional mutants of EstC according to SEQ ID NO:2. Within the scope of the present invention, a structural model of EstC was used, on the basis of which functional mutants were produced. In this connection, the inventors identified protein regions that line the access to the catalytically active site. Next, by site-directed mutagenesis, individual or several amino acids of SEQ ID NO:2 were intentionally altered, in order to widen the access and provide better access for large, polymeric substrates. Phe138 (i.e. the phenylalanine on amino acid position 138) was identified as an amino acid lining the access to the active site (FIG. 2). It can be seen from FIG. 2 that Phe138 is positioned with its side chain between the amino acids Ser112, Asp242 and His275 of the catalytically active site and the external medium of the protein. By replacing Phe138 with alanine (Phe138Ala), in view of the smaller side group of alanine, the access of bulky substrate molecules, for example polyacrylic acid esters, to the catalytically active site is facilitated (corresponding to mutation 1K22 in FIG. 5). The physicochemical properties of the protein surface at position 138 remain essentially the same, as a hydrophobic amino acid is replaced with another hydrophobic amino acid. According to the invention, Leu193 was identified as another amino acid hampering access to the catalytically active site (FIG. 4), and in one embodiment was replaced with alanine (corresponding to mutation 2K20 in FIG. 5). Another example that may be mentioned is Thr188, which is located at the margin of the access to the catalytically active site and can still influence the access of substrate molecules to a certain extent (FIG. 4). According to one embodiment, Thr188 is replaced with serine, for example in the triple mutation Phe138Ala, Leu193Ala, Thr188Ser (FIG. 4). The invention covers any combinations of these or of the mutations shown in FIG. 5. A person skilled in the art is able, using the procedure described here, to determine suitable positions for amino acid exchange also in the case of proteins homologous to EstC. For example, using the "Tripos" software from Sybly (St. Louis, Mo., USA) he is able to superimpose the structure of EstC disclosed here and an esterase with similar 3D structure and then determine suitable positions, so that the present invention is not limited to the proteins and mutations concretely disclosed here.

3. Nucleic Acids

The invention further relates to the coding nucleic acid sequences for the functional esterase mutants described above, such as in particular according to SEQ ID NO:54 to SEQ ID NO:57.

All nucleic acid sequences according to the invention (single-stranded and double-stranded DNA and RNA sequences, e.g. cDNA and mRNA) can be produced in a manner known per se by chemical synthesis from the nucleotide building blocks, for example by fragment condensation of individual overlapping, complementary nucleic acid building blocks of the double helix. The chemical synthesis of oligonucleotides can take place for example, in a known way, by the phosphoroamidite method (Voet, Voet, 2nd edition, Wiley Press New York, pages 896-897). The adding-on of synthetic oligonucleotides and filling of gaps using the Klenow fragment of DNA polymerase and ligation reactions and general cloning methods are described in Sambrook et al. (1989), Molecular Cloning: A laboratory manual, Cold Spring Harbor Laboratory Press.

A "derived" nucleic acid sequence means according to the invention, unless stated otherwise, a sequence that has identity with the starting sequence of at least 80% or at least 90%, in particular about 91%, 92%, 93%, 94%, 95%, 96%, 97%, 98% and 99%. The invention relates for example to all nucleic acid sequences derived from the nucleic acid sequences disclosed here.

"Identity" between two nucleic acids means identity of the nucleotides in each case over the full length of the nucleic acid, in particular the identity that is determined by comparison using the Vector NTI Suite 7.1 Software from the company Informax (USA) using the clustal method (see above).

The invention also relates to nucleic acid sequences coding for one of the above esterases and functional mutants thereof, which are accessible e.g. using artificial nucleotide analogs.

The invention relates both to isolated nucleic acid molecules, which code for esterases according to the invention or enzymatically active segments thereof, and nucleic acid fragments that can be used e.g. as hybridization probes or primers for identification or amplification of coding nucleic acids according to the invention.

The nucleic acid molecules according to the invention can moreover contain untranslated sequences from the 3'- and/or 5'-end of the coding gene region.

An "isolated" nucleic acid molecule is separated from other nucleic acid molecules that are present in the natural source of the nucleic acid and can moreover be substantially free of other cellular material or culture medium, if it is produced by recombinant techniques, or free from chemical precursors or other chemicals, if it is synthesized chemically.

A nucleic acid molecule according to the invention can be isolated by means of standard techniques of molecular biology and the sequence information provided according to the invention. For example, cDNA can be isolated from a suitable cDNA bank, using one of the complete sequences concretely disclosed or a segment thereof as hybridization probe and standard hybridization techniques (as described for example in Sambrook, J., Fritsch, E. F. and Maniatis, T. Molecular Cloning: A laboratory manual. 2nd edition, Cold Spring Harbor Laboratory, Cold Spring Harbor Laboratory Press, Cold Spring Harbor, N. Y., 1989). Moreover, a nucleic acid molecule, comprising one of the sequences according to the invention or a segment thereof, can be isolated by polymerase chain reaction, using the oligonucleotide primers that were prepared on the basis of this sequence. The nucleic acid thus amplified can be cloned into a suitable vector and can be characterized by DNA sequence analysis. The oligonucleotides according to the invention can moreover be produced by standard methods of synthesis, e.g. with an automatic DNA synthesizer.

The invention further comprises the nucleic acid molecules that are complementary to the concretely described nucleotide sequences, or a segment thereof.

The nucleotide sequences according to the invention make possible the production of probes and primers, which can be used for the identification and/or cloning of homologous sequences in other cell types and organisms. Such probes or primers usually comprise a nucleotide sequence region, which hybridizes under stringent conditions to at least about 12, preferably at least about 25, e.g. about 40, 50 or 75 successive nucleotides of a sense strand of a nucleic acid sequence according to the invention or a corresponding antisense strand.

Further nucleic acid sequences according to the invention are derived from coding sequences of the esterases according to the invention and differ from them by one or more, e.g. 1-50, 1-40, 1-30, or 1-20, i.e. for example 1, 2, 3, 4, 5, 6, 7, 8, 9, 10, 11, 12, 13, 14, 15, 16, 17, 18, 19, 20 additions, substitutions, insertions or deletions of individual or several nucleotides, but furthermore code for esterases with the desired enzyme activity.

The invention also relates to nucleic acid sequences that comprise so-called silent mutations or have been altered according to the codon usage of a special original or host organism, in comparison with a concretely stated sequence, as well as naturally occurring variants, e.g. splice variants or allele variants, thereof. It also relates to sequences obtainable by conservative nucleotide substitutions (i.e. the amino acid in question is replaced with an amino acid of the same charge, size, polarity and/or solubility).

The invention also relates to molecules derived by sequence polymorphisms from the concretely disclosed nucleic acids. These genetic polymorphisms can exist between individuals within a population due to natural variation. These natural variations usually bring about a variance of 1 to 5% in the nucleotide sequence of a gene.

Furthermore, the invention also comprises nucleic acid sequences that hybridize to the aforementioned coding sequences or are complementary to them. These polynucleotides can be found by inspecting genome or cDNA libraries and can optionally be amplified from them with suitable primers by means of PCR and then isolated for example with suitable probes. Another possibility is the transformation of suitable microorganisms with polynucleotides or vectors according to the invention, multiplication of the microorganisms and therefore of the polynucleotides and subsequent isolation thereof. Furthermore, polynucleotides according to the invention can also be synthesized chemically.

The property of being able to "hybridize" to polynucleotides means the capacity of a polynucleotide or oligonucleotide to bind under stringent conditions to an almost complementary sequence, whereas under these conditions nonspecific bindings between noncomplementary partners do not occur. For this the sequences should be complementary to 70-100%, in particular to 90-100%, e.g. 95%, 96%, 97%, 98% or 99%. The property of complementary sequences of being able to bind specifically to one another is utilized for example in Northern or Southern blotting or in primer binding in PCR or RT-PCR. Usually oligonucleotides starting from a length of 30 base pairs are used for this. "Under stringent conditions" means, for example in Northern blotting, the use of a washing solution at a temperature of 50-70° C., preferably 60-65° C., for example 0.1×SSC buffer with 0.1% SDS (20×SSC: 3M NaCl, 0.3M Na-citrate, pH 7.0), for elution of nonspecifically hybridized cDNA probes or oligonucleotides. As mentioned above, only highly complementary nucleic acids remain bound to one another. The establishment of stringent conditions is known by a person skilled in the art and is described e.g. in Ausubel et al., Current Protocols in Molecular Biology, John Wiley & Sons, N.Y. (1989), 6.3.1-6.3.6.

4. Expression Constructs and Vectors

The invention further relates to expression constructs, containing, under the genetic control of regulatory nucleic acid sequences, a nucleic acid sequence coding for an esterase according to the invention or a functional mutant; and vectors, comprising at least one of these expression constructs.

Preferably said constructs according to the invention comprise, 5'-upstream of the respective coding sequence, a promoter and, 3'-downstream, a terminator sequence and optionally other usual regulatory elements, in each case operatively linked to the coding sequence. "Operative linkage" means the sequential arrangement of promoter, coding sequence, terminator and optionally other regulatory elements in such a way that each of the regulatory elements can fulfill its function in expression of the coding sequence as defined. Examples of operatively linkable sequences are targeting sequences and enhancers, polyadenylation signals and the like. Other regulatory elements comprise selectable markers, amplification signals, replication origins and the like. Suitable regulatory sequences are described e.g. in Goeddel, Gene Expression Technology: Methods in Enzymology 185, Academic Press, San Diego, Calif. (1990).

In addition to the artificial regulatory sequences, the natural regulatory sequence can still be present in front of the actual structural gene. Through genetic variation, this natural regulation may possibly be switched off and the expression of the genes can be increased or reduced. The gene construct can, however, also be of simpler construction, i.e. no additional regulatory signals are inserted before the structural gene and the natural promoter with its regulation is not removed. Instead the natural regulatory sequence is mutated so that there is no longer any regulation and gene expression is increased or decreased. The nucleic acid sequences can be contained in the gene construct in one or more copies.

Examples of usable promoters are: cos-, tac-, trp-, tet-, trp-tet-, lpp-, lac-, lpp-lac-, lacIq-, T7-, T5-, T3-, gal-, trc-, ara-, SP6-, lambda-PR- or lambda-PL promoters, which advantageously find application in Gram-negative bacteria; and the Gram-positive promoters amy and SPO2, the yeast promoters ADC1, MFalpha, AC, P-60, CYC1, GAPDH or the plant promoters CaMV/355, SSU, OCS, lib4, usp, STLS1, B33, not or the ubiquitin or phaseolin promoter. The use of inducible promoters, e.g. light- and in particular temperature-inducible promoters, such as the $P_rP_l$-promoter, is especially preferred. In principle all natural promoters can be used with their regulatory sequences. Furthermore, synthetic promoters can also be used advantageously.

The aforementioned regulatory sequences should permit targeted expression of the nucleic acid sequences and of protein expression. This can mean for example, depending on the host organism, that the gene is only expressed or overexpressed after induction, or that it is expressed and/or overexpressed immediately.

The regulatory sequences or factors can preferably have a positive influence on expression and thus cause it to increase or decrease. Thus, a strengthening of the regulatory elements can advantageously take place at the transcription level, by using strong transcription signals such as promoters and/or "enhancers". In addition, however, an intensification of translation is also possible, for example with improvement of the stability of mRNA.

An expression cassette is produced by fusion of a suitable promoter with a suitable coding nucleotide sequence and a terminator or polyadenylation signal. Common recombination and cloning techniques are used for this, as described for example in T. Maniatis, E. F. Fritsch and J. Sambrook, Molecular Cloning: A laboratory manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

The recombinant nucleic acid construct or gene construct is inserted for expression in a suitable host organism, advantageously into a host-specific vector, which makes optimal expression of the genes in the host possible. Vectors are well known by a person skilled in the art and can be taken for example from "Cloning Vectors" (Pouwels P. H. et al., Eds., Elsevier, Amsterdam-New York-Oxford, 1985). Vectors are to be understood as, in addition to plasmids, also all other vectors known by a person skilled in the art, for example phages, viruses, such as SV40, CMV, baculovirus and adenovirus, transposons, IS elements, phasmids, cosmids, and linear or circular DNA. These vectors can be replicated autonomously in the host organism or can be replicated chromosomally.

As examples of suitable expression vectors we may mention:

Usual fusion expression vectors, such as pGEX (Pharmacia Biotech Inc; Smith, D. B. and Johnson, K. S. (1988) Gene 67:31-40), pMAL (New England Biolabs, Beverly, Mass.) and pRIT 5 (Pharmacia, Piscataway, N.J.), in which glutathione-S-transferase (GST), maltose E-binding protein or protein A are fused onto the recombinant target protein.

Non-fusion protein expression vectors such as pTrc (Amann et al., (1988) Gene 69:301-315) and pET 11d (Studier et al. Gene Expression Technology: Methods in Enzymology 185, Academic Press, San Diego, Calif. (1990) 60-89).

Yeast expression vector for expression in the yeast *S. cerevisiae*, such as pYepSec1 (Baldari et al., (1987) EMBO J. 6:229-234), pMFa (Kurjan and Herskowitz (1982) Cell 30:933-943), pJRY88 (Schultz et al. (1987) Gene 54:113-123) and pYES2 (Invitrogen Corporation, San Diego, Calif.). Vectors and methods of construction of vectors that are suitable for use in other fungi, such as filamentous fungi, include those that are described in detail in: van den Hondel, C. A. M. J. J. & Punt, P. J. (1991) "Gene transfer systems and vector development for filamentous fungi, in: Applied Molecular Genetics of Fungi, J. F. Peberdy et al., Eds., p. 1-28, Cambridge University Press: Cambridge.

Baculovirus vectors, which are available for expression of proteins in cultured insect cells (for example Sf9 cells), comprise the pAc series (Smith et al., (1983) Mol. Cell Biol., 3:2156-2165) and the pVL series (Lucklow and Summers (1989) Virology 170:31-39).

Plant expression vectors, such as those that are described in detail in: Becker, D., Kemper, E., Schell, J. and Masterson, R. (1992) "New plant binary vectors with selectable markers located proximal to the left border", Plant Mol. Biol. 20:1195-1197; and Bevan, M. W. (1984) "Binary *Agrobacterium* vectors for plant transformation", Nucl. Acids Res. 12:8711-8721.

Mammalian expression vectors, such as pCDM8 (Seed, B. (1987) Nature 329:840) and pMT2PC (Kaufman et al. (1987) EMBO J. 6:187-195).

Other suitable expression systems for prokaryotic and eukaryotic cells are described in chapters 16 and 17 of Sambrook, J., Fritsch, E. F. and Maniatis, T., Molecular Cloning: A laboratory manual, 2nd edition, Cold Spring Harbor Laboratory, Cold Spring Harbor Laboratory Press, Cold Spring Harbor, N. Y., 1989.

5. Recombinant Host Organisms

By means of the vectors according to the invention, recombinant organisms can be produced, which have for example been transformed with at least one vector according to the invention and can be used for the production of the domains or polypeptides according to the invention. Advantageously the recombinant constructs according to the invention, described above, are inserted into a suitable host system and expressed. Preferably, common cloning and transfection methods known by a person skilled in the art, for example co-precipitation, protoplast fusion, electroporation, chemical transformation, retroviral transfection and the like, are used in order to bring about expression of the stated nucleic acids in the particular expression system. Suitable systems are described for example in Current Protocols in Molecular Biology, F. Ausubel et al., Eds., Wiley Interscience, New York 1997, or Sambrook et al. Molecular Cloning: A laboratory manual. 2nd edition, Cold Spring Harbor Laboratory, Cold Spring Harbor Laboratory Press, Cold Spring Harbor, N. Y., 1989.

As host organisms, in principle all organisms are suitable that make possible expression of the nucleic acids according to the invention, their allele variants, their derivations, which code for functional mutants, or derivatives thereof. The host organisms are for example bacteria, fungi, yeasts, plant or animal cells. Preferred organisms are bacteria, such as those of the genera *Escherichia*, e.g. *Escherichia coli, Streptomyces, Bacillus, Pseudomonas* or *Burkholderia*, eukaryotic microorganisms, such as *Saccharomyces cerevisiae, Aspergillus*, higher eukaryotic cells from animals or plants, for example Sf9, CHO or HEK293 cells, and within the scope of the present invention, individual cells from higher eukaryotic life forms such as animals or plants or said cells that have aggregated or grown to form cell clusters, are also designated as microorganisms.

The selection of successfully transformed organisms can be effected by means of marker genes, which are also contained in the vector or in the expression cassette. Examples of said marker genes are genes for antibiotic resistance and for enzymes that catalyze a coloring reaction, which produces a staining or a fluorescence of the transformed cell. These can then be selected by automatic cell sorting. Microorganisms successfully transformed with a vector, which carry a corresponding antibiotic resistance gene (e.g. G418 or hygromycin), can be selected with media or culture nutrients containing the corresponding antibiotics. Marker proteins that are presented on the cell surface can be used for selection by means of affinity chromatography.

The invention further relates to methods for recombinant production of esterases according to the invention or functional, enzymatically active fragments thereof, by cultivating an esterase-producing recombinant host organism, optionally inducing expression of the esterase and isolating the latter from the culture. The esterase or the esterases can also be produced in this way on an industrial scale, if this is required.

The recombinant host can be cultivated and fermented by known methods. Bacteria can be grown for example in TB or LB medium and at a temperature from 20 to 40° C. and a pH from 6 to 9. Suitable culture conditions are described in detail for example in T. Maniatis, E. F. Fritsch and J. Sambrook, Molecular Cloning: A laboratory manual, Cold Spring Harbor Laboratory, Cold Spring Harbor, N.Y. (1989).

Then, if the esterases are not secreted in the culture medium, the cells are lysed and the product is obtained from the lysate by known protein isolation techniques. The cells can optionally be disrupted by high-frequency ultrasound, by high pressure, e.g. in a French pressure cell (French press), by osmolysis, by the action of detergents, lytic enzymes or organic solvents, by means of homogenizers or by a combination of several of the methods listed.

The esterases can be purified with known chromatographic methods, such as molecular sieve chromatography (gel filtration), such as Q-sepharose chromatography, ion exchange chromatography and hydrophobic chromatography, and with other usual methods such as ultrafiltration, crystallization, salting-out, dialysis and native gel electrophoresis. Suitable methods are described for example in Cooper, F. G., Biochemical Procedures, Verlag Walter de Gruyter, Berlin, New York or in Scopes, R., Protein Purification, Springer Verlag, New York, Heidelberg, Berlin.

It is especially suitable to use vector systems or oligonucleotides for isolating the recombinant esterase; these lengthen the cDNA by defined nucleotide sequences and therefore code for altered polypeptides or fusion proteins, which serve e.g. for simpler purification. Suitable modifications of this kind are for example so-called "tags", functioning as anchorages, e.g. the modification known as hexahistidine-anchor or epitopes that can be recognized as antigens by antibodies (described for example in Harlow, E. and Lane, D., 1988, Antibodies: A Laboratory Manual. Cold Spring Harbor (N.Y.) Press). These anchors can serve for adhesion of the peptides to a solid support, e.g. a polymer matrix, which can for example be used as packing in a chromatography column, or can be used on a microtiter plate or some other support.

At the same time, these anchors can also be used for recognition of the esterases. For recognition of the esterases, it is also possible to employ usual markers, such as fluorescence dyes, enzyme markers, which after reaction with a substrate form a detectable reaction product, or radioactive markers, alone or in combination with the anchors for derivatization of the esterases.

6. Reactors

The method according to the invention can be carried out in reactors that are usual in this field, and at various scales, for example at the laboratory scale (a few milliliters to dozens of liters) or on an industrial scale (liters to several thousand cubic meters). If the esterase is used in the form of an isolated, more or less purified enzyme, a chemical reactor can be used. If, within the scope of the method according to the invention, the esterase used is produced by a microorganism and optionally is released in the reaction medium, so that ester cleavage can take place there, then a bioreactor (fermenter) is used, in which as well as suitable process conditions for ester cleavage, suitable living conditions must also be provided for the esterase-producing microorganisms (e.g. by providing a suitable nutrient medium and pH, a suitable temperature, supply of oxygen or other gases, antibiotics, etc.). A bioreactor is therefore suitable for the preparation of the esterases by a whole-cell system, in which living microorganisms (for example prokaryotic cells such as bacteria or archaebacteria, or eukaryotic cells such as yeasts, mammalian cells or insect cells) are cultivated. A person skilled in the art is familiar with the various aspects of the use of reactors, for example the upscaling of chemical or biotechnological processes from the laboratory scale to large-scale industrial production and the optimization of process variables and can optionally refer to relevant technical literature (for biotechnological processes for example Crueger and Crueger, Biotechnologie—Lehrbuch der angewandten Mikrobiologie [Biotechnology—textbook of applied microbiology], 2nd edition, R. Oldenbourg Verlag, Munich, Vienna, 1984).

7. Reaction Products

The present invention also relates to the reaction products obtained by the method according to the invention. The reaction products can be present together with the reaction mixture used in the method according to the invention, or can be purified partially or extensively. Suitable degrees of purification can be determined routinely by a person skilled in the art as required and according to the further use and comprise for example chemical purity or analytical purity.

Suitable methods for purification are known by a person skilled in the art and comprise for example precipitation and chromatographic methods.

The reaction products obtained, which depending on the degree of the preceding ester cleavage comprise polyacrylic acids or partially esterified polyacrylic acid, can be used for example in paints and coatings, such as wall paints, coatings (e.g. for metal surfaces, in particular in the automobile industry) and paint and varnish. There are other applications in the paper industry (e.g. for influencing printability, appearance or gloss), in adhesives and sealants, in the textile industry (e.g. as binders for pigment coloring or printing processes) or in the leather industry (for example to make the surface of leather hydrophobic). Further uses include the production of textile and glass fibers, polish for floors, cars or shoes, additives for hydraulic cements, mortar or concrete. Polyacrylates are also used in plant protection and the spreading of fertilizers and as matrices for ion exchangers. Applications for polymethacrylates (i.e. poly(methylmethacrylates)) include in particular the so-called acrylic glasses as well as additives for the petroleum industry, thickeners for dispersions and in the cosmetics industry. Polymethacrylates are also used as prostheses in dentistry, as bone cement in surgery and as pharmaceutical excipients in controlled-release tablets.

With the method according to the invention it is in particular possible to prepare regiospecifically modified polymers. It was found, surprisingly, that by using enzymes that only cause hydrolytic cleavage of terminal ester groups of the polymer molecule, but not ester groups deeper within the polymer molecule, polymers selectively modified in this way can be produced relatively simply in comparison with chemical methods.

The invention will now be explained in more detail with reference to the following nonlimiting examples.

Experimental Section

Example 1

Production of an EstC Gene Bank

A gene library was produced with mutated EstC from *Burkholderia gladioli* (SEQ ID NO:51), in order to obtain functional mutants of EstC. Mutations were introduced in EstC by random mutagenesis, using the plasmid pMSP1.17 in error-prone PCR as template according to the protocol and, using the GeneMorph® II random mutagenesis kit (Stratagene), sequence errors were introduced into the PCR-amplified EstC genes. Lit: Instruction Manual GeneMorph® II Random Mutagenesis Kit (Cat#200550). Next, the PCR-amplified genes were purified with the Promega Wizard SV Gel and PCR Clean-Up System according to the protocol and were cut with the restriction enzymes NdeI and HindIII in buffer R from Fermentas. Independently of that, the plasmid pMS470A8 as vector-DNA (Balzer et al., Nucleic Acids Research, 1992, Vol. 20, No. 8, 1851-1858) was digested with the same restriction enzymes, and after thermal inactivation of the restriction enzymes (80° C., 20 min) was dephosphorylated with 1 µl Calf Intestine Alkaline Phosphatase (CIAP) from Fermentas for 1 hour at 37° C. The total DNA was applied on an agarose gel, the corresponding vector portion was cut out and was purified with the Wizard SV Gel and PCR Clean-Up System from Promega according to the protocol. Then the vector-DNA and the inserts produced were ligated with T4 DNA ligase from Fermentas for 1 hour at 20° C. The ligation product was then purified with the Wizard SV Gel and PCR Clean-Up System from Promega and desalinated and transformed into competent *E. coli* BL21 (DE3) cells with the Micropulser™ from BioRad by electroporation (2.5 kV) of each 2 µl of the plasmid DNA in 80 µl. Immediately after electroshock the cells were taken up in 1 ml of SOC medium and regenerated for 35 min at 37° C. and 550 rpm in an Eppendorf "Thermomixer comfort". The competent cells were produced according to "Current Protocols in Molecular Biology" 1.8.4. Transformed clones were selected on LB-Amp plates (100 µg/ml), 10 transformants were streaked on the aforementioned selection plates and were used for plasmid preparation according to QIAprep® Spin Miniprep Kit from Qiagen. The plasmids isolated were digested with the aforementioned restriction enzymes and the presence of an insert of the correct size was confirmed by agarose gel electrophoresis. In addition the mutation rate was determined by sequencing.

Example 2

Production of Mutated EstC Variants by Site-Directed Mutagenesis

The "QuickChange Multi-Site-directed Kit" from Stratagene (Catalog No. #200514 and #100515) was used for the site-directed mutagenesis, offering a rapid and reliable method for the site-directed mutagenesis of a plasmid DNA at up to five sites simultaneously. The mutation of each individual site requires a single mutagenic oligonucleotide, using a double-stranded DNA template. The following mutagenic oligonucleotide primers, which were devised according to the recommendations in the protocol of the QuickChange Multi-Site-directed Kit and were synthesized by Invitrogen, were used, with the mutations produced shown in parentheses:

```
SEQ ID NO: 39:
(Phe138Val)
5'-gctgctcttgtatatcttgctgcggtcatgcctgc- 3'

SEQ ID NO: 40:
(Phe138Ala)
5'-gctgctcttgtatatcttgctgcggccatgcctgc-3'

SEQ ID NO: 41:
(Glu154Ala)
5'-gtaagagcaccagcaaaccatggcgaaatgctggc- 3'

SEQ ID NO: 42:
(Leu163Ala)
5'-ctggcctcggcgatctgcgccagccct- 3'

SEQ ID NO: 43:
(Leu189Ala)
5'-cggcctatctcgccacggcgaagca- 3'

SEQ ID NO: 44:
(Leu189AlaLeu193Ala)
5'-gccacggcgaagcaggcggcgttcgaggatgttga- 3'

SEQ ID NO: 45:
(Leu193Ala)
5'-gcaggcggcgttcgaggatgttgac-3'

SEQ ID NO: 46:
(Val150Ala)
5'-gtacctggtcttgattacgcgagagctcct- 3'

SEQ ID NO: 47:
(Thr188Ser)
5'-gcctatctcgcctcgctgaagcagg- 3'
```

-continued

SEQ ID NO: 48:
(Leu160Ala)
5'-cgaaatggcggcctcgctgatctgc- 3'

SEQ ID NO: 50:
(Thr188AlaLeu189AlaLeu193Ala)
5'-tatctcgcctcggcgaagcaggcggcgttcgagga-3'

For the site-directed mutagenesis, a double-stranded DNA template was produced, employing a usual protocol for DNA minipreparations (QIAprep Spin Miniprep Kit from Qiagen). Then the reaction mixture for the synthesis of the mutated strand was prepared by PCR according to the following schedule, the individual constituents being put in the reaction vessel in the order shown in the schedule, and then mixed:

EXPERIMENTAL REACTION 2.5 µl 10×QuikChange multi-reaction buffer
2.0 µl ds-DNA template: pMS470[EstC] (50 ng)
1.0 µl dNTP-mix
1.0 µl QuikChange multi-enzyme mixture
x µl mutagenic primer (when using 1-3 primers approx. 100 ng of each primer was added, when using 4-5 primers approx. 50 ng of each primer was added)
x µl doubly distilled H$_2$O for a final volume of 25 µl
Control Reaction:
2.5 µl 10×QuikChange multi-reaction buffer
18.5 µl doubly distilled H$_2$O
1.0 µl (50 ng/µl) QuikChange multi-control template
1.0 µl QuikChange multi-control primer mixture (100 ng/µl per primer)
1.0 µl dNTP-mix
1.0 µl QuikChange multi-enzyme mixture The reactions were carried out using the parameters given in Table 1 below, using, for the control reaction, a time of 8 minutes for strand synthesis:

TABLE 1

| Segment | Cycles | Temperature | Duration |
| --- | --- | --- | --- |
| 1 | 1 | 95° C. | 1 minute |
| 2 | 30 | 95° C. | 1 minute |
|   |    | 55° C. | 1 minute |
|   |    | 65° C. | 10 minutes |

Then 1 µl of the restriction enzyme DpnI was added to each reaction mixture of the respective amplification reactions. Each reaction mixture was mixed carefully and thoroughly by taking it up into a pipet and then discharging it several times. Next, the reaction mixtures were centrifuged in a microcentrifuge for 1 min and then immediately incubated for 1 h at 37° C., in order to digest the parent (unmutated) double-stranded DNA.

Next, the PCR fragments obtained were purified after purification with the Promega Wizard SV Gel and PCR Clean-Up System according to the protocol and were digested with the restriction enzymes NdeI and HindIII in buffer R (Fermentas) and, by the procedure described in Example 1, were ligated into vector pMS470Δ8, also cut with the restriction enzymes NdeI and HindIII.

Then transformation of XL10-Gold Ultra-competent cells was performed according to the manufacturer's instructions (Stratagene).

For each transformation reaction, a suitable volume was plated on LB$_{amp}$ plates according to the information in Table 2. For control of mutagenesis, the cells were plated on LB$_{amp}$ plates that had been prepared with 80 µg/ml X-gal and 20 mM IPTG.

TABLE 2

| Type of reaction | Volume on the plate |
| --- | --- |
| Experimental mutagenesis | 1 µl, 10 µl and 100 µl |
| Mutagenesis control | 10 µl |

The transformation plates were then incubated overnight at 37° C.

The number of colonies to be expected from the mutagenesis control transformation is between 50 and 800 colonies. More than 50% of the colonies from the mutagenesis control transformation should have all three mutations and should appear as blue colonies on IPTG- and X-gal-containing agar plates. The number of colonies to be expected from the experimental mutagenesis transformation is between 10 and 1000 colonies. After the expected number of colonies had been reached, about 150 transformants were streaked on LB$_{amp}$-IPTG plates (0.2 mM IPTG) and incubated overnight at 37° C.

Example 3

Detection of Activity by Filter Assay

The EstC mutants prepared in Example 2 were investigated for their capacity for cleaving substrates with ester bonds. For this, the corresponding plasmids were in each case transformed into the expression strain E. coli BL21 (DE3) (Invitrogen). 10 colonies with the same mutation were tested first with α-naphthyl acetate.

a) Color Assay with Fast Blue B for Cleavage of Naphthol Esters

For this, the colonies and positive controls EstC, EstB and the negative control E. coli BL21 [pMS470A8] were streaked in a set pattern on LB-amp-IPTG plates (100 µg/ml ampicillin, 0.2 mM IPTG) and incubated overnight. Then the cell colonies were removed from the agar plate with a sterile paper filter (Whatman, Cat No. 1001-085) and the filter was dried for 10 minutes at 37° C. The bacterial cells were digested for 25 min at room temperature with 500 µl Bug Buster (Novagen) and the filter membranes were then equilibrated for 10 min with 0.02 M potassium phosphate buffer (pH 7.0). For the test with α-naphthyl acetate, 5 ml of buffer (0.05 M Tris-HCl, pH 7.0) was mixed with 100 µl of substrate solution (10 mg/ml α-naphthyl acetate in acetone) and 100 µl of dye solution (10 mg/ml Fast Blue B salt in H$_2$O) in a glass Petri dish and the filter membranes were impregnated. Formation of a violet-red coloration indicated the activity of the esterase.

b) pH-Shift Assay

The clones most active in each case with the substrate α-naphthyl acetate, were tested for the substrates polymethylacrylate (PMA), polybutylacrylate (PBA) and 2,4-dimethylglutaric acid-dimethyl ester (DG) and 2,4-dimethylglutaric acid-dibutyl ester (DB). For this, as described above, colonies were grown on agar plates and, as described in Example 3a, were transferred onto paper filters.

For preparation of the substrate solution, first a screening solution was prepared, which contained 400 µL phosphate buffer (0.1 M, pH=7.0), 800 µL aqua dest., 500 µL DMSO, 750 µL phenol red (10 g/l) and 400 µL NaOH (0.1 M). For pH-shift assays with DG and/or DB, in each case 200 µl of these substrates were dissolved in each case in 9.5 ml of screening solution and the filter membranes prepared above were impregnated with 1 ml of the substrate solution thus prepared. For pH-shift assays with the substrates PMA and/or PBA, in each case these were pipetted onto dry membranes, the filter membranes prepared above with the lysed cell colonies were impregnated with 1 ml of the screening solution and were laid on the membranes with the substrates. After incubation at RT, the color change from red to yellow, caused by the formation of acid groups after ester cleavage, was determined. The color change could be detected after approx. 20 minutes.

The activity of the clones used is shown in FIG. 5, using the following symbols:
+++: very active
++: active
+: weakly active
o: inactive

Example 4

Preparation of Esterase-Containing Raw Bacterial Lysates

For production of enzyme-containing raw bacterial lysate, first 30 ml of LB medium as preculture, which contained 100 µg/ml ampicillin (hereinafter: $LB_{amp}$) in a 100 ml Erlenmeyer flask, was inoculated with a bacterial colony and was cultivated overnight on a shaking table at 37° C. and 180 rev/min. Then for the main culture, 500 ml of culture medium [2×TY (10 g/L yeast extract, 16 g/L tryptone, 5 g/L NaCl)] was inoculated with an aliquot of the preculture to an $OD_{600}$ of 0.1 and was cultivated at 30° C., until an $OD_{600}$ of 0.5-0.8 was reached. This was followed by induction of expression with 0.1 mM IPTG and incubation for 16 h at 28° C. The bacterial culture was then centrifuged for 30 min at 4° C. in 1000-ml centrifuge tubes at 4000 rev/min (=3062× g) and the pellets were in each case suspended in 20 ml of 0.1 M phosphate buffer (pH 7). Cell lysis was performed by 5 min of ultrasound treatment, followed by a 1-minute pause, and a further 5 min of ultrasound treatment, using a Branson Sonifier 250, with the duty cycle set at 50% and the power control at level 5. The lysis product obtained was centrifuged for 1 h at 40000 rev/min (=117734×g), sterile-filtered using a membrane with a pore size of 0.2 µm and stored at −20° C. until it was used.

Example 5

Standardization of Enzyme Activity

Raw lysate, prepared as in Example 4, was used as substrate in a photometric assay for cleavage of para-nitrophenylbutyrate (p-NPB) (moreover, a person skilled in the art is able, on the basis of his technical knowledge, to develop assays based on other suitable substrates, for example para-nitrophenylacetate, p-NPA). In this test for determination of esterase activity with para-nitrophenyl esters, 980 µl of buffer (1M Tris buffer, pH 7.0) was mixed with 10 µl of enzyme solution (or dilution of enzyme solution with 1M Tris buffer, pH 7.0) in a cuvette. The reaction was started with 10 µl of substrate solution (400 mM para-nitrophenyl ester in DMSO) and the increase in para-nitrophenol was monitored in a Beckmann UV spectrophotometer at a wavelength of 405 nm.

$\varepsilon$=(para-nitrophenol)11.86 mM$^{-1}$cm$^{-1}$(determined at pH7.0)

Formula for calculation of activity:

$$U/ml = \frac{\Delta Abs/min \times V}{\varepsilon \times 1 \times v} \times \text{dilution}$$

One unit (U) of esterase corresponds to the amount that leads in this assay to conversion of 1 µmol/min.

Example 6

Detection of Enzyme-Catalyzed Cleavage

Figure 6:
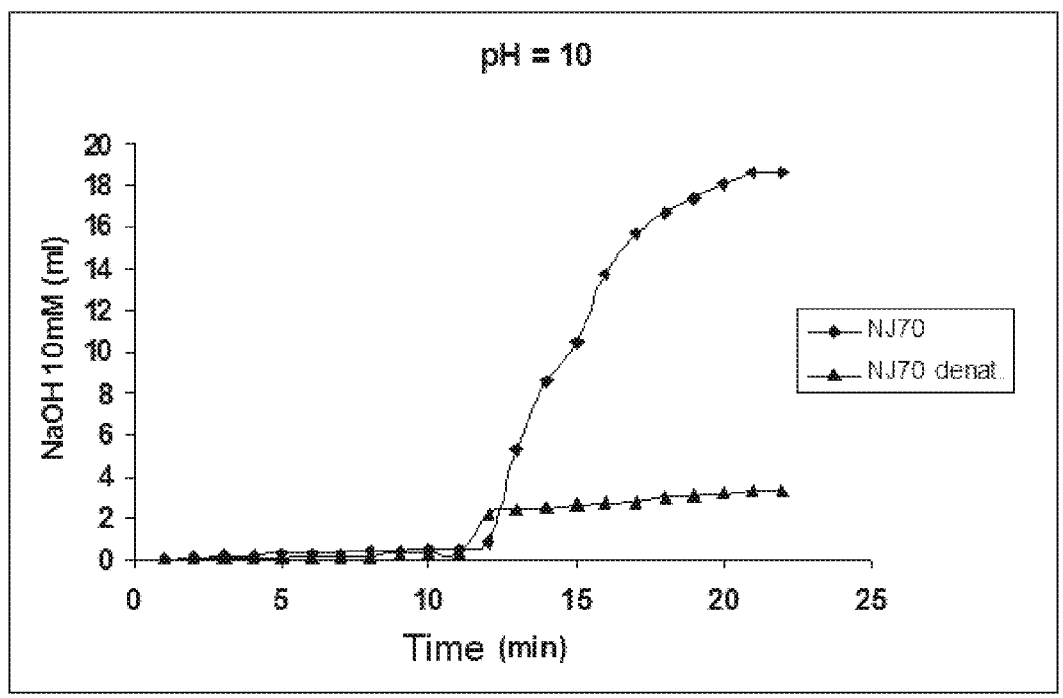
FIG. 6 shows the enzyme-catalyzed ester cleavage of PBA after adding raw lysate of the esterase-producing strain NJ70 (equivalent to 1000 units of EstB_NJ70) in comparison with chemical ester cleavage after adding raw lysate after denaturation.

For differentiation of enzyme-catalyzed substrate cleavage and chemical substrate cleavage, a raw lysate of strain NJ70 (containing a functional mutant of esterase B from *Burkholderia gladioli*, EstB_NJ70, according to SEQ ID NO:4) was prepared according to Example 4. As substrate solution, 750 µl of PBA solution (CAS No.: 9003-49-0, Sigma Aldrich, 25-30 wt. % in toluene) (equivalent to 1.75 mmol of monomeric ester groups) was added to 35 ml of a master mix (340 ml 0.9% NaCl, 220 ml toluene, 70 ml Emulgen (10% solution in $H_2O$), pH 7) Emulgen 913, Batch 2265, Kao Chemicals, Osaka Japan, alternatively Tergitol NP-9 from Aldrich can be used) and the pH of the solution was adjusted to 10 with 10 mM NaOH solution. Then 500 µl of raw lysate (equivalent to 1000 units according to the standard established in Example 5) was added and the drop in pH due to acid groups released in the course of cleavage of the ester bonds was compensated by adding 10 mM NaOH. For determination of chemical autolysis, in an independent assay 500 µl of raw lysate with enzyme denatured by boiling for 30 min at 80° C. was added. The results are shown in FIG. 6. After active enzyme is added, because of the acid groups that are released, a large addition of 10 mM NaOH is required for keeping the pH at 10 (curve with rhombus symbols in FIG. 6). In contrast, with additions of denatured enzyme there is only slight ester cleavage by chemical autolysis (curve with triangles in FIG. 6). The sudden increase in consumption of pH correctant (NaOH) immediately after addition of raw lysate with denatured enzyme can be explained by the pH of 7 of the raw lysate.

Example 7

Inhibition of Enzyme-Catalyzed Cleavage by Polyacrylic Acid

The corresponding tests were carried out similarly to Example 6 in aqueous solution, with acid groups being formed by the enzyme-catalyzed cleavage of ester bonds of the substrate used, polybutylacrylate (PBA). These acid groups led to a drop in pH, which was compensated by adding 10 mM NaOH. The amount of NaOH added thus reflects the course of the reaction. All measurements were performed in 35 ml of reaction mixture at pH=9.0 and a temperature of 37° C. 350 units of the esterase EstB_NJ70 (SEQ ID NO:4) and 750 µl of the PBA solution were used, which corresponds to 1.75 mmol of monomeric ester groups. 10 mM NaOH was used as titration solution.

For determination of possible product inhibition, in a parallel assay, at the start of measurement 850 µl of a 20% Sokalan solution was added (Sokalan PA: 15 (polyacrylic acid, Mw 1200, pH 8.0), which is equivalent to 1.74 mmol of monomeric acrylic acid units. As can be seen from the results shown in FIG. 2, the enzymes from *Burkholderia*

Figure 7:
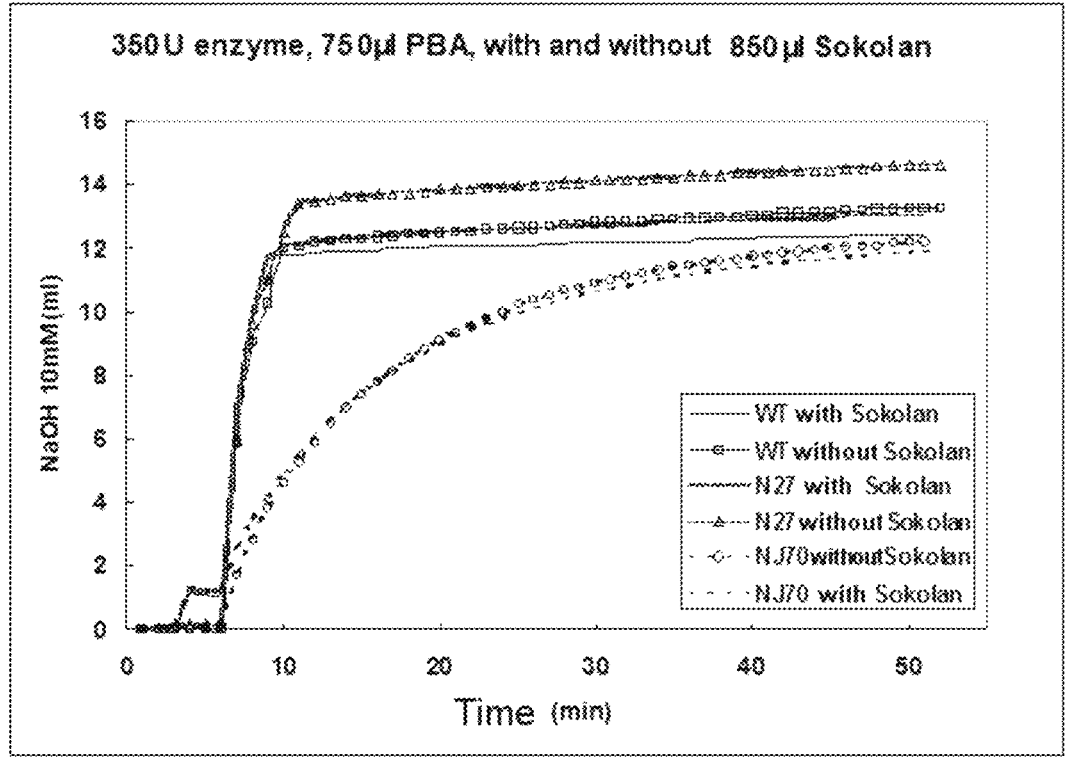
FIG. 7 shows autotitrations of EstB-esterases (wild type and mutants) with the substrate PBA. A possible inhibitory action of Sokalan (=polyacrylic acid) was investigated.

*gladioli* (SEQ ID NO:1; WT in FIG. 7) that were used, and their functional mutants EstB_N27 (SEQ ID NO:3) or EstB_NJ70 (SEQ ID NO:4) were not inhibited or were only minimally inhibited by Sokalan.

Example 8

Dependence of Enzyme-Catalyzed Ester Cleavage on pH

Figure 8:
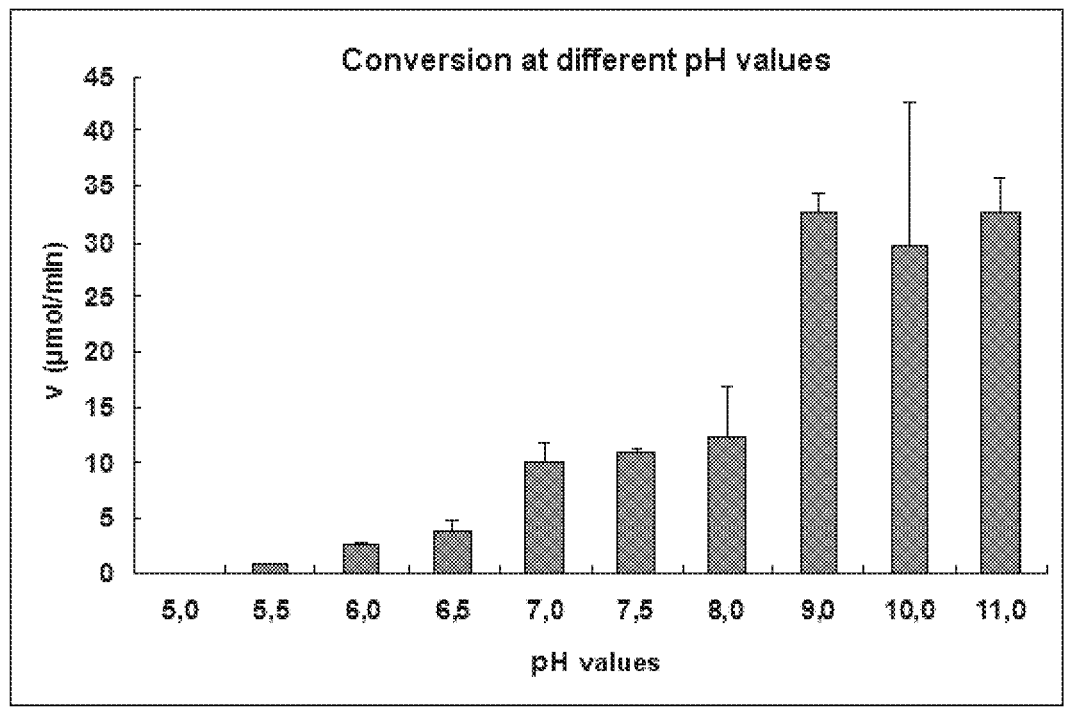
FIG. 8 shows the enzyme-catalyzed ester cleavage as a function of pH. All measurements were performed with 1000 units of EstB_NJ70 (determined with p-NPB) and 750 µl PBA.

The enzyme-catalyzed ester cleavage was investigated as a function of pH similarly to Example 6. The raw lysates of strain NJ70 (which expresses the functional mutant NJ70, i.e. SEQ ID NO:4) were prepared as described in Example 4 and an amount equivalent to 1000 units was added to substrate solutions, which had been adjusted to various pH values in the range from 5 to 11. To detect possible chemical autohydrolysis at higher pH values (in the range from about pH ~9.0 to pH 11.0), the raw lysates were not added until after 10 min, and in no case was a notable consumption of pH correctant (NaOH) observed prior to addition. It can be seen from the results shown in FIG. 8 that ester cleavage took place in the range from pH 5 to pH 11.

Example 9

Temperature Dependence of Enzyme-Catalyzed Ester Cleavage

Figure 9:
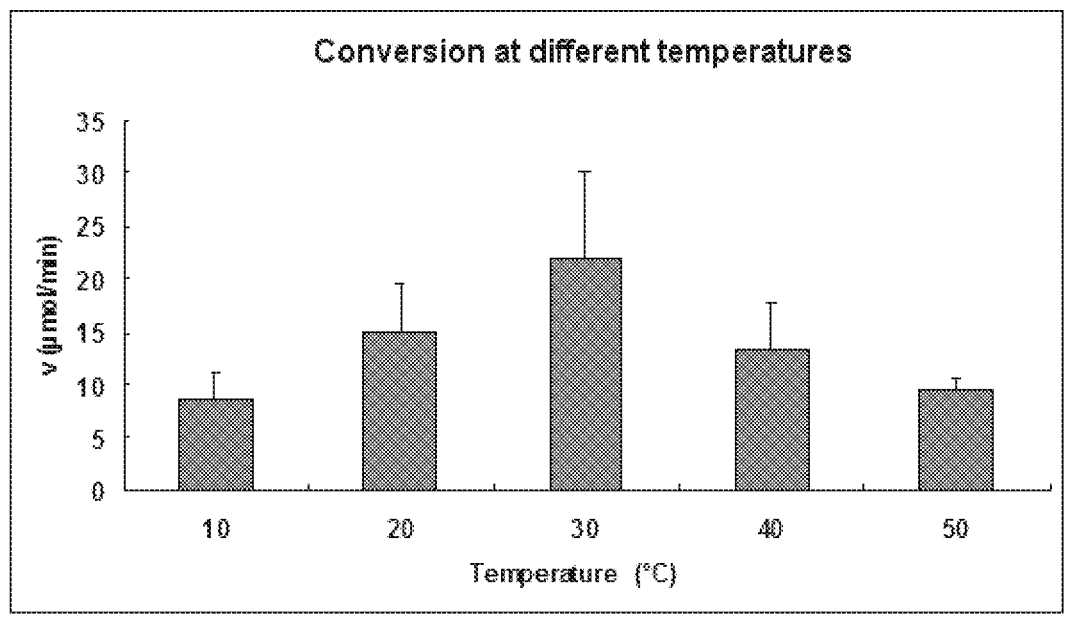
FIG. 9 shows the temperature dependence of enzyme-catalyzed ester cleavage. All autotitrations were performed with 1000 units of EstB_NJ70 (determined with p-NPB) and 750 µl PBA.

The temperature dependence of enzyme-catalyzed ester cleavage was investigated as in Example 6 at a constant pH of 9. As described in Example 4, raw lysates of strain NJ70 were prepared, and were added in an amount equivalent in each case to 1000 units to substrate solutions and were autotitrated at various temperatures in the range from 10° C. to 50° C. As control for chemical autohydrolysis, substrate solution with a pH of 9 was incubated for 10 min at the stated temperature. In the absence of pH change (no consumption of pH correctant), it was concluded that there was no autohydrolysis. It can be seen from the data presented in FIG. 9 that there was a temperature optimum in the range from 20° C. to 40° C., in particular at 30° C.

Example 10

Figure 10:
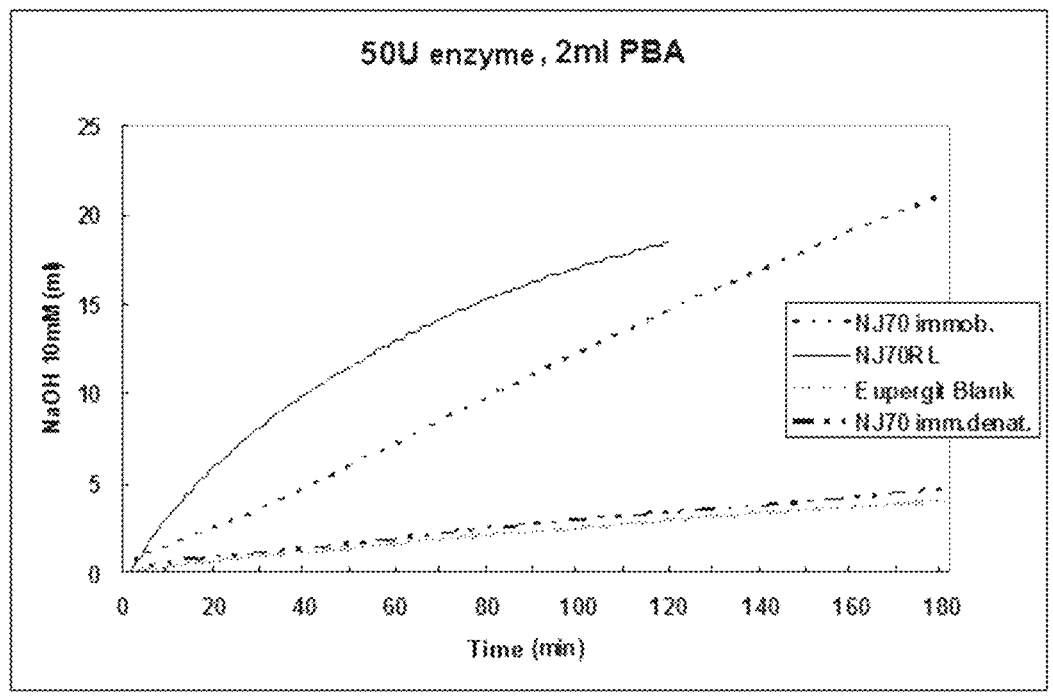
FIG. 10 shows the course of the reaction of ester cleavage by EstB_NJ70 in solution or immobilized EstB_NJ70. The results are shown of autotitrations with 4.66 mmol PBA of EstB_NJ70 either nonimmobilized or immobilized on Eupergit.

Enzyme Activity of Immobilized Esterase 35 ml of a master mix (340 mL of 0.9% NaCl solution, 220 mL toluene and 70 mL Tergitol (10% in $H_2O$)), which contained 2 ml of PBA solution (Sigma Aldrich, Mw 99 000, 25-30 wt. % in toluene) (equivalent to 4.66 mmol monomeric ester groups), was adjusted to a pH of 9 and held at a temperature of 37° C. 3.6 ml of raw lysate containing EstB_NJ70 was rotated with 0.5 g of Eupergit C250L (Aldrich) and 30 ml of 0.5 M $K_2HPO_4$ buffer (pH 9.5) for 48 h at room temperature. Then the suspension was drawn off and the matrix material was washed with 0.1 M Tris buffer (pH 7.0). Then a . . . was Protein determination according to Bradford showed that 86% of the protein had bound to the support. 50 units of EstB_NJ70, 50 units of EstB_NJ70 immobilized on Eupergit, units of EstB_NJ70 immobilized on Eupergit and denatured, or the corresponding amount of Eupergit without the immobilized enzyme, were added in each case to 35 ml of the aforementioned reaction mixture. The pH was compensated by adding 10 mM NaOH. As shown in FIG. 10, with addition of the two controls (Eupergit without EstB_NJ70 or with denatured EstB_NJ70), slight release of acid groups was observed. In contrast, addition of EstB_NJ70 or immobilized EstB_NJ70 led to a far greater release of acid groups, with the course of the reaction in the case of EstB_NJ70 corresponding to a saturation curve with comparatively high initial reaction rate and a later slowing, whereas the course of the reaction in the case of immobilized EstB_NJ70 had an initially lower rate, but then remained constant during the period of measurement.

Example 11

Ester Cleavage with Short-Chain and Long-Chain Substrates

Figure 11:
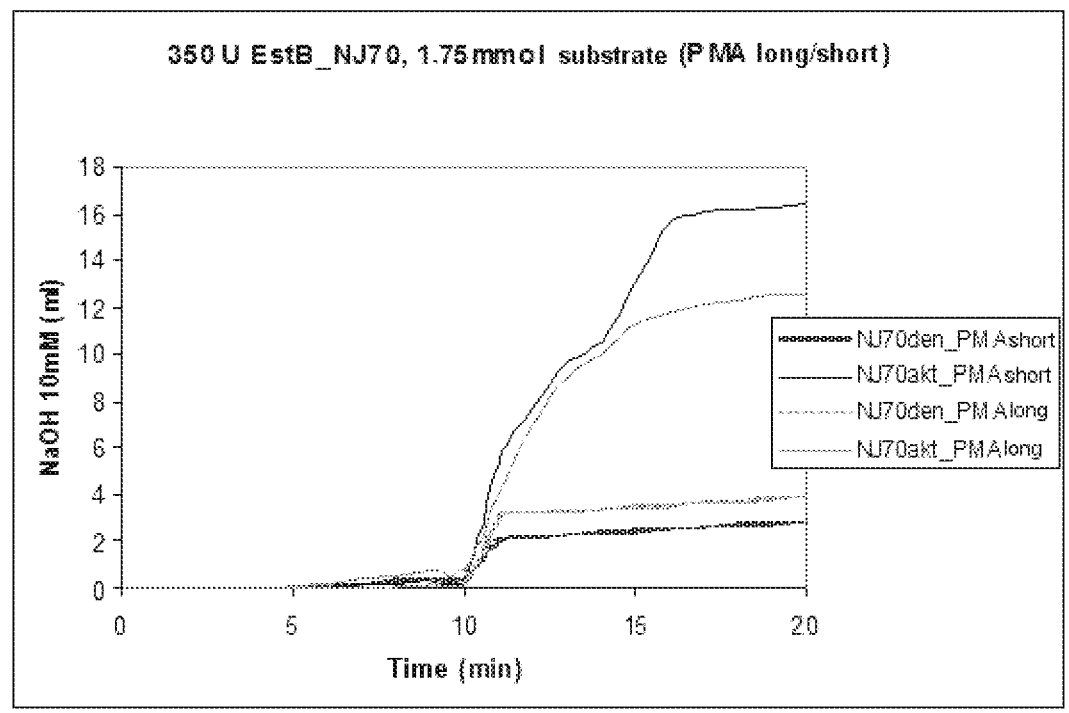
FIG. 11 shows the cleavage of polyacrylic acid methyl esters of different chains length, with denatured enzyme used as control.

In each case 35 ml of the reaction mixture stated in Example 10 was adjusted to a pH of 9.0 and a temperature of 37° C. Then in each case 350 units of the esterases stated in FIG. 11 and either short-chain PMA (Sigma Aldrich) with a molecular weight of 30000 (PMAshort in FIG. 11) or long-chain PMA (PMAlong in FIG. 11) with a molecular weight of 40000 were added, equivalent in both cases to 1.75 mmol of monomeric ester groups, and the reaction was carried out either until establishment of equilibrium (FIG. 6) or for the stated period (FIG. 11). The drop in pH due to ester cleavage was compensated by adding 10 mM NaOH, and in FIG. 11, the percentage of hydrolyzed ester groups was calculated from the consumption of NaOH. It can be seen from FIG. 11 that both short-chain and long-chain PMA are cleaved enzymatically. In the case of denatured enzymes (NJ70 den in FIG. 11) the variation in consumption of correctant (NaOH) can be explained by the addition of the respective component to the reaction mixture, as the latter does not have any buffering capacity, so that even minimal amounts of solutions with different pH affect the overall pH.

Reference is made expressly to the disclosure of the publications cited in the present description.

Review of the SEQ ID NOs and Strain Designations Used

SEQ ID NO:1

Protein sequence (wild type) of EstB from *Burkholderia gladioli*

SEQ ID NO:2

Protein sequence (wild type) of EstC from *Burkholderia gladioli*

SEQ ID NO:3

Mutated protein sequence (internal designation: N27; EstB_N27), for which the following amino acid exchanges were made relative to the wild-type EstB (SEQ ID NO:1): Ser17Leu; Gly132Ser; Glu251Gly; Ala311Val; Glu316Lys

SEQ ID NO:4

Mutated protein sequence (internal designation: NJ70; NJ 70; EstB_NJ70), for which the following amino acid exchanges were made relative to the wild-type EstB (SEQ ID NO:1):

Pro8Leu; Gly132Ser; Trp134Arg; Arg155Cys; Glu251Gly; Ala311Val; Glu316Lys

SEQ ID NO:5

Cutinase from *Humicola insolens*

SEQ ID NO:6

Lipase B from *Candida antarctica*

SEQ ID NO:7

Esterase from *Burkholderia ambifaria* (internal designation: AOTF86_9BURK@1)

SEQ ID NO:8

Esterase from *Burkholderia cenocepacia* (internal designation: Q1BK05_BURCA@1)

SEQ ID NO:9
Esterase from *Burkholderia cenocepacia* (internal designation: A2W245_9BURK@1)
SEQ ID NO:10
Esterase from *Burkholderia cenocepacia* (internal designation: A0U6R7_9BURK@1)
SEQ ID NO:11
Esterase from *Burkholderia cenocepacia* (internal designation: A0B440_BURCH@1)
SEQ ID NO:12
Esterase from *Burkholderia cepacia* (internal designation: Q0B5R9_BURCM@1)
SEQ ID NO:13
Esterase from *Burkholderia dolosa* (internal designation: A2WH69_9BURK@1)
SEQ ID NO:14
Esterase from *Burkholderia mallei* (internal designation: ZP_00928253@1)
SEQ ID NO:15
Esterase from *Burkholderia mallei* (internal designation: Q629M1_BURMA@1)
SEQ ID NO:16
Esterase from *Burkholderia mallei* (internal designation: A5XMR0_BURMA@1)
SEQ ID NO:17
Esterase from *Burkholderia mallei* (internal designation: A3MH33_BURM7@1)
SEQ ID NO:18
Esterase from *Burkholderia mallei* (internal designation: A1UXM8_BURMS@1)
SEQ ID NO:19
Esterase from *Burkholderia multivorans* (internal designation: AOUE35_9BURK@1)
SEQ ID NO:20
Esterase from *Burkholderia pseudomallei* (internal designation: ZP_0131527(3) 1)
SEQ ID NO:21
Esterase from *Burkholderia pseudomallei* (internal designation: ZP_01209854@1)
SEQ ID NO:22
Esterase from *Burkholderia pseudomallei* (internal designation: ZP_00893464@1)
SEQ ID NO:23
Esterase from *Burkholderia pseudomallei* (internal designation: Q3JIF4_BURP1@1)
SEQ ID NO:24
Esterase from *Burkholderia pseudomallei* (internal designation: A4LP64_BURPS@1)
SEQ ID NO:25
Esterase from *Burkholderia pseudomallei* (internal designation: A3PA33_BURP0@1)
SEQ ID NO:26
Esterase from *Burkholderia pseudomallei* (internal designation: A3NPJ8_BURP6@1)
SEQ ID NO:27
Esterase from *Burkholderia* sp. (internal designation: Q39BM9_BURS3@1)
SEQ ID NO:28
Esterase from *Burkholderia thailandensis* (internal designation: Q2T2Q0_BURTA@1)
SEQ ID NO:29
Esterase from *Burkholderia vietnamensis* (internal designation: A4JKI4_BURVG@1)
SEQ ID NO:30
Esterase from *Mycobacterium smegmatis* (internal designation: AOR6Y0_MYCS2@1)
SEQ ID NO:31
Esterase from *Saccharopolyspora erythraea* (internal designation: A4FPB3_SACEN@1)
SEQ ID NO:32
Esterase from *Saccharopolyspora erythraea* (internal designation: A4FDCO_SACEN@1)
SEQ ID NO:33
Esterase from *Saccharopolyspora erythraea* (internal designation: A4F6M6_SACEN@1)
SEQ ID NO:34
Esterase from *Stigmatella aurantiaca* (internal designation: Q096X7_STIAU@1)
SEQ ID NO:35
Esterase from *Streptomyces ambofaciens* (internal designation: A3KIK7_STRAM@1)
SEQ ID NO:36
Esterase from *Streptomyces coelicolor* (internal designation: NP_630279@1)
SEQ ID NO:37
deletion mutant of EstB_N27 designated as EstB_Short4 (or EstB_N27 Short4), in which the amino acids 317-319 (RGP) from SEQ ID NO:3 (EstB_N27) were removed
SEQ ID NO:38
deletion mutant of EstB_N27 designated as EstB_Short5 (or EstB_N27 Short5), in which the amino acids 248-255 (PLPGGHGA) of SEQ ID NO:3 (EstB_N27) were replaced with the shorter sequence SLGTT
SEQ ID NO:39 to SEQ ID NO:49:
PCR primers according to Example 2
SEQ ID NO:50
Nucleic acid sequence of EstB (according to SEQ ID NO:1)
SEQ ID NO:51
Nucleic acid sequence of EstC (according to SEQ ID NO:2)
SEQ ID NO:52
Nucleic acid sequence of cutinase (according to SEQ ID NO:5)
SEQ ID NO:53
Nucleic acid sequence of lipase B (according to SEQ ID NO: 6)
SEQ ID NO:54
Nucleic acid sequence for EstB_N27 (according to SEQ ID NO:3)
SEQ ID NO:55
Nucleic acid sequence for EstB_NJ70 (according to SEQ ID NO:4)
SEQ ID NO:56
Nucleic acid sequence for EstB_N27 Short 4 (according to SEQ ID NO:37)
SEQ ID NO:57
Nucleic acid sequence for EstB_N27 Short 5 (according to SEQ ID NO:38)
SEQ ID NO:58
Hydroxynitrile lyase from *Hevea brasiliensis* (GenBank No. AAC49184)
SEQ ID NO:59
Hydroxynitrile lyase from *Manihot esculenta* (SwissProt No. P52705)

The invention claimed is:

1. A functional esterase mutant of the esterase of SEQ ID NO: 1, wherein said functional esterase mutant has:
   i) comparable or increased activity with respect to the hydrolysis of polyacrylic acid esters relative to the esterase of SEQ ID NO: 1;
   ii) increased stability relative to SEQ ID NO: 1; and/or
   iii) increased hydrolytic activity against at least one of polyacrylic acid methyl esters or polyacrylic acid butyl relative to the esterase of SEQ ID NO: 1;
   and wherein said functional esterase mutant is:
   a) a mutant of the esterase of SEQ ID NO: 1 and comprises a mutation in one or more of the amino acid residues selected from Ser17, Gly132, Trp134, Arg155, Glu251, Ala311 and Glu316;
   b) a mutant of the esterase of SEQ ID NO: 1 and comprises at least one of the mutations selected from Ser17Leu, Gly132Ser, Glu251Gly, Ala311Val and Glu316Lys,
   c) a mutant of the esterase of SEQ ID NO: 1 and comprises at least one of the mutations selected from Pro8Leu, Gly132Ser, Trp134Arg, Arg155Cys, Glu251Gly, Ala311Val and Glu316Lys; or
   d) a mutant of the esterase of SEQ ID NO: 1 and comprises the amino acid sequence of SEQ ID NO: 37 or SEQ ID NO: 38.

2. A method for the enzyme-catalyzed hydrolysis of polyacrylic acid esters, the method comprising:
   a) preparing a polyacrylic acid ester,
   b) incubating the polyacrylic acid ester with the functional esterase mutant of claim 1, whereby at least one ester group of the polyacrylic acid ester is hydrolytically cleaved; and
   c) optionally, isolating the modified polymer.

3. The method of claim 2, wherein the polyacrylic acid ester is a homopolymer or a copolymer.

4. The method of claim 2, wherein the polyacrylic acid ester is an alternating copolymer, a random copolymer, a gradient copolymer, a block copolymer or a graft copolymer.

5. The method of claim 2, wherein the modified polymer comprises monomer building blocks of general formula I $$R^1R^2C=CR^3-COOR^4 \qquad (I)$$

wherein $R^1$, $R^2$ and $R^3$ may be identical or different and are selected from the group consisting of H, a linear $C_1$-$C_{20}$ hydrocarbyl residue and a branched $C_3$-$C_{20}$ hydrocarbyl residue, and $R^4$ is selected from the group consisting of H, a linear $C_1$-$C_{20}$ hydrocarbyl residue, a branched $C_3$-$C_{20}$ hydrocarbyl residue and a cyclic $C_3$-$C_{20}$ hydrocarbyl residue, the hydrocarbyl residue optionally is substituted with one or more identical or different groups, selected from hydroxyl, amino, epoxide, thiol groups and halogen atoms, and in the polymer, in at least one monomer building block of formula I, $R^4$ is not H.

6. The method of claim 5, wherein the polyacrylic acid ester contains, additionally to the monomers of formula I, at least one further monomer component different therefrom, in a molar proportion from 0 to 15 mol. %, which is preferably selected from N-vinylformamide, methacrylic acid, methacrylic acid ester, itaconic acid, itaconic acid ester, vinylphosphonic acid, vinylsulfonic acid, vinyl alcohol, N-vinylimidazole, N-vinylformamide, styrene, maleic acid, maleic acid ester, ethylene and/or propylene, and acrylamide and substituted acrylamides, where the substituent is selected from a linear $C_1$-$C_{20}$ hydrocarbyl residue, a branched $C_3$-$C_{20}$ hydrocarbyl residue and a cyclic $C_3$-$C_{20}$ hydrocarbyl residue, the hydrocarbyl residue optionally being substituted with one or more identical or different groups, which are selected from hydroxyl, amino, epoxide, thiol groups and halogen atoms.

7. A functional esterase mutant of the esterase of SEQ ID NO: 2, wherein said functional esterase mutant has:
  i) comparable or increased activity with respect to the hydrolysis of polyacrylic acid esters relative to the esterase of SEQ ID NO: 2;
  ii) increased stability relative to SEQ ID NO: 2; and/or
  iii) increased hydrolytic activity against at least one of polyacrylic acid methyl esters or polyacrylic acid butyl relative to the esterase of SEQ ID NO: 2;
and wherein said functional esterase mutant is:
  a) a mutant of the esterase of SEQ ID NO: 2 and comprises a mutation in one or more of the amino acid residues selected from Phe138, Val150, Leu160, Thr188 and Leu193; or
  b) a mutant of the esterase of SEQ ID NO: 2 and comprises one of the following mutations or combinations of mutations: (a) Phe138Ala; (b) Phe138Ala, Thr188Ser; (c) Phe138Ala, Leu160Ala, Thr188Ser; (d) Leu193Ala; (e) Leu193Ala, Phe138Ala, Thr188Ser, Val150Ala; (f) Leu193Ala, Phe138Ala, Thr188Ser; (g) Leu193Ala, Phe138Ala, Thr188Ser, Leu160Ala, Val150Ala; (h) Val150Ala; (i) Val150Ala, Thr188Ser; (j) Leu193Ala, Phe138Val; (k) Leu193Ala, Phe138Val, Thr188Ser, Val150Ala; (l) Leu193Ala, Thr188Ser; (m) Leu193Ala, Phe138Val, Thr188Ser; (n) Leu193Ala, Phe138Val, Thr188Ser, Leu160Ala; (o) Phe138Val, Val150Ala, Thr188Ser; (p) Phe138Val; or (q) Phe138Val, Thr188Ser.

8. A method for the enzyme-catalyzed hydrolysis of polyacrylic acid esters, the method comprising:
  a) preparing a polyacrylic acid ester,
  b) incubating the polyacrylic acid ester with the functional esterase mutant of claim 7, whereby at least one ester group of the polyacrylic acid ester is hydrolytically cleaved; and
  c) optionally, isolating the modified polymer.

9. The method of claim 8, wherein the polyacrylic acid ester is a homopolymer or a copolymer.

10. The method of claim 8, wherein the polyacrylic acid ester is an alternating copolymer, a random copolymer, a gradient copolymer, a block copolymer or a graft copolymer.

11. The method of claim 8, wherein the modified polymer comprises monomer building blocks of general formula I $$R^1R^2C=CR^3-COOR^4 \qquad (I)$$

wherein
$R^1$, $R^2$ and $R^3$ may be identical or different and are selected from the group consisting of H, a linear $C_1$-$C_{20}$ hydrocarbyl residue and a branched $C_3$-$C_{20}$ hydrocarbyl residue, and $R^4$ is selected from the group consisting of H, a linear $C_1$-$C_{20}$ hydrocarbyl residue, a branched $C_3$-$C_{20}$ hydrocarbyl residue and a cyclic $C_3$-$C_{20}$ hydrocarbyl residue, the hydrocarbyl residue optionally is substituted with one or more identical or different groups, selected from hydroxyl, amino, epoxide, thiol groups and halogen atoms, and in the polymer, in at least one monomer building block of formula I, $R^4$ is not H.

12. The method of claim 11, wherein the polyacrylic acid ester contains, additionally to the monomers of formula I, at least one further monomer component different therefrom, in a molar proportion from 0 to 15 mol. %, which is preferably selected from N-vinylformamide, methacrylic acid, methacrylic acid ester, itaconic acid, itaconic acid ester, vinylphosphonic acid, vinylsulfonic acid, vinyl alcohol, N-vinylimidazole, N-vinylformamide, styrene, maleic acid, maleic acid ester, ethylene and/or propylene, and acrylamide and substituted acrylamides, where the substituent is selected from a linear $C_1$-$C_{20}$ hydrocarbyl residue, a branched $C_3$-$C_{20}$ hydrocarbyl residue and a cyclic $C_3$-$C_{20}$ hydrocarbyl residue, the hydrocarbyl residue optionally being substituted with one or more identical or different groups, which are selected from hydroxyl, amino, epoxide, thiol groups and halogen atoms.

* * * * *